US009452225B2

(12) United States Patent
Norrild

(10) Patent No.: US 9,452,225 B2
(45) Date of Patent: Sep. 27, 2016

(54) GLP-1 PRODRUGS

(71) Applicant: Novo Nordisk A/S, Bagsvaerd (DK)

(72) Inventor: Jens C. Norrild, Birkeroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/379,445

(22) PCT Filed: Feb. 26, 2013

(86) PCT No.: PCT/EP2013/053796
§ 371 (c)(1),
(2) Date: Aug. 18, 2014

(87) PCT Pub. No.: WO2013/127779
PCT Pub. Date: Sep. 6, 2013

(65) Prior Publication Data
US 2015/0045281 A1 Feb. 12, 2015

(30) Foreign Application Priority Data
Mar. 1, 2012 (EP) .................................... 12157638

(51) Int. Cl.
*A61K 38/00* (2006.01)
*C07K 14/605* (2006.01)
*A61K 47/48* (2006.01)
*A61K 38/26* (2006.01)
*C07K 14/575* (2006.01)

(52) U.S. Cl.
CPC ......... *A61K 47/48269* (2013.01); *A61K 38/26* (2013.01); *C07K 14/575* (2013.01); *C07K 14/605* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,966,848 A * | 10/1990 | Smith et al. ................... | 435/193 |
| 5,223,421 A * | 6/1993 | Smith et al. ................... | 435/193 |
| 5,837,218 A * | 11/1998 | Peers et al. ................... | 424/1.69 |
| 6,620,910 B1 | 9/2003 | Calas et al. | |
| 2004/0235726 A1* | 11/2004 | Jakubowski et al. ........... | 514/12 |
| 2011/0065633 A1 | 3/2011 | Dimarchi et al. | |
| 2011/0237493 A1 | 9/2011 | DiMarchi | |

FOREIGN PATENT DOCUMENTS

| | | |
|---|---|---|
| WO | 2009/058662 A2 | 5/2009 |
| WO | 2009058734 A1 | 5/2009 |
| WO | 2009/099763 A1 | 8/2009 |
| WO | 2010071807 A1 | 6/2010 |
| WO | 2011/080103 A1 | 7/2011 |

OTHER PUBLICATIONS

Wermuth et al, Glossary of Terms Used in Medicinal Chemistry, Pure & Appli. Chem. vol. 70 pp. 1129-1143 (1998).*
Santoprete A. et al,DPP-IV-resistant, long-acting oxyntomodulin derivatives, Journal :Journal of Peptide Science, Year 2011, vol. 17,pp. 270-280.
De Arnab et al.Synthesis and Characterization of Ester-Based Prodrugs of Glucagon-Like Peptide 1 Journal :Peptide Science, Year 2010, vol. 94 No. 4, pp. 448-456.
De Arnab, Design of peptide-based prodrug chemistry and its application to glucagon-like peptide 1, Journal :Master Thesis, Indiana University, year Aug. 2007.
B. Gallwitz et al.,GLP-1-analogues resistant to degradation by dipeptidyl-peptidase IV in vitro, Journal :Peptides Year 2000,vol. 86, pp. 103-111.
De Arnab et al.,Investigation of the feasibility of an Amide-based Prodrug under physiological conditions, Journal:Int J Pept Res Ther, Year 2008, vol. 14 pp. 255-262.
C. Santos et al,Cyclization-activated prodrugs. Synthesis, reactivity and toxicity of dipeptide esters of paracetamol, Journal : Bioorganic &Medicinal Chemisry letters,Year 2005, vol. 15 Issue 6, pp. 1595-1598.
D. Shan et al,Prodrug Strategies Based on Intramolecular Cyclization Reactions, Journal:Journal of Pharmaceutical Sciences, Year Jul. 1997, vol. 26 No. 7 pp. 765-767.
Carpenter K.A. et al.,Spontaneous Diketopiperazine Formation via End-to-End Cyclization of a Nonactivated Linear Tripeptide: An Unusual Chemical Reaction, Journal :Journal of American Chemical Society, Year 1994, vol. 116, pp. 8450-8458.
Oliyai R. et al. Prodrugs of Peptides and Proteins for Improved Formulation and Delivery, Journal :Annual Review of Pharmacology and Toxicology Year 1993, vol. 32,pp. 521-544.
Zheng Y. et al.Do Main Chain Hydrogen Bonds Create Dominant Electron Transfer Pathways..An Investigation in Designed Proteins, Journal:The Journal of Physical Chemistry B., Year 2003, vol. 107, No. 30, pp. 7288-7292.
Moy Kristin A et al.,Structure-activity studies of the interaction of GLP-1 with GLP-1R, Journal : Abstracts of Papers American Chemical Society, Year 2005,vol. 229,Part 2 pp. U 121.

* cited by examiner

*Primary Examiner* — Thomas S Heard
(74) *Attorney, Agent, or Firm* — Richard W. Bork

(57) ABSTRACT

The invention relates to a GLP-1 prodrug of the general formula I: R1-(NHXaa1)-Xaa2-(OHis)-(GLP-1 peptide) (Formula I), wherein GLP-1 peptide is GLP-1(8-37) (SEQ ID NO: 1) or an analog thereof having a maximum of nine amino acid changes as compared to GLP-1(8-37), R1 is lower alkyl, (NHXaa1) is an amino acid, Xaa2 is an amino acid, and (OHis) is a radical of imidazole-lactic acid; or a pharmaceutically acceptable salt, amide, or ester of the prodrug. The invention also relates to specific GLP-1 parent drugs of the general formula II: (HOHis)-(GLP-1 peptide) (Formula II), as well as specific intermediate products. The invention furthermore relates to a method of achieving release in vivo of an active and stabilized GLP-1 parent drug of the general formula II: (HOHis)-(GLP-1 peptide), by administering a GLP-1 prodrug; as well as to such GLP-1 prodrug, and such GLP-1 parent drug, respectively, for use as a medicament, in particular for use in the treatment and/or prevention of all forms of diabetes and related diseases. The prodrug may be used to alter the PK and/or absorption profile of the drug, for example to a desirable bell-shaped curve. The parent drug has a good biological activity, and is stabilized against degradation by DPP-IV.

11 Claims, 3 Drawing Sheets

SEQUENCE LISTING

```
<160> NUMBER OF SEQ ID NOS: 1

<210> SEQ ID NO 1
<211> LENGTH: 30
<212> TYPE: PRT
<213> ORGANISM: Homo sapiens
<220> FEATURE:
<221> NAME/KEY: mat_peptide
<222> LOCATION: (1)..(30)
<223> OTHER INFORMATION: GLP-1(8-37)

<400> SEQUENCE: 1

Ala Glu Gly Thr Phe Thr Ser Asp Val Ser Ser Tyr Leu Glu Gly Gln
1               5                   10                  15

Ala Ala Lys Glu Phe Ile Ala Trp Leu Val Lys Gly Arg Gly
            20                  25                  30
```

GLP-1 PRODRUGS

CROSS-REFERENCE TO RELATED APPLICATIONS

This application is a 35 U.S.C. §371 National Stage application of International Application PCT/EP2013/053796 (WO 2013/127779), filed Feb. 26, 2013, which claimed priority of European Patent Application 12157638.3, filed Mar. 1, 2012.

TECHNICAL FIELD

This invention relates to prodrugs, i.e. chemically modified versions of drugs that can undergo transformation in vivo to release the active drug. More in particular the invention relates to prodrugs of Glucagon-Like Peptide 1, GLP-1.

GLP-1 is a peptide hormone which has proven useful in the treatment of diabetes. The native hormone has, however, a very short half-life in plasma. Various derivatisation techniques, such as albumin binding and PEGylation, have been used to prolong the half-life. One example of such derivatised GLP-1 compound of an extended half-life is liraglutide, a mono-acylated GLP-1 derivative which has been approved by various health authorities and is on the market in several countries for treatment of type 2 diabetes for once daily administration.

A prodrug may, e.g., be used to alter the pharmacokinetics (PK) and/or absorption profile of the drug enhancing the therapeutic window of the drug. Further it may be used to extend the biological half-life of a drug in that its conversion into the biologically active drug is delayed by the chemical transformation reaction which takes place in vivo, after administration.

INCORPORATION-BY-REFERENCE OF THE SEQUENCE LISTING

The Sequence Listing, entitled "SEQUENCE LISTING", is 561 bytes, was created on Nov. 2, 2013 and is incorporated herein by reference. SEQ ID NO: 1 of the sequence listing is identical to residues 8-37 of native human GLP-1 (GLP-1(8-37)).

In accordance with 37 C.F.R. §1.52(e)(5), Applicants enclose herewith the Sequence Listing for the above-captioned application entitled "SEQUENCE LISTING", created on Feb. 26, 2013. The Sequence Listing is made up of 1 kilobyte, and the information contained in the attached "SEQUENCE LISTING" is identical to the information in the specification as originally filed. No new matter is added.

BACKGROUND

The Master Thesis of Arnab De, Indiana University, August 2007 entitled "Design of peptide-based prodrug chemistry and its application to glucagon-like peptide 1" discloses, i.a., the synthesis of GLP-1 ester prodrugs, based on a GLP-1 peptide with a hydroxy-terminal extension instead of an N-terminal amine (see e.g. section D-IV and D-V, class 3 and 4 compounds).

Peptide Science 2010, 94(4), 448-456 (Arnab De et al) relates to synthesis and characterization of ester-based prodrugs of glucagon-like peptide 1.

US 2011/0065633 A1 discloses, i.a., ester-based prodrugs of GLP-1 (see, e.g., Example 4).

Bioorganic & Medicinal Chemistry Letters 2005, (15), 1595-1598 (Santos et al) relates to cyclization-activated prodrugs, more in particular to synthesis, reactivity and toxicity of dipeptide esters of paracetamol. Table 1 shows the rate constants for the release of paracetamol from a dipeptide ester prodrug thereof at pH 7.4 and 37° C. A footnote to compound 4k where Y is methyl explains that the reaction was too fast to be monitoredat 37° C.

Regulatory Peptides 2000, (86), 103-111 (Gallwitz et al) relates to GLP-1-analogues resistant to degradation by dipeptidyl-peptidase IV in vitro.

Annual Review of Pharmacology and Toxicology 1993, (32), 521-544 (Oliyai and Stella) is a review article relating to prodrugs of peptides and proteins for improved formulation and delivery.

SUMMARY

The invention relates to prodrugs of insulinotropic peptides or incretins such as GLP-1. More in particular it relates to ester prodrugs. In an ester prodrug a small peptide is attached to the peptide drug via an ester bond. The ester bond may be at the N-terminus of the peptide drug, which N-terminus may therefore include a hydroxyl group. As an example the alpha-amino group of the N-terminal amino acid of the peptide drug may be modified into a hydroxyl group. According to the invention an amino acid of the small peptide extension is also modified, for example the N-terminal amino acid thereof may be modified by N-alkylation. The small peptide is preferably a dipeptide.

The mechanism by which the prodrug undergoes biotransformation in vivo is that a nucleophile component of the dipeptide (for example an amine nucleophile) cleaves the ester bond with the formation of the corresponding diketopiperazine derivative and the parent drug as a result. The parent drug may be a slightly modified version of the drug. For example the parent drug of an ester prodrug can be an N-terminal HO-version of a drug, such as an N-terminal hydroxyl peptide drug.

In a first aspect the invention relates to a GLP-1 prodrug, viz. a compound of the general formula I: R1-(NHXaa1)-Xaa2-(OHis)-(GLP-1peptide) (Formula I), wherein GLP-1 peptide is GLP-1(8-37) (SEQ ID NO: 1) or an analogue thereof having a maximum of nine amino acid changes as compared to GLP-1(8-37); R1 is lower alkyl, (NHXaa1) is an amino acid, Xaa2 is an amino acid, and (OHis) is a radical of imidazole-lactic acid of formula Chem 1:

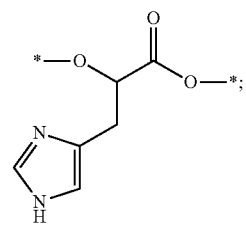

Chem. 1 or a pharmaceutically acceptable salt, amide, or ester of the prodrug.

In a second aspect the invention relates to the corresponding parent drugs, viz. the compounds of Chem. 21, Chem. 22, Chem. 23, Chem. 24, and Chem. 25, all of the general formula II: (HOHis)-(GLP-1peptide) (Formula II), wherein (HOHis) is imidazole-lactic acid corresponding to the (OHis) radical of Chem 1, as defined in the first aspect, above.

In a third aspect the invention relates to Boc-NMe-Ile-Val-OH, Boc-NMe-Val-Val-OH, (Boc-NMe-Gly-Val-OH), as well as the compound of Chem. 43. These are intermediate compounds used in the synthesis of the prodrugs of the invention.

In a fourth aspect the invention relates to a method of achieving release in vivo of an active and stabilised parent drug GLP-1 compound of the general formula II: (HOHis)-(GLP-1 peptide), or a pharmaceutically acceptable, salt, amide, or ester thereof, by administering a prodrug of the invention.

In a fifth aspect the invention relates to such prodrug, or such drug, respectively, for use as a medicament, in particular for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

The prodrug compound of the invention may be used to alter the pharmacokinetic profile and/or the absorption profile of the drug, for example to enhance the therapeutic window of the drug. Also, or alternatively, it may improve the biological half-life of the drug. The parent drug compound is biologically active. Furthermore, the parent drug may be DPP-IV stabilised per se. Also, or alternatively, the parent drug may have an extended biological half-life per se. These properties are of importance in the development of alternative and/or next generation GLP-1 compounds for subcutaneous, intravenous, and/or in particular oral administration.

For the prodrugs of the invention we have shown that, surprisingly and unexpectedly, the conversion reaction from prodrug to drug is very slow, in vitro as well as in vivo, and also that the resulting parent drugs are of a very satisfactory potency. In other words, we have shown the prodrug concept of the invention to be an interesting alternative concept to other technologies known in the art for extending the duration of action of GLP-1.

DESCRIPTION

Figure 1:
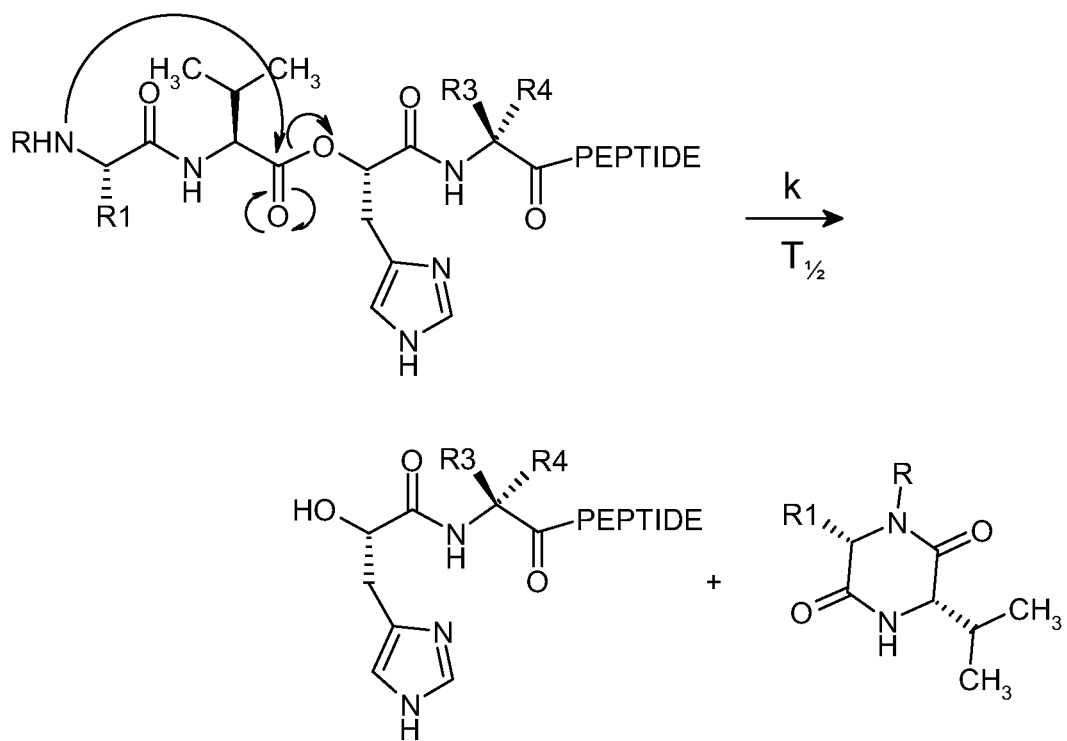
FIG. 1 is a reaction scheme showing the mechanism by which a prodrug of the invention is transformed into the corresponding HO-His7 drug of the invention (R1, R3, and R4 are amino acid side chains, R is lower alkyl, peptide represents, e.g., GLP-1(9-37) or an analogue thereof, k is the limiting conversion constant, and T½ is ln 2/k)

In what follows, Greek letters may be represented by their symbol or the corresponding written name, for example: α=alpha; β=beta; ε=epsilon; γ=gamma; ω=omega; etc. Also, the Greek letter of μ may be represented by "u", e.g. in μl=ul, or in μM=uM.

An asterisk (*) in a chemical formula designates i) a point of attachment, ii) a radical, and/or iii) an unshared electron.

GLP-1 Peptides and Analogues

In a first aspect the present invention relates to a GLP-1 peptide prodrug comprising a dipeptide extension which is attached to the N-terminus of the GLP-1 peptide via an ester bond. To this end the alpha-amino group of the N-terminal amino acid of the GLP-1 peptide is replaced by a hydroxyl group. The N-terminal amino acid of the dipeptide extension is furthermore N-alkylated.

More in particular, the invention relates to a GLP-1 compound (prodrug) of the general formula I: R1-(NHXaa1)-Xaa2-(OHis)-(GLP-1peptide) (Formula I), wherein GLP-1 peptide is GLP-1(8-37) (SEQ ID NO: 1) or an analogue thereof having a maximum of nine amino acid changes as compared to GLP-1(8-37); R1 is lower alkyl, (NHXaa1) is an amino acid, Xaa2 is an amino acid, and (OHis) is a radical of beta-imidazole-lactic acid of formula Chem 1:

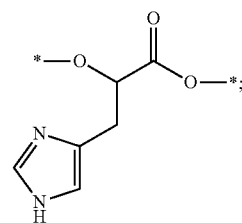

Chem. 1 or a pharmaceutically acceptable salt, amide, or ester thereof.

The GLP-1 ester prodrugs described in the background art have no N-alkylation of the N-terminal amino acid of the dipeptide extension—they either have the standard amine group, or a hydroxyl group (designated class 3 and 4, respectively, in the Thesis of Arnab De).

The mechanism by which the GLP-1 prodrug of the invention undergoes biotransformation in vivo (illustrated in FIG. 1) is that the alkylated amine nucleophile cleaves the ester bond with the formation of the corresponding diketopiperazine derivative and the parent GLP-1 peptide drug as a result. This transformation occurs spontaneously, without any other components such as enzymes or the like being required, as it is caused by the inherent chemical instability of the prodrug. In vivo esterases may, however, to some extent further enhance hydrolysis by enzymatic cleavage of the ester bond.

The N-terminal amino acid of the resulting parent GLP-1 peptide drug has a hydroxyl group instead of the usual alpha-amino group.

The prodrug compound of the invention may be useful for altering the pharmacokinetic profile. One non-limiting example of a desirable PK profile is where the curve showing plasma concentration of the parent drug versus time is kind of bell-shaped (i.e., not peak-shaped), for example along the lines of curve B in FIG. 8 of Oliyai and Stella, cited in the Background section. In one embodiment, the variation of the parent drug concentration versus time (in a prodrug administration experiment) may be reduced, for example as compared with the variation of the parent drug concentration in a corresponding administration experiment where the corresponding parent drug is administered, i.e. not the prodrug. Such experiments may be conducted in vivo, or in vitro. In another embodiment, also or alternatively, the therapeutic window of the drug may be enhanced. This may be tested in administration experiments as described in the above first embodiment. A PK profile as outlined herein above is considered potentially very useful with a view to decreasing the incidence and/or severity of adverse events that may be associated with high plasma levels of the drug in vivo.

Also, or alternatively, the prodrug of the invention may improve the biological half-life of the drug.

Also, or alternatively, the half-lives of the prodrugs of the invention are, surprisingly and unexpectedly, much improved as compared to prodrugs without N-alkylation of the N-terminal amino acid of the dipeptide extension.

Also, or alternatively, the corresponding parent drugs have a good biological activity.

Also, or alternatively, the corresponding parent drugs have an extended half-life.

Also, or alternatively, the corresponding parent drug has an improved stability against degradation by DPP-IV. DPP-IV (also designated Dipeptidyl peptidase-4, or DPP4) and also known as adenosine deaminase complexing protein 2 is an intrinsic membrane glycoprotein and a serine exopeptidase with a diverse range of substrates including proline or alanine containing peptides.

A prodrug is a pharmacological substance intended for administration in a substantially inactive form. Once administered, the prodrug is transformed in vivo into an active drug that may be termed the parent drug.

A peptide-based drug can, for example, be converted to a prodrug by covalently attaching a small peptide extension to it. In a particular embodiment the small peptide extension is added to the N-terminus of the peptide. Depending on the way the small peptide is attached, the resulting prodrug is designated either an amide prodrug, or an ester prodrug.

In an amide prodrug of a peptide drug the bond between the small peptide extension and the peptide parent drug is an amide bond.

In an ester prodrug of a peptide drug the bond between the small peptide extension and the peptide drug is an ester bond. For an ester bond to be formed one of these two components should comprise a free hydroxyl group, and the other component should comprise a free carboxylic acid group.

In a particular embodiment of the GLP-1 ester prodrug of the invention the alpha-amino group of the N-terminal amino acid of the GLP-1 peptide (parent drug) has been replaced by a hydroxyl group. This hydroxyl group is then reacted with the C-terminal carboxylic acid group of the small peptide extension to form an ester bond.

As an example, (HOHis) of formula Chem. 2a designates the amino acid His (histidine), in which the alpha-amino group has been replaced by a hydroxyl group. This group forms an ester bond with the C-terminal carboxylic acid group of the amino acid Xaa2 of the general formula I. In formula I, except for the bond between R1 and (NHXaa1), all other bonds designate amide bonds. For example, the bond between (OHis) and (GLP-1 peptide) refers to an amide bond formed between the carboxylic acid group of (OHis) and the alpha-amino group of the N-terminal amino acid of the GLP-1 peptide. The bond between R1 and (NHXaa1) refers to a C—N bond, more in particular to a bond between a C (carbon atom) of R1 and the N (nitrogen atom) in the alpha-amino group of the amino acid (NHXaa1).

In another particular embodiment the GLP-1 prodrug of the invention is a GLP-1 depsipeptide. A depsipeptide is a peptide in which one or more of the amide (*—CONHR—*) bonds are replaced by ester (*—COOR—*) bonds. In a particular embodiment of the GLP-1 depsipeptide of the invention one amide bond is replaced by an ester bond. In a further particular embodiment this one ester bond is between an alpha-hydroxyl group replacing the alpha-amino group of the N-terminal amino acid of the GLP-1 peptide (parent drug) and the C-terminal carboxylic acid group of the small peptide extension.

R1 in formula I is lower alkyl, which refers to straight or branched, particularly straight, alkyl having from one to six carbon atoms. In a particular embodiment lower alkyl is methyl.

Each of (NHXaa1) and Xaa2 in formula I independently refers to an amino acid.

In the (NHXaa1) amino acid the NH part refers to the alpha-amino group of this amino acid, the nitrogen atom of which is covalently attached to R1. Xaa1 accordingly refers to the rest of the amino acid, i.e. a radical of the type $_R$*>CH—COOH where R designates the amino acid side chain.

Amino acids are molecules containing an amine group and a carboxylic acid group, and, optionally, one or more additional groups, often referred to as a side chain.

The term amino acid includes proteinogenic amino acids (encoded by the genetic code, including natural amino acids, and standard amino acids), as well as non-proteinogenic (not found in proteins, and/or not coded for in the standard genetic code), and synthetic amino acids. Thus, the amino acids may be selected from the group of proteinogenic amino acids, non-proteinogenic amino acids, and/or synthetic amino acids.

Non-limiting examples of synthetic amino acids are the D-isomers of the amino acids.

In what follows, all amino acids for which the optical isomer is not stated is to be understood to mean the L-isomer.

Amino acid residues may be identified by their full name, their one-letter code, and/or their three-letter code. These three ways are fully equivalent.

The terms GLP-1 peptide and (GLP-1 peptide) in formula I refer to GLP-1(8-37) (SEQ ID NO: 1) or an analogue or derivative thereof. The native human Glucagon-Like Peptide 1 has the sequence of SEQ ID NO: 1 herein but extended with a His residue at the N-terminus so as to form native human GLP-1(7-37). The reason why for the present purposes reference is had to GLP-1(8-37) (emphasis added) is that in formula I the amino acid at position no. 7 is already specified, viz. as imidazole-lactic acid. The Chem. 2a hydroxyl variant of His is one (non-limiting) example of imidazole-lactic acid.

The term "GLP-1 analogue" or "analogue of GLP-1" refers to a peptide, or a compound, which is a variant of SEQ ID NO: 1. For the present purposes the peptide having the sequence of SEQ ID NO: 1 is may be designated native GLP-1(8-37).

In other words, a GLP-1 analogue is a GLP-1(8-37) peptide in which a number of amino acid residues have been changed when compared to native GLP-1(8-37) (SEQ ID NO: 1). These changes may represent, independently, one or more amino acid substitutions, additions, and/or deletions.

GLP-1 analogues may be described by reference to i) the number of the amino acid residue in native GLP-1(8-37)

which corresponds to the amino acid residue which is changed (i.e., the corresponding position in native GLP-1), and to ii) the actual change.

In the sequence listing, the first amino acid residue of SEQ ID NO: 1 (alanine) is assigned no. 1. However, in what follows—according to established practice in the art—this alanine residue is referred to as no. 8, and subsequent amino acid residues are numbered accordingly, ending with glycine no. 37. Therefore, generally, any reference herein to an amino acid residue number or a position number of the GLP-1(8-37) sequence is to the sequence starting with Ala at position 8 and ending with Gly at position 37.

The following are non-limiting examples of suitable analogue nomenclature.

An analogue which comprises at least one amino acid substitution selected from the following: 8Aib, 18K, 22E, 23R, 25V, 26R, 31K, 34R or 34Q, and/or 37K, refers to an analogue which, when compared to GLP-1(8-37) (SEQ ID NO: 1), comprises a change in at least one of the positions corresponding to position 8, 18, 22, 23, 25, 26, 31, 34, and/or 37 of GLP-1(8-37) (SEQ ID NO: 1); more precisely changed into an Aib at position 8, a lysine at position 18, a glutamic acid at position 22, an arginine at position 23, a valine at position 25, an arginine at position 26, a lysine at position 31, an arginine or a glutamine at position 34, and/or a lysine at position 37; that is, by substitution of the native amino acid at the actual position (the native amino acid is the one which is shown in SEQ ID NO: 1). For the sake of good order, positions 8, 18, 22, 23, 25, 26, 31, 34, and 37 refer to amino acids no. 1, 11, 15, 16, 19, 24, 27, and 30 using the numbering applied in the sequence listing, SEQ ID NO: 1.

Using the same logic as above, an analogue which is the variant (34R, 37K) of GLP-1(8-37) (SEQ ID NO: 1) refers to a GLP-1 peptide that is identical to SEQ ID NO: 1, i.e. native GLP-1(8-37), except that Lys$^{34}$ has been substituted with Arg$^{34}$, and Gly$^{37}$ has been substituted with Lys$^{37}$.

In a particular embodiment, the GLP-1 analogue has a maximum of 6 amino acid changes as compared to GLP-1 (8-37) (SEQ ID NO: 1).

For the present purposes terms like "comprising" and "including" are considered open-ended terms, which means that they do not exclude the presence of additional characteristic features of potential relevance (that may not be specified). For example, analogues "comprising" certain specified changes may comprise further changes, when compared to SEQ ID NO: 1. These terms may be amended to "having", "consisting of", or "consisting essentially of", and the like, which for the present purposes are considered "closed" terms, meaning that the presence of additional characteristic features of relevance (that may not be specified) is excluded. For example, when the analogue referred to above "has" the specified changes "it means that it has no other changes, when compared to SEQ ID NO: 1.

The expressions "a position equivalent to" or "corresponding position" may be used to characterise the site of change in a GLP-1 analogue (or variant) sequence by reference to native GLP-1(8-37) (SEQ ID NO: 1). Equivalent or corresponding positions, as well as the number of changes, are easily deduced, e.g. by simple handwriting and eyeballing; and/or a standard protein or peptide alignment program may be used, such as "align" which is a Needleman-Wunsch alignment. The algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −12, or preferably at −10, and the penalties for additional residues in a gap at −2, or preferably at −0.5.

An example of such alignment is inserted herein below, in which sequence no. 1 is SEQ ID NO: 1, and sequence no. 2 is the analogue (34R, 37K) thereof:

```
# 1: GLP-1 (8-37)
# 2: GLP-1 (8-37) _Analogue
# Matrix: EBLOSUM62
# Gap_penalty: 10.0
# Extend_penalty: 0.5
# Length: 30
# Identity:     28/30 (93.3%)
# Similarity:   29/30 (96.7%)
# Gaps:          0/30 ( 0.0%)
# Score: 142.0
1     1 AEGTFTSDVSSYLEGQAAKEFIAWLVKGRG    30
        ||||||||||||||||||||||||||||:||.
2     1 AEGTFTSDVSSYLEGQAAKEFIAWLVRGRK    30
```

In case of non-natural amino acids being included in the sequence, these may, for alignment purposes, be replaced with, e.g., X. If desired, X can later be manually corrected.

In a particular embodiment, the GLP-1 peptide or (GLP-1 peptide) of formula I is a GLP-1 derivative, i.e. a derivative of GLP-1(8-37) (SEQ ID NO: 1), or a derivative of an analogue of SEQ ID NO: 1.

GLP-1 Derivatives

The term "derivative" as used herein in a GLP-1 context means a chemically modified GLP-1(8-37) peptide (SEQ ID NO: 1) or a chemically modified analogue of SEQ ID NO: 1, in which at least one substituent has been covalently attached to the peptide. The substituent may also be referred to as a side chain.

In a particular embodiment, the side chain is capable of forming non-covalent aggregates with albumin, thereby promoting the circulation of the derivative with the blood stream, and also having the effect of protracting the time of action of the derivative, due to the fact that the aggregate of the GLP-1-derivative and albumin is only slowly disintegrated to release the active pharmaceutical ingredient. Thus, the substituent, or side chain, as a whole may be referred to as an albumin binding moiety.

In another particular embodiment the albumin binding moiety comprises a portion which is particularly relevant for the albumin binding and thereby the protraction. Such portion may accordingly be referred to as a protracting moiety. The protracting moiety may be at, or near, the opposite end of the albumin binding moiety, relative to its point of attachment to the peptide.

In a still further particular embodiment the albumin binding moiety comprises a portion in between the protracting moiety and the point of attachment to the peptide, which portion may be referred to as a linker, linker moiety, spacer, or the like. The linker may be optional, and hence in that case the albumin binding moiety may be identical to the protracting moiety.

In particular embodiments, the albumin binding moiety and/or the protracting moiety is lipophilic, and may further contain both positively and/or negatively charged moieties at physiological pH (7.4).

The albumin binding moiety, the protracting moiety, or the linker may be covalently attached to a lysine residue of the peptide by acylation. Additional or alternative conjugation chemistry includes alkylation, ester formation, or amide formation, or coupling to a cysteine residue, such as by maleimide or haloacetamide (such as bromo-/fluoro-/iodo-) coupling.

In a preferred embodiment, an active ester of the albumin binding moiety, preferably comprising a protracting moiety and a linker, is covalently linked to an amino group of a lysine residue, preferably the epsilon amino group thereof, under formation of an amide bond (this process being referred to as acylation).

Unless otherwise stated, when reference is made to an acylation of a lysine residue, it is understood to be to the epsilon-amino group thereof.

For the present purposes, the terms "albumin binding moiety", "protracting moiety", and "linker" may include the unreacted as well as the reacted forms of these molecules. Whether or not one or the other form is meant is clear from the context in which the term is used.

In particular embodiments the protracting moiety is selected from a) fatty diacids, and b) fatty acids.

For the attachment to the peptide, the acid group of the fatty acid, or one of the acid groups of the fatty diacid, forms an amide bond with the epsilon amino group of a lysine residue in the peptide, preferably via a linker.

The term "fatty acid" refers to aliphatic monocarboxylic acids having from 4 to 28, preferably from 10 to 22, carbon atoms, it is preferably unbranched, and it may be saturated or unsaturated.

The term "fatty diacid" refers to fatty acids as defined above but with an additional carboxylic acid group in the omega position. Thus, fatty diacids are dicarboxylic acids.

The fatty diacids may have a terminal, or distal, phenyl or phenoxy group of which the phenyl and the phenoxy groups may be substituted.

A non-limiting example of a protracting moiety is Chem. 3: HOOC—$C_6H_4$—O—$(CH_2)_9$—CO—*; wherein preferably the HOOC-group is in the para position. Here the terminal phenoxy group of the diacid protractor is substituted with a carboxylic acid group.

Another non-limiting example of a protracting moiety is Chem. 7: HOOC—$(CH_2)_{16}$—CO—*.

In a particular embodiment the albumin binding moiety, in addition to a protracting moiety, comprises a linker. The linker is between the protracting moiety and the peptide. In a further particular embodiment the linker is covalently attached to a lysine residue of the peptide by acylation, preferably to the epsilon amino group of a lysine residue in the peptide.

In a particular embodiment a first linker element is a di-radical of 8-amino-3,6-dioxaoctanic acid, that may be represented by the formula Chem. 4: Chem. 4: *—NH—$(CH_2)_2$—O—$(CH_2)_2$—O—$CH_2$—CO—*, in brief designated OEG. In another particular embodiment a second linker element is a di-radical of Glu, such as gamma-Glu, or briefly gGlu, where the gamma carboxy group of the amino acid glutamic acid is used for connection to another linker element, or to the epsilon-amino group of lysine.

The linker may include one or more first linker elements, and/or one or more second linker elements. A non-limiting example of a linker is gGlu-2×OEG. In a particular embodiment the gGlu and 2×OEG elements of the linker are interconnected via amide bonds and in the sequence indicated, the linker being connected at its free amino end (shown to the left) to the free carbonyl group of the protracting moiety, and at its free carbonyl end (shown to the right) to the epsilon amino group of a lysine residue of the peptide.

In particular embodiments, the at least one substituent is attached to the epsilon amino group of a Lys residue of the peptide at a position corresponding to at least one, respectively, of the following positions of GLP-1(8-37): 18, 26, 27, 31, and/or 37.

In a particular embodiment, the GLP-1 peptide has one substituent, e.g. attached to position 26 or 27, wherein the position numbering refers to GLP-1(8-37).

In another particular embodiment, the GLP-1 peptide has two substituents. A GLP-1 peptide with two substituents including protracting moieties of the acid type described above may be designated di-acylated GLP-1 derivatives.

In further particular embodiments the two substituents are attached to positions corresponding to positions a) 18 and 31, b) 26 and 37, or c) 18 and 26, wherein the position numbering refers to GLP-1(8-37).

In still further particular embodiments:

a) a first substituent is attached to a position corresponding to position 18 of GLP-1(8-37) and a second substituent is attached to a position corresponding to position 31 of GLP-1(8-37); b) a first substituent is attached to a position corresponding to position 26 of GLP-1(8-37) and a second substituent is attached to a position corresponding to position 37 of GLP-1(8-37); or c) a first substituent is attached to a position corresponding to position 18 of GLP-1(8-37) and a second substituent is attached to a position corresponding to position 26 of GLP-1(8-37); wherein each of the first and the second substituent, independently, is a substituent as defined in any of the embodiments herein. The first and the second substituent are preferably similar, substantially similar, or identical.

In the context of chemical compounds such as the albumin binding moieties, protracting moieties, and linkers, similarity and/or identity may be determined using any suitable computer program and/or algorithm known in the art.

For example, the similarity of two protracting moieties, two linkers, and/or two entire side chains may suitably be determined using molecular fingerprints. Fingerprints is a mathematical method of representing a chemical structure (see e.g. Chemoinformatics: A textbook, Johann Gasteiger and Thomas Engel (Eds), Wiley-VCH Verlag, 2003). Examples of suitable fingerprints include, without limitation, UNITY fingerprints, MDL fingerprints, and/or ECFP fingerprints, such as ECFP_6 fingerprints (ECFP stands for extended-connectivity fingerprints).

In particular embodiments, the two protracting moieties, the two linkers, and/or the two entire side chains are represented as a) ECFP_6 fingerprints; b) UNITY fingerprints; and/or c) MDL fingerprints.

The Tanimoto coefficient is preferably used for calculating the similarity of the two fingerprints, whether a), b), or c) is used.

In particular embodiments, whether a), b) or c) is used, the two protracting moieties, the two linkers, and/or the two entire side chains, respectively, have a similarity of at least 0.5 (50%); preferably at least 0.6 (60%); more preferably at least 0.7 (70%), or at least 0.8 (80%); even more preferably at least 0.9 (90%); or most preferably at least 0.99 (99%), such as a similarity of 1.0 (100%).

UNITY fingerprints may be calculated using the programme SYBYL (available from Tripos, 1699 South Hanley Road, St. Louis, Mo. 63144-2319 USA). ECFP_6 and MDL fingerprints may be calculated using the programme Pipeline Pilot (available from Accelrys Inc., 10188 Telesis Court, Suite 100, San Diego, Calif. 92121, USA).

For more details, see for example J. Chem. Inf. Model. 2008, 48, 542-549; J. Chem. Inf. Comput. Sci. 2004, 44, 170-178; J. Med. Chem. 2004, 47, 2743-2749; J. Chem. Inf. Model. 2010, 50, 742-754; as well as SciTegic Pipeline Pilot Chemistry Collection: Basic Chemistry User Guide, March 2008, SciTegic Pipeline Pilot Data Modeling Collection, 2008-both from Accelrys Software Inc., San Diego, US, and the guides http://www.tripos.com/tripos_resources/fileroot/pdfs/Unity_111408.pdf, and http://www.tripos.com/data/SYBYL/SYBYL_072505.pdf.

An example of a similarity calculation is inserted hereinbelow, in which a side chain consisting of a protracting moiety in the form of a C14 fatty diacid and a gGlu-2×OEG linker (Chem. 5) is compared with a methyl ester thereof, viz. the mono methyl ester of the glutamic acid linker moiety (Chem 6):

The compounds disclosed herein (prodrugs, parent drugs, intermediate dipeptide compounds, GLP-1 peptides, GLP-1 analogues, GLP-1 derivatives) may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed compounds.

The concentration in plasma of the compounds of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent

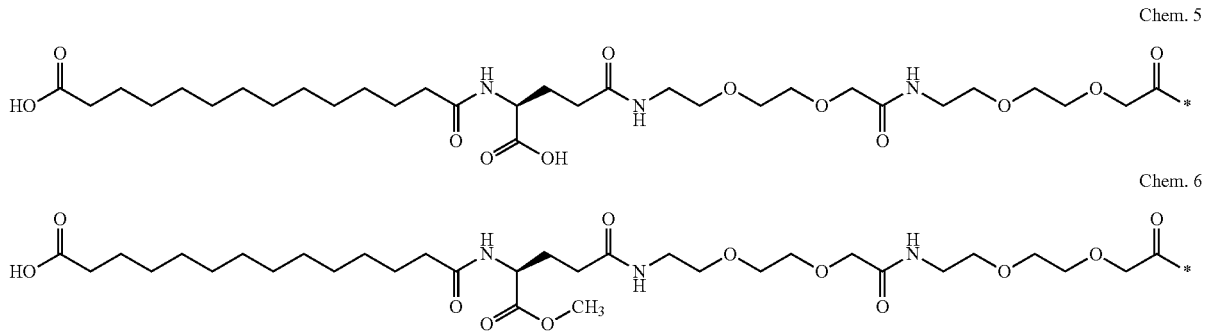

Chem. 5

Chem. 6

Using a) ECFP_6 fingerprints the similarity is 0.798, using b) UNITY fingerprints the similarity is 0.957; and using MDL fingerprints the similarity is 0.905.

In case of two identical side chains (albumin binding moieties) the derivative may be designated symmetrical.

In particular embodiments, the similarity coefficient is at least 0.80, preferably at least 0.85, more preferably at least 0.90, even more preferably at least 0.95, or most preferably at least 0.99.

In a second aspect, the present invention relates to the parent GLP-1 peptide drug corresponding to the GLP-1 peptide prodrug compound of the first aspect of the invention. In a particular embodiment the parent GLP-1 peptide drug comprises any one or more of the compounds of Chem. 21, Chem. 22, Chem. 23, Chem. 24, and/or Chem. 25, all of which are GLP-1 compounds of the formula II: (HOHis)-(GLP-1 peptide) (Formula II), wherein (HOHis), the bond, and (GLP-1 peptide) are as defined in any of the above embodiments (relating to the prodrug, the first aspect); or a pharmaceutically acceptable salt, amide or ester thereof.

In another particular embodiment the parent GLP-1 peptide drug is the desired product of the reaction where the alkylated amine nucleophile of R1-(NHXaa1) of formula I cleaves the ester bond between Xaa2 and (OHis) in formula I, resulting in the formation of the corresponding diketopiperazine derivative (as a side product) and the parent GLP-1 peptide drug as the desired product.

In a third aspect the invention relates to Boc-NMe-Ile-Val-OH (Chem. 41), Boc-NMe-Val-Val-OH (Chem. 42), Boc-NMe-Gly-Val-OH (Chem. 44), as well as the compound of Chem. 43. These are intermediate dipeptide compounds used in the synthesis of the prodrugs of the invention.

Assay), and LOCI (Luminescence Oxygen Channeling Immunoassay). General protocols for suitable RIA and ELISA assays are found in, e.g., WO09/030738 on p. 116-118. A preferred assay is the LOCI assay described in Example 52, 55, and 58 of WO 2011/080103.

Pharmaceutically Acceptable Salt, Amide, or Ester

The compounds of the invention may be in the form of a pharmaceutically acceptable salt, amide, or ester.

Salts are e.g. formed by a chemical reaction between a base and an acid, e.g.: $2NH_3+H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

Salts may be formed with added cations or anions between anionic or cationic groups, respectively. These groups may be situated in the GLP-1 peptide moiety (in the peptide part thereof, and/or in the side chain of a GLP-1 derivative, if relevant), and/or in the small peptide extension part, such as in the (R1-(NHXaa1)-Xaa2) part of formula I.

Non-limiting examples of anionic groups include free carboxylic groups. For example, the peptide often includes a free carboxylic acid group at the C-terminus, and it may also include free carboxylic groups at internal acid amino acid residues such as Asp and Glu.

Non-limiting examples of cationic groups include the free amino group at the N-terminus of the peptide, if present, as well as any free amino group of internal basic amino acid residues such as His, Arg, and Lys.

An ester may, e.g., be formed by the reaction of a free carboxylic acid group with an alcohol or a phenol, which leads to replacement of at least one hydroxyl group by an alkoxy or aryloxy group The ester formation may involve the free carboxylic group at the C-terminus of the peptide, and/or any free carboxylic group in the side chain.

An amide may, e.g., be formed by the reaction of a free carboxylic acid group with an amine or a substituted amine, or by reaction of a free or substituted amino group with a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In a particular embodiment, any of the compounds of the invention is in the form of a pharmaceutically acceptable salt. In another particular embodiment, any of the compounds of the invention is in the form of a pharmaceutically acceptable amide, preferably with an amide group at the C-terminus of the peptide. In a still further particular embodiment, any of the compounds of the invention is in the form a pharmaceutically acceptable ester.

Functional Properties

In a first functional aspect the GLP-1 prodrug compound causes a sustained release of the corresponding parent drug and thereby an extended duration of action of the parent drug, and as a result an improved half-life of the parent drug may be measured. Preferably the PK profile of the parent drug has a desirable bell-shaped form.

Also or alternatively in a second functional aspect the GLP-1 parent drug corresponding to the GLP-1 prodrug is biologically active, i.e. has GLP-1 activity.

Also or alternatively, in a third functional aspect, the GLP-1 parent drug corresponding to the GLP-1 prodrug is stabilised against degradation by DPP-IV.

Also or alternatively, in a fourth functional aspect, the GLP-1 parent drug corresponding to the GLP-1 prodrug has an extended half-life.

These properties are of importance in the development of alternative and/or next generation GLP-1 compounds for subcutaneous, intravenous, and/or in particular oral administration.

According to the first functional aspect the GLP-1 prodrug compound of the invention has an improved half-life. In a particular embodiment, the half-life of a prodrug of the invention is improved as compared to a corresponding prodrug without N-alkylation of the N-terminal amino acid of the dipeptide extension.

Also or alternatively, in a still further particular embodiment the half-life of the GLP-1 prodrug of the invention may be compared with the half-life of a corresponding comparative GLP-1 prodrug in which R1 in formula I is H.

Also or alternatively, the half-life may be determined in vitro, and/or or in vivo, using any method known in the art. A suitable test is the in vitro half-life test of Example 7 herein. In a particular embodiment of the Example 7 test the half-life is determined in phosphate buffer (pH 7.4). Also or alternatively, in another particular embodiment, the half-life is determined in plasma. Also or alternatively, in a still further particular embodiment, the prodrug of the invention has a half-life determined using the in vitro methods (buffer, and/or plasma) of example 7 which is at least twice the half-life of the comparative compound referred to above. A suitable in vivo test is included in Example 12 herein.

Biological Activity—In Vitro Potency

According to the second functional aspect the GLP-1 parent drug corresponding to the GLP-1 prodrug of the invention is biologically active, i.e. has GLP-1 activity. As is explained above, the GLP-1 parent drug is the drug expected to result from the transformation in vivo of the GLP-1 prodrug of the invention.

The term GLP-1 activity refers to the ability to bind to the GLP-1 receptor and initiate a signal transduction pathway resulting in insulinotropic action or other physiological effects as is known in the art. GLP-1 activity may be determined using any method known in the art. In particular embodiments, the in vitro potency tests of Examples 8 and/or 9 herein may be used for determining GLP-1 activity.

Biological Activity—In Vivo Pharmacology

Also, or alternatively, the potency may be determined in vivo, as is known in the art, in any suitable animal model, as well as in clinical trials. The diabetic db/db mouse is one example of a suitable animal model, and the blood glucose lowering effect may be determined in such mice in vivo, e.g. as described in Example 43 of WO09/030738.

Biological Activity—In Vitro Potency and Receptor Binding

In a particular embodiment, potency and/or activity refers to in vitro potency, i.e. performance in a functional GLP-1 receptor assay, more in particular to the capability of stimulating cAMP formation in a cell line expressing the cloned human GLP-1 receptor.

The stimulation of the formation of cAMP in a medium containing the human GLP-1 receptor may preferably be determined using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 8.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the compounds of the invention, in particular the potency of the GLP-1 parent drug, may be determined as described above, and the $EC_{50}$ of the compound in question determined. The lower the $EC_{50}$, the better the potency.

In a particular embodiment, the medium has the following composition (final in-assay concentrations): 50 mM TRIS-HCl; 5 mM HEPES; 10 mM $MgCl_2$, $6H_2O$; 150 mM NaCl; 0.01% Tween; 0.1% BSA; 0.5 mM IBMX; 1 mM ATP; 1 µM GTP; pH 7.4.

In a further particular embodiment, the GLP-1 parent drug has an in vitro potency corresponding to an $EC_{50}$ at or below 3000 pM, more preferably below 2000 pM, even more preferably below 1000 pM, or most preferably below 500 pM. Or the parent drug may have an in vitro potency corresponding to an $EC_{50}$ at or below 300 pM, preferably below 250 pM, more preferably below 200 pM, even more preferably below 150 pM, or most preferably below 100 pM.

An alternative equally useful in vitro potency assay is described in Example 9. In this assay, the parent drug may have an in vitro potency corresponding to an $EC_{50}$ at or below 100 pM, preferably below 50 pM, more preferably below 40 pM, even more preferably below 35 pM, or most preferably below 30 pM; or below 25 pM, preferably below 20 pM, more preferably below 15 pM, even more preferably below 10 pM, or most preferably below 5 pM.

In another particular embodiment, also or alternatively, potency and/or activity refers to the ability of the compounds of the invention, in particular the GLP-1 parent drug, to bind to the GLP-1 receptor in the presence of a low concentration of albumin, which may be determined as described in Example 10.

Generally, the binding to the GLP-1 receptor at low albumin concentration should be as good as possible, corresponding to a low $IC_{50}$ value.

In a particular embodiment, the GLP-1 receptor binding affinity ($IC_{50}$) in the presence of 0.005% HSA (low albumin) is below 1000.00 nM, preferably below 600.00 nM, more preferably below 100.00 nM, or most preferably below 50.00 nM.

Biological Activity—Stabilised Against Degradation by DPP-IV

According to the third functional aspect the GLP-1 parent drug corresponding to the GLP-1 prodrug of the invention is stabilised against degradation by DPP-IV.

Resistance of peptide compounds to degradation by dipeptidyl aminopeptidase IV (DPP-IV) may be determined using any method known in the art.

An example of a suitable assay is the following degradation assay: Aliquots of the peptides are incubated at 37° C. with an aliquot of purified dipeptidyl aminopeptidase IV for 4-22 hours in an appropriate buffer at pH 7-8 (buffer not being albumin). Enzymatic reactions are terminated by the addition of trifluoroacetic acid, and the peptide degradation products are separated and quantified using HPLC or LC-MS analysis. One method for performing this analysis is: The mixtures are applied onto a Zorbax 300SB-C18 (30 nm pores, 5 µm particles) 150×2.1 mm column and eluted at a flow rate of 0.5 ml/min with a linear gradient of acetonitrile in 0.1% trifluoroacetic acid (0%-100% acetonitrile over 30 min). Peptides and their degradation products may be monitored by their absorbance at 214 nm (peptide bonds) or 280 nm (aromatic amino acids), and are quantified by integration of their peak areas. The degradation pattern can be determined by using LC-MS where MS spectra of the separated peak can be determined. Percentage intact/degraded compound at a given time is used for estimation of the peptides DPP-IV stability.

Also or alternatively DPP-IV degradation can be determined as described in Example 11 herein.

A peptide compound may, for example, be defined as DPP-IV stabilised when it is 10 times more stable than the natural peptide based on percentage intact compound at a given time. In a particular embodiment, a GLP-1 compound may be said to be DPP-IV stabilised when it is at least 10 times more stable than GLP-1(7-37) (SEQ ID NO: 1 extended by an N-terminal His at position 7).

Pharmacokinetics Profile

According to the first and fourth functional aspect the release of the GLP-1 parent drug from the GLP-1 prodrug of the invention is sustained. Thereby an extended duration of action of the parent drug is achieved, and as a result an improved half-life of the parent drug may be measured. Preferably the PK profile of the parent drug has a desirable bell-shaped form. Sustained release or extended duration of action may also be referred to a prolonged duration of action, and/or a protracted effect. This may be determined using any method known in the art, in vitro, and/or in vivo. In one particular embodiment the half-life ($T_{1/2}$) is determined in vivo in rats after i.v. administration, for example using the method described in Example 58 of WO 2011/080103. Also, or alternatively, in another particular embodiment, protraction may be determined as half-life ($T_{1/2}$) in vivo in minipigs after i.v. administration, for example using the method described in Example 54 of WO 2011/080103. The prodrugs of the invention may also be tested using these methods. In still further particular embodiments, also or alternatively, the prodrugs of the invention also have an extended half-life in vivo. This may for example be determined using any method referred to hereinabove. In a particular embodiment comparison may be made with the corresponding prodrug in which R1 is H. A preferred test is the minipig i.v. PK experiment described in Example 12 herein.

Production Processes

The production of the constituent GLP-1 peptides of the GLP-1 prodrugs and GLP-1 parent drugs of the invention, such as GLP-1(8-37) (SEQ ID NO: 1), and analogues thereof, is well known in the art.

These peptides may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

Those derivatives of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

The depsipeptide prodrugs and the constituent (HOHis)-(GLP-1 peptide) parent drugs of the invention may be prepared as is generally known in the art, for example as disclosed in the experimental part.

Pharmaceutical Compositions

Pharmaceutical compositions comprising a GLP-1 prodrug or a GLP-1 parent drug of the invention and a pharmaceutically acceptable excipient may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. $19^{th}$ edition (1995), and any later editions).

Non-limiting examples of excipients are: Solvents, diluents, buffers, preservatives, tonicity regulating agents, chelating agents, and stabilisers.

Examples of formulations include liquid formulations, i.e. aqueous formulations comprising water. A liquid formulation may be a solution, or a suspension. An aqueous formulation typically comprises at least 50% w/w water, or at least 60%, 70%, 80%, or even at least 90% w/w of water.

Alternatively, a pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0.

A pharmaceutical composition may comprise a buffer. The buffer may e.g. be selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, and mixtures thereof.

A pharmaceutical composition may comprise a preservative. The preservative may e.g. be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol), and mixtures thereof. The preservative may be present in a concentration from 0.1 mg/ml to 20 mg/ml. A pharmaceutical composition may comprise an isotonic agent. The isotonic agent may e.g. be selected from the group consisting of a salt (e.g. sodium chloride), a sugar or sugar alcohol, an amino acid (e.g. glycine, histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), and mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol.

A pharmaceutical composition may comprise a chelating agent. The chelating agent may e.g. be selected from salts of ethylenediaminetetraacetic acid (EDTA), citric acid, and aspartic acid, and mixtures thereof.

A pharmaceutical composition may comprise a stabiliser. The stabiliser may e.g. be one or more oxidation inhibitors, aggregation inhibitors, surfactants, and/or one or more protease inhibitors. Non-limiting examples of these various kinds of stabilisers are disclosed in the following.

The term "aggregate formation" refers to a physical interaction between the peptide molecules resulting in formation of oligomers, which may remain soluble, or large visible aggregates that precipitate from the solution. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

A pharmaceutical composition may comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present.

Methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. Any stereoisomer of methionine (L or D) or combinations thereof can be used.

A pharmaceutical composition may comprise a stabiliser selected from the group of high molecular weight polymers or low molecular compounds. The stabiliser may e.g. be selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). A pharmaceutical composition may comprise additional stabilising agents such as, but not limited to, methionine and EDTA, which protect the polypeptide against methionine oxidation, and a nonionic surfactant, which protects the polypeptide against aggregation associated with freeze-thawing or mechanical shearing.

A pharmaceutical composition may comprise one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant may e.g. be selected from the group consisting of anionic surfactants, cationic surfactants, nonionic surfactants, and/or zwitterionic surfactants.

A pharmaceutical composition may comprise one or more protease inhibitors, such as, e.g., EDTA (ethylenediamine tetraacetic acid), and/or benzamidine HCl.

Additional, optional, ingredients of a pharmaceutical composition include, e.g., wetting agents, emulsifiers, antioxidants, bulking agents, metal ions, oily vehicles, proteins (e.g., human serum albumin, gelatine), and/or a zwitterion (e.g., an amino acid such as betaine, taurine, arginine, glycine, lysine and histidine).

Still further, a pharmaceutical composition may be formulated as is known in the art of oral formulations of insulinotropic compounds, e.g. using any one or more of the formulations described in WO 2008/145728.

An administered dose may contain from 0.01 mg-100 mg of the prodrug or drug, respectively, or from 0.01-50 mg, or from 0.01-20 mg, or from 0.01-10 mg of the prodrug, or drug, respectively.

The derivative may be administered in the form of a pharmaceutical composition. It may be administered to a patient in need thereof at several sites, for example, at topical sites such as skin or mucosal sites; at sites which bypass absorption such as in an artery, in a vein, or in the heart; and at sites which involve absorption, such as in the skin, under the skin, in a muscle, or in the abdomen.

The route of administration may be, for example, lingual; sublingual; buccal; in the mouth; oral; in the stomach; in the intestine; nasal; pulmonary, such as through the bronchioles, the alveoli, or a combination thereof; parenteral, epidermal; dermal; transdermal; conjunctival; uretal; vaginal; rectal;

and/or ocular. A composition may be an oral composition, and the route of administration is per oral.

A composition may be administered in several dosage forms, for example as a solution; a suspension; an emulsion; a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant.

A composition may be a tablet, optionally coated, a capsule, or a chewing gum.

A composition may further be compounded in a drug carrier or drug delivery system, e.g. in order to improve stability, bioavailability, and/or solubility. In a particular embodiment a composition may be attached to such system through covalent, hydrophobic, and/or electrostatic interactions. The purpose of such compounding may be, e.g., to decrease adverse effects, achieve chronotherapy, and/or increase patient compliance.

A composition may also be used in the formulation of controlled, sustained, protracting, retarded, and/or slow release drug delivery systems.

Parenteral administration may be performed by subcutaneous, intramuscular, intraperitoneal, or intravenous injection by means of a syringe, optionally a pen-like syringe, or by means of an infusion pump.

A composition may be administered nasally in the form of a solution, a suspension, or a powder; or it may be administered pulmonally in the form of a liquid or powder spray.

Transdermal administration is a still further option, e.g. by needle-free injection, from a patch such as an iontophoretic patch, or via a transmucosal route, e.g. buccally.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

The treatment with a derivative according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity.

Pharmaceutical Indications

The present invention also relates to the GLP-1 prodrug of the invention, as well as the GLP-1 parent drug of the invention, for use as a medicament.

In particular embodiments, they may be used for the following medical treatments, all preferably relating one way or the other to diabetes:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying;

(vi) prevention and/or treatment of diabetic complications, such as neuropathy, including peripheral neuropathy; nephropathy; or retinopathy;

(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;

(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atheroschlerosis; mild chronic heart failure; angina pectoris; cardiac bypass reocclusion; intermittent claudication (atheroschlerosis obliterens); diastolic dysfunction; and/or systolic dysfunction;

(ix) prevention and/or treatment of gastrointestinal diseases, such as inflammatory bowel syndrome; small bowel syndrome, or Crohn's disease; dyspepsia; and/or gastric ulcers;

(x) prevention and/or treatment of critical illness, such as treatment of a critically ill patient, a critical illness polynephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or (xi) prevention and/or treatment of polycystic ovary syndrome (PCOS).

In a particular embodiment, the indication is selected from the group consisting of (i)-(iii) and (v)-(iix), such as indications (i), (ii), and/or (iii); or indication (v), indication (vi), indication (vii), and/or indication (iix).

In another particular embodiment, the indication is (i). In a further particular embodiment the indication is (v). In a still further particular embodiment the indication is (iix).

The following indications are particularly preferred: Type 2 diabetes, and/or obesity.

Particular Embodiments

The following are particular embodiments of the invention:

1. A GLP-1 compound of the general formula I:

R1-(NHXaa1)-Xaa2-(OHis)-(GLP-1 peptide)    (Formula I)

wherein
GLP-1 peptide is GLP-1(8-37) (SEQ ID NO: 1) or an analogue thereof having a maximum of nine amino acid changes as compared to GLP-1(8-37) (SEQ ID NO: 1);
R1 is lower alkyl;
(NHXaa1) is an amino acid;
Xaa2 is an amino acid; and
(OHis) is a radical of imidazole-lactic acid of formula Chem. 1:

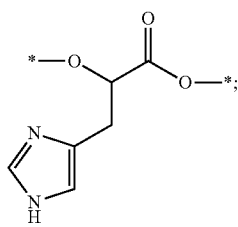

Chem. 1 or a pharmaceutically acceptable salt, amide, or ester thereof.

2. The compound of embodiment 1, which is a GLP-1 prodrug.
3. The compound of any of embodiments 1 and 2, which is a GLP-1 ester prodrug.
4. The compound of any of embodiments 1-3, which is a GLP-1 depsipeptide.
5. The compound of any of embodiments 1-4, wherein the bond between Xaa2 and (OHis) is an ester bond.
6. The compound of any of embodiments 1-5, wherein the bond between (NHXaa1) and Xaa2 is an amide bond.
7. The compound of any of embodiments 1-6, wherein the bond between (OHis) and (GLP-1 peptide) is an amide bond.
8. The compound of any of embodiments 1-7, wherein R1 is attached to the alpha-amino group of (NHXaa1).
9. The compound of any of embodiments 1-8, which is an N-terminally extended GLP-1 peptide.
10. The compound of any of embodiment 1-9, wherein R1 has from one to six carbon atoms.
11. The compound of any of embodiments 1-10, wherein R1 is straight alkyl.
12. The compound of any of embodiments 1-10, wherein R1 is branched alkyl.
13. The compound of any of embodiments 1-11, wherein R1 is methyl.
14. The compound of any of embodiments 1-13, wherein (NHXaa1) is Gly, Val, or Ile.
15. The compound of any of embodiments 1-14, wherein (NHXaa1) is Gly.
16. The compound of any of embodiments 1-14, wherein (NHXaa1) is Val.
17. The compound of any of embodiments 1-14, wherein (NHXaa1) is Ile.
18. The compound of any of embodiments 1-17, wherein Xaa2 does not comprise an N-alkylated amino acid.
19. The compound of any of embodiments 1-18, wherein Xaa2 is a proteinogenic amino acid.
20. The compound of any of embodiments 1-19, wherein Xaa2 is a beta-branched amino acid.
21. The compound of any of embodiments 1-20, wherein Xaa2 is Val.
22. The compound of any of embodiments 1-21, wherein (OHis) has the formula of Chem. 2, and/or the name of L-beta-imidazole lactic acid or (2S)-2-Hydroxy-3-(1H-imidazole-4-yl)propionic acid:

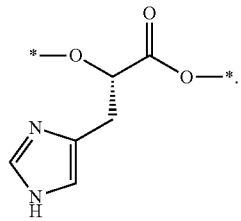

Chem. 2

23. The compound of any of embodiments 1-22, wherein (OHis) is attached to the N-terminus of the GLP-1 peptide.
24. The compound of any of embodiments)-23, wherein the GLP-1 peptide is GLP-1(8-37) (SEQ ID NO: 1).
25. The compound of any of embodiments)-23, wherein the GLP-1 peptide is an analogue of GLP-1(8-37) (SEQ ID NO: 1).
26. The compound of embodiment 25, wherein the analogue has a maximum of eight, preferably seven, amino acid changes as compared to GLP-1(8-37) (SEQ ID NO: 1).
27. The compound of any of embodiments 25-26, wherein the analogue has a maximum of 6 amino acid changes as compared to GLP-1(8-37) (SEQ ID NO: 1).
28. The compound of any of embodiments 25-27, wherein the analogue has a maximum of 5 amino acid changes as compared to GLP-1(8-37) (SEQ ID NO: 1).
29. The compound of any of embodiments 25-28, wherein the analogue has a maximum of 4 amino acid changes as compared to GLP-1(8-37) (SEQ ID NO: 1).
30. The compound of any of embodiments 25-29, wherein the analogue has a maximum of 3 amino acid changes as compared to GLP-1(8-37) (SEQ ID NO: 1).
31. The compound of any of embodiments 25-30, wherein the analogue has a maximum of 2 amino acid changes as compared to GLP-1(8-37) (SEQ ID NO: 1).
32. The compound of any of embodiments 25-31, wherein the analogue has a maximum of 1 amino acid change as compared to GLP-1(8-37) (SEQ ID NO: 1).

33. The compound of any of embodiments 25-32, wherein the analogue has a minimum of 1 amino acid changes as compared to GLP-1(8-37) (SEQ ID NO: 1).
34. The compound of any of embodiments 25-33, wherein the analogue has a minimum of 2 amino acid changes as compared to GLP-1(8-37) (SEQ ID NO: 1).
35. The compound of any of embodiments 25-34, wherein the analogue has a minimum of 3 amino acid changes as compared to GLP-1(8-37) (SEQ ID NO: 1).
36. The compound of any of embodiments 25-35, wherein the analogue has a minimum of 4 amino acid changes as compared to GLP-1(8-37) (SEQ ID NO: 1).
37. The compound of any of embodiments 25-36, wherein the analogue has a minimum of 5 amino acid changes as compared to GLP-1(8-37) (SEQ ID NO: 1).
38. The compound of any of embodiments 25-37, wherein the analogue has a minimum of 6 amino acid changes as compared to GLP-1(8-37) (SEQ ID NO: 1).
39. The compound of any of embodiments 25-38, wherein the analogue has a minimum of 7 amino acid changes as compared to GLP-1(8-37) (SEQ ID NO: 1).
40. The compound of any of embodiments 25-39, wherein the analogue has a minimum of 8 amino acid changes as compared to GLP-1(8-37) (SEQ ID NO: 1).
41. The compound of any of embodiments 1-40, wherein the GLP-1 peptide a) comprises a peptide of Formula III; and/or b) is a peptide of Formula III, optionally derivatised:

```
Formula III:
Xaa8-Glu-Gly-Thr-Xaa12-Thr-Ser-Asp-Xaa16-Ser-

Xaa18-Xaa19-Xaa20-Glu-Xaa22-Xaa23-Ala-Xaa25-

Xaa26-Xaa27-Phe-Ile-Xaa30-Xaa31-Leu-Xaa33-Xaa34-

Xaa35-Xaa36-Lys-Xaa38,
```
wherein
Xaa$_8$ is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
Xaa$_{12}$ is Phe or Leu;
Xaa$_{16}$ is Val or Leu;
Xaa$_{18}$ is Ser, Val, Lys, or Leu;
Xaa$_{19}$ is Tyr or Gln;
Xaa$_{20}$ is Leu or Met;
Xaa$_{22}$ is Gly, Glu, or Aib;
Xaa$_{23}$ is Gln, Glu, or Arg;
Xaa$_{25}$ is Ala or Val;
Xaa$_{26}$ is Lys or Arg;
Xaa$_{27}$ is Lys, Glu, or Leu;
Xaa$_{30}$ is Ala, Glu, or Arg;
Xaa$_{31}$ is Trp, Lys, or His;
Xaa$_{33}$ is Val;
Xaa$_{34}$ is Glu, Asn, Gly, Gln, Arg, or His;
Xaa$_{35}$ is Gly or Aib;
Xaa$_{36}$ is Arg or Gly; and
Xaa$_{37}$ is Lys, Arg, or Gly; and
Xaa$_{38}$ is Ser, Gly, Ala, Glu, Pro, Arg, or absent.
42. The compound of any of embodiments 1-41, wherein the GLP-1 peptide comprises, or has, only one or two Lys.
43. The compound of any of embodiments 41-42, wherein Xaa$_8$ is Ala or Aib; Xaa$_{12}$ is Phe; Xaa$_{16}$ is Val; Xaa$_{18}$ is Ser or Lys; Xaa$_{19}$ is Tyr; Xaa$_{20}$ is Leu; Xaa$_{22}$ is Gly or Glu; Xaa$_{23}$ is Gln or Arg; Xaa$_{25}$ is Ala or Val; Xaa$_{26}$ is Lys or Arg; Xaa$_{27}$ is Lys or Glu; Xaa$_{30}$ is Ala; Xaa$_{31}$ is Trp or Lys; Xaa$_{33}$ is Val; Xaa$_{34}$ is Gln or Arg; Xaa$_{35}$ is Gly; Xaa$_{36}$ is Arg; Xaa$_{37}$ is Lys or Gly; and Xaa$_{38}$ is absent.
44. The compound of any of embodiments 41-43, wherein Xaa$_8$ is Ala.
45. The compound of any of embodiments 41-43, wherein Xaa$_8$ is Aib.
46. The compound of any of embodiments 41-45, wherein Xaa$_{12}$ is Phe.
47. The compound of any of embodiments 41-46, wherein Xaa$_{16}$ is Val.
48. The compound of any of embodiments 41-47, wherein Xaa$_{18}$ is Ser.
49. The compound of any of embodiments 41-47, wherein Xaa$_{18}$ is Lys.
50. The compound of any of embodiments 41-49, wherein Xaa$_{19}$ is Tyr.
51. The compound of any of embodiments 41-50, wherein Xaa$_{20}$ is Leu.
52. The compound of any of embodiments 41-51, wherein Xaa$_{22}$ is Gly.
53. The compound of any of embodiments 41-51, wherein Xaa$_{22}$ is Glu.
54. The compound of any of embodiments 41-53, wherein Xaa$_{23}$ is Gln.
55. The compound of any of embodiments 41-53, wherein Xaa$_{23}$ is Arg.
56. The compound of any of embodiments 41-55, wherein Xaa$_{25}$ is Ala.
57. The compound of any of embodiments 41-55, wherein Xaa$_{25}$ is Val.
58. The compound of any of embodiments 41-57, wherein Xaa$_{26}$ is Lys.
59. The compound of any of embodiments 41-57, wherein Xaa$_{26}$ is Arg.
60. The compound of any of embodiments 41-59, wherein Xaa$_{27}$ is Glu.
61. The compound of any of embodiments 41-59, wherein Xaa$_{27}$ is Lys.
62. The compound of any of embodiments 41-61, wherein Xaa$_{30}$ is Ala.
63. The compound of any of embodiments 41-62, wherein Xaa$_{31}$ is Trp.
64. The compound of any of embodiments 41-62, wherein Xaa$_{31}$ is Lys.
65. The compound of any of embodiments 41-64, wherein Xaa$_{33}$ is Val.
66. The compound of any of embodiments 41-65, wherein Xaa$_{34}$ is Gln.
67. The compound of any of embodiments 41-65, wherein Xaa$_{34}$ is Arg.
68. The compound of any of embodiments 41-68, wherein Xaa$_{35}$ is Gly.
69. The compound of any of embodiments 41-68, wherein Xaa$_{36}$ is Arg.
70. The compound of any of embodiments 41-69, wherein Xaa$_{37}$ is Gly.
71. The compound of any of embodiments 41-69, wherein Xaa$_{37}$ is Lys.
72. The compound of any of embodiments 41-71, wherein Xaa$_{38}$ is absent.
73. The compound of any of embodiments 25-72, wherein the analogue, when compared to GLP-1(8-37) (SEQ ID NO: 1), comprises at least one amino acid substitution selected from the following: 8Aib, 18K, 22E, 23R, 25V, 26R, 27K, 31K, 34R or 34Q, and/or 37K, wherein the position numbering refers to GLP-1(8-37) (SEQ ID NO: 1).

74. The compound of any of embodiments 25-73, wherein the analogue is the variant (18K, 22E, 25V, 26R, 31K, 34R) of GLP-1(8-37) (SEQ ID NO: 1).
75. The compound of any of embodiments 25-73, wherein the analogue is the variant (34R, 37K) of GLP-1(8-37) (SEQ ID NO: 1).
76. The compound of any of embodiments 25-73, wherein the analogue is the variant (18K, 22E, 34Q) of GLP-1(8-37) (SEQ ID NO: 1).
77. The compound of any of embodiments 25-73, wherein the analogue is the variant (8Aib, 22E, 26R, 27K, 34R) of GLP-1(8-37) (SEQ ID NO: 1).
78. The compound of any of embodiments 25-73, wherein the analogue is the variant (8Aib, 23R, 34R) of GLP-1(8-37) (SEQ ID NO: 1).
79. The compound of any of embodiments 1-78, wherein GLP-1 peptide is a derivative of a) GLP-1(8-37) (SEQ ID NO: 1), or b) the analogue as defined in any of embodiments 25-77.
80. The compound of embodiment 79, wherein at least one substituent is covalently attached to the peptide defined in a) or b).
81. The compound of any of embodiments 79-80, wherein the substituent is a side chain.
82. The compound of embodiment 81, wherein the side chain is capable of forming non-covalent aggregates with albumin.
83. The compound of any of embodiments 81-82, wherein the side chain is an albumin binding moiety.
84. The compound of embodiment 83, wherein the albumin binding moiety comprises a protracting moiety and optionally a linker.
85. The compound of any of embodiments 83-84, wherein the albumin binding moiety, the protracting moiety, or the linker is covalently attached to a lysine residue of the peptide by acylation, preferably to the epsilon amino group thereof.
86. The compound of any of embodiments 84-85, wherein the protracting moiety is selected from a) fatty diacids, and b) fatty acids, optionally with a terminal, or distal, phenyl or phenoxy group, both optionally substituted.
87. The compound of embodiment 86, wherein a carboxy group of the fatty acid or fatty diacid is acylated, optionally via a linker, to a lysine residue of the peptide, preferably at the epsilon-amino group thereof.
88. The compound of any of embodiments 85-87, wherein the protracting moiety is Chem. 3: HOOC—$C_6H_4$—O—$(CH_2)_9$—CO—*; wherein preferably the HOOC-group is in the para position.
89. The compound of any of embodiments 85-87, wherein the protracting moiety is Chem. 7: HOOC—$(CH_2)_{16}$—CO—*.
90. The compound of any of embodiments 84-89, wherein the albumin binding moiety, in addition to a protracting moiety, comprises a linker.
91. The compound of embodiment 90, wherein the linker is between the protracting moiety and the peptide.
92. The compound of embodiment 91, wherein the linker is covalently attached to a lysine residue of the peptide by acylation, preferably to the epsilon amino group of a lysine residue in the peptide.
93. The compound of any of embodiments 90-92, wherein the linker includes one or more linker elements.
94. The compound of embodiment 93, wherein a first linker element is a di-radical of 8-amino-3,6-dioxaoctanic acid, that may be represented by the formula Chem. 4: Chem. 4: *—NH—$(CH_2)_2$—O—$(CH_2)_2$—O—$CH_2$—CO—*, and/or that may be designated OEG.
95. The compound of any of embodiments 93-94, wherein a second linker element is a di-radical of Glu, such as gamma-Glu, or briefly gGlu, where the gamma carboxy group of the amino acid glutamic acid is used for connection to another linker element, or to the epsilon-amino group of lysine.
96. The compound of any of embodiments 93-95, wherein the linker includes one or more first linker elements, and/or one or more second linker elements.
97. The compound of any of embodiments 90-96 wherein the linker is gGlu-2×OEG.
98. The compound of embodiment 97, wherein the alpha-amino group of gGlu forms an amide bond with the carboxy group of the protracting moiety, the gamma carboxy group of gGlu forms an amide bond with the N-terminal end of OEG, and the C-terminal end of OEG forms an amide bond with an epsilon amino group of a Lys residue in the peptide.
99. The compound of any of embodiments 80-98, wherein the at least one substituent is attached to the epsilon amino group of a Lys residue at a position corresponding to at least one, respectively, of the following positions of GLP-1(8-37) (SEQ ID NO: 1): 18, 26, 27, 31, and/or 37.
100. The compound of embodiment 99, which has one substituent attached to position 26 or 27, wherein the position numbering refers to GLP-1(8-37).
101. The compound of embodiment 99, which has one substituent attached to position 26.
102. The compound of embodiment 99, which has one substituent attached to position 27.
103. The compound of embodiment 99, which has two substituents attached to position a) 18 and 31, b) 26 and 37, or c) 18 and 26, wherein the position numbering refers to GLP-1(8-37); wherein the compound preferably has one substituent attached to a) each of positions 18 and 31, b) each of positions 26 and 37, or c) each of positions 18 and 26.
104. The compound of any of embodiments 1-103, wherein GLP-1 peptide is selected from the following:

Chem. 21a:

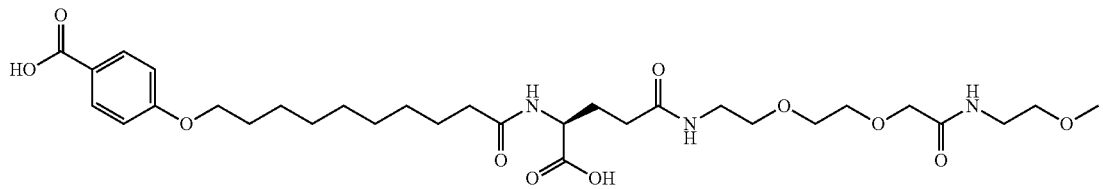

-continued
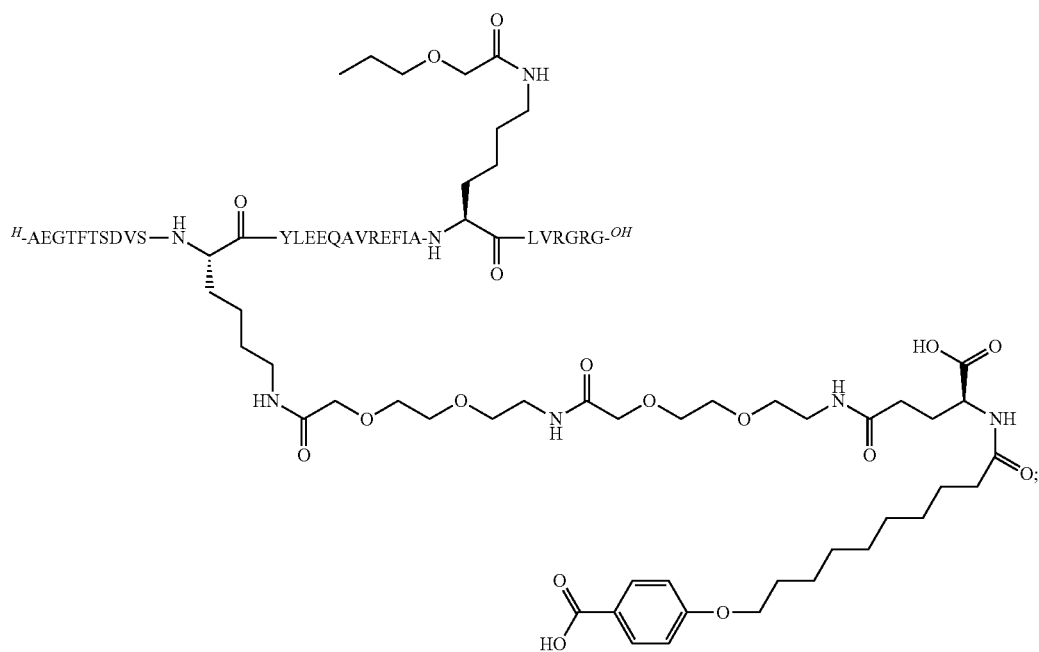
Chem. 22a:
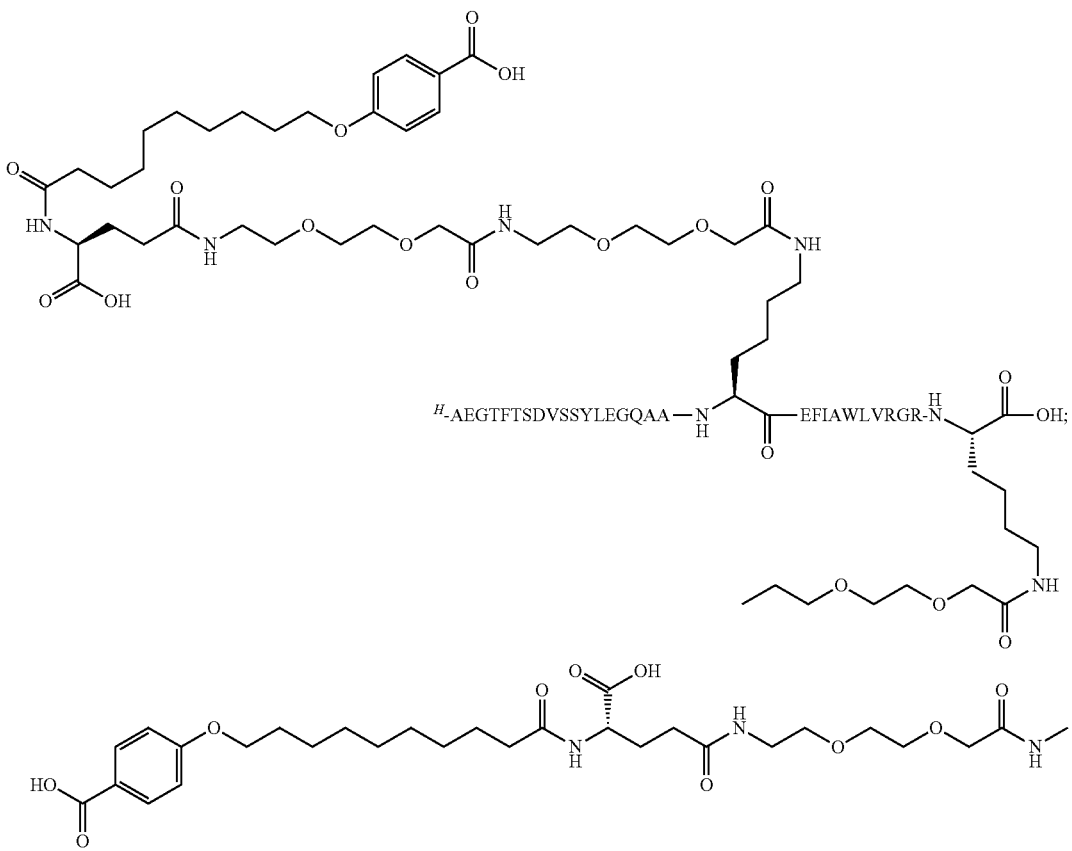

Chem. 23a:
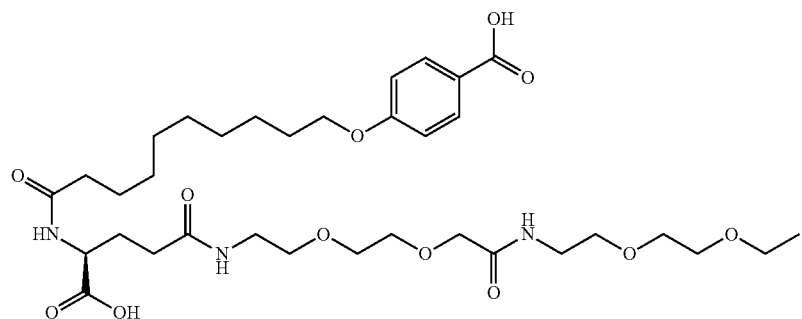
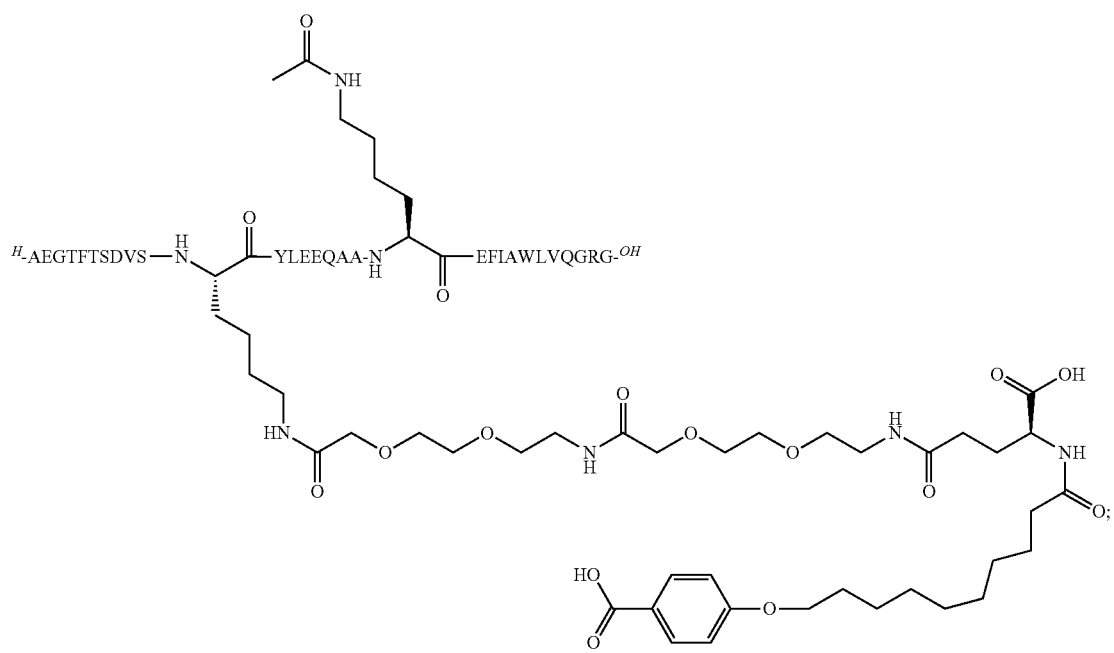
Chem. 24a:
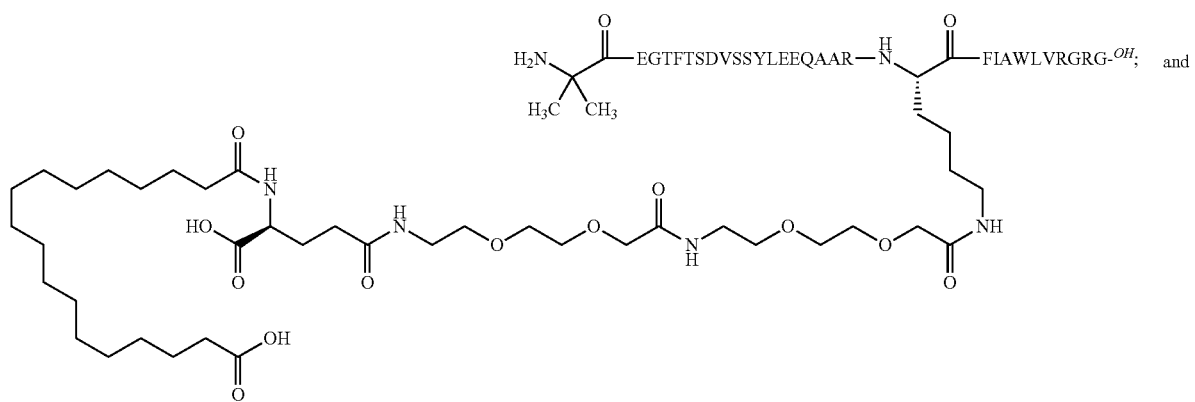

Chem. 25a:

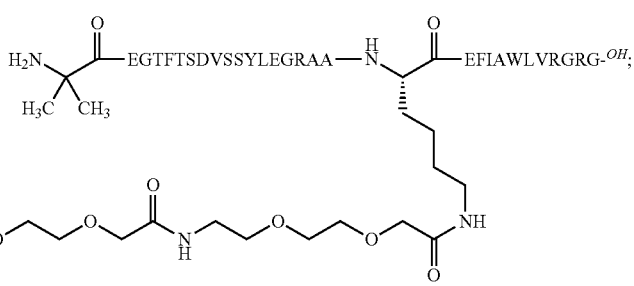
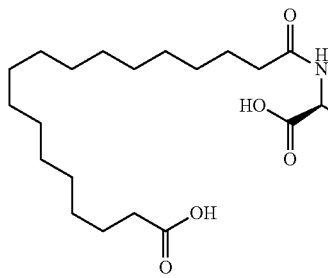

or a pharmaceutically acceptable salt, amide, or ester thereof.

105. The compound of any of embodiments 1-104 which has an extended half-life, preferably an extended half-life in vitro, or in vivo; for example as compared to the corresponding comparative compound in which R1 is H.

106. The compound of embodiment 105, wherein the in vitro prodrug half-life is measured at 37° C. in a) 25 mM phosphate buffer (pH 7.4); and/or b) a solution of 200 ul 200 mM phosphate buffer (pH 7.4) and 800 ul plasma; and wherein the concentration of the compound may be determined using any suitable method, such as UPLC.

107. The compound of embodiment 106, wherein the prodrug half-life is determined using a) the Buffer method and/or b) the Plasma method, for example generally as described in Example 7.

108. The compound of any of embodiments 105-107 which has a prodrug half-life that is at least 2 times, preferably at least 3 times, more preferably at least 4 times, even more preferably at least 5 times, or most preferably at least 6 times that of the comparative compound.

109. The compound of any of embodiments 1-108, which includes in its structure a compound element of the formula II: (HOHis)-(GLP-1 peptide) (Formula II), wherein (HOHis) is imidazole-lactic acid corresponding to the (OHis) radical of Chem 1, and the bond, and GLP-1 peptide are as defined in any of embodiments 1-108 above, which compound element of formula II has GLP-1 activity.

110. The compound of embodiment 109, wherein (HOHis) has the formula Chem. 1a:

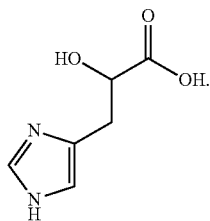

111. The compound of embodiment 109, wherein (HOHis) has the formula Chem. 2a:

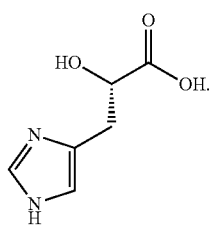 [SMILES: O=C(O)[C@@H](O)Cc1c[nH]cn1]

112. The compound of any of embodiments 109-111, wherein the compound element is a GLP-1 parent drug.

113. The compound of any of embodiments 109-112, wherein GLP-1 activity of the compound element refers to the capability of activating the human GLP-1 receptor.

114. The compound of embodiment 113, wherein activation of the human GLP-1 receptor is measured in an in vitro assay, as the potency of cAMP production.

115. The compound of any of embodiments 109-114, wherein the compound element has a potency corresponding to an $EC_{50}$ a) below 2000 pM, preferably below 1800 pM, more preferably below 1600 pM, even more preferably below 1400 pM, or most preferably below 1200 pM;

c) below 1000 pM, preferably below 800 pM, more preferably below 600 pM, even more preferably below 500 pM, or most preferably below 400 pM; or d) below 300 pM, preferably below 250 pM, more preferably below 200 pM, even more preferably below 150 pM, or most preferably below 100 pM.

116. The compound of any of embodiments 114-115, wherein the potency is determined as $EC_{50}$ for stimulation of the formation of cAMP in a medium containing the human GLP-1 receptor, preferably using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 8.

117. The compound of any of embodiments 114-116, wherein the reciprocal of (the $EC_{50}$ value of the compound element of formula II, divided by the $EC_{50}$ value of the corresponding comparative drug of the formula III:

(His7)-(GLP-1 peptide) (Formula III), wherein (His7) refers to L-His at position 7 of GLP-1(8-37) (SEQ ID NO: 1 extended by an N-terminal His), the bond is an amide bond, and the GLP-1 peptide is the same as in the compound), is at least 0.1, preferably at least 0.2, more preferably at least 0.3, even more preferably at least 0.4, or most preferably at least 0.5.

118. The compound of embodiment 113, wherein GLP-1 activity of the compound element refers to the capability of activating the human GLP-1 receptor in a whole cell assay.

119. The compound of embodiment 118, wherein the compound element has a potency corresponding to an $EC_{50}$
a) below 100 pM, preferably below 50 pM, more preferably below 40 pM, even more preferably below 35 pM, or most preferably below 30 pM; or
c) below 25 pM, preferably below 20 pM, more preferably below 15 pM, even more preferably below 10 pM, or most preferably below 5 pM.

120. The compound of any of embodiments 118-119, wherein the in vitro potency is determined by measuring the response of the human GLP-1 receptor in a reporter gene assay, which is preferably performed in a stably transfected BHK cell line that expresses the human GLP-1 receptor and contains the DNA for the cAMP response element (CRE) coupled to a promoter and the gene for firefly luciferase (CRE luciferase).

121. The compound of embodiment 120, wherein when the human GLP-1 receptor is activated it results in the production of cAMP, which in turn results in the luciferase protein being expressed, and wherein, when assay incubation is completed, the luciferase substrate (luciferin) is added and the enzyme converts luciferin to oxyluciferin to produce bioluminescence, which is the readout for the assay.

122. The compound of embodiment 121, wherein the assay is conducted as described in Example 9.

123. The compound of any of embodiments 109-122, wherein GLP-1 activity of the compound element refers to the capability of binding to the human GLP-1 receptor in the presence of low albumin.

124. The compound of embodiment 123, for which the GLP-1 receptor binding affinity ($IC_{50}$) of the compound element in the presence of 0.005% HSA (low albumin) is
a) below 1000 nM, preferably below 500 nM, more preferably below 100 nM, or most preferably below 50 nM;
b) below 40 nM, preferably below 30.0 nM, still more preferably below 20.0 nM, even more preferably below 10.0 nM, or most preferably below 5.00 nM; or
c) below 5.0 nM, preferably below 4.0 nM, still more preferably below 2.0 nM, even more preferably below 1.0 nM, or most preferably below 0.5 nM.

125. The compound of any of embodiments 123-124, wherein the binding affinity to the GLP-1 receptor is measured by way of displacement of $^{125}$I-GLP-1 from the receptor, preferably using a SPA binding assay, more preferably as described in Example 10.

126. The compound of any of embodiments 123-125, wherein the reciprocal of (the $IC_{50}$ value of the compound element of formula II divided by the $IC_{50}$ value of the corresponding comparative drug of the formula III:

(His7)-(GLP-1 peptide) (Formula III), wherein (His7) refers to L-His at position 7 of GLP-1(7-37) (SEQ ID NO: 1 extended by an N-terminal His), the bond is an amide bond, and the GLP-1 peptide is the same as in the compound), is at least 0.1, preferably at least 0.2, more preferably at least 0.3, even more preferably at least 0.4, or most preferably at least 0.5.

127. The compound of any of embodiments 109-126, wherein the compound element is stabilised against DPP-IV degradation.

128. The compound of embodiment 127, which has
a) a half-life of at least 1000 min, preferably at least 1500 min, more preferably at least 2000 min, or most preferably at least 2500 min; or
b) a half-life of at least 3000 min, or preferably at least 3500 min; determined after in vitro incubation with DPP-IV with or without addition of BSA, generally as described in Example 11.

129. The compound of any of embodiments 1-128, which when administered i.v. in minipig results in a 'bell-shaped' PK profile for the parent drug, e.g. generally as the curve represented by the squares in FIG. 2.

130. A compound selected from Chem. 51, Chem. 52, Chem. 53, Chem. 54, Chem. 55, and Chem. 56; or a pharmaceutically acceptable salt, amide or ester thereof.

131. A compound, preferably according to embodiment 80, the structure of which is selected from the structures shown in Examples 1, 2, 3, 4, 5, and 6; or a pharmaceutically acceptable salt, amide or ester thereof.

132. A compound, preferably according to any of embodiments 80 and/or 81, the name of which is selected from the names of the compounds of Examples 1, 2, 3, 4, 5, and 6; or a pharmaceutically acceptable salt, amide or ester thereof.

133. The compound of any of embodiments 130-132 which is a compound as defined in any of embodiments 1-129.

134. A compound selected from Chem. 30, Chem. 31, Chem. 32, Chem. 33, and Chem. 34; or a pharmaceutically acceptable salt, amide or ester thereof.

135. A compound, preferably according to embodiment 134, the name of which is selected from the names of the compounds of Examples 1a, 1b, 2a, 3a, and 6a; or a pharmaceutically acceptable salt, amide or ester thereof.

136. The compound of any of embodiments 134-135 which is a compound as defined in any of embodiments 1-129.

137. A compound selected from Chem. 21, Chem. 22, Chem. 23, Chem. 24, and Chem. 25; or a pharmaceutically acceptable salt, amide or ester thereof.

138. The compound of embodiment 137 which is a GLP-1 parent drug.

139. A compound comprising a peptide sequence selected from the following analogues of SEQ ID NO: 1: (i) 7HOHis, 18K, 22E, 25V, 26R, 31K, 34R; (ii) 7HOHis, 18K, 22E, 25V, 26R, 31K, 34R; (iii) 7HOHis, 34R, 37K; (iv) 7HOHis, 18K, 22E, 34Q; (v) 7HOHis, 8Aib, 22E, 26R, 27K, 34R; and (vi) 7HOHis, 8Aib, 23R, 34R.

140. The compound of embodiment 139 which has a peptide sequence selected from (i)-(vi).

141. The compound of any of embodiments 139-140 which is an analogue of GLP-1(8-37) SEQ ID NO: 1.

142. The compound of any of embodiments 137-141 which has GLP-1 activity, wherein GLP-1 activity is preferably defined as in any of embodiments 109-126 above.

143. The compound of any of embodiments 137-142 which is stabilised against degradation by DPP-IV.

144. The compound of any of embodiments 137-143 which has an extended half-life.

145. A compound selected from Chem. 41 (Boc-NMe-Ile-Val-OH), Chem. 42(Boc-NMe-Val-Val-OH), and Chem. 44 (Boc-NMe-Gly-Val-OH); or a salt, amide or ester thereof.

146. The compound of embodiment 145 which is an intermediate compound.

147. The compound of any of embodiments 145-146 wherein Boc-NMe-Ile-Val-OH refers to

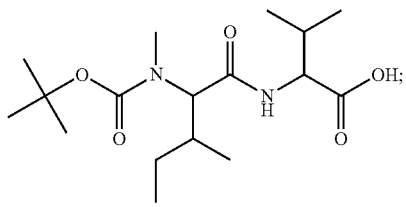

Chem. 41 or a salt, amide or ester thereof.

148. The compound of any of embodiments 145-147, wherein Boc-NMe-Val-Val-OH refers to

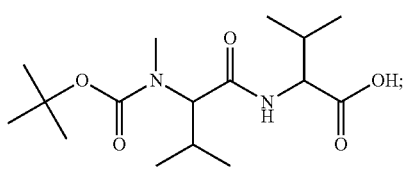

Chem. 42 or a salt, amide or ester thereof.

149. The compound of any of embodiments 145-147, wherein Boc-NMe-Ile-Val-OH refers to

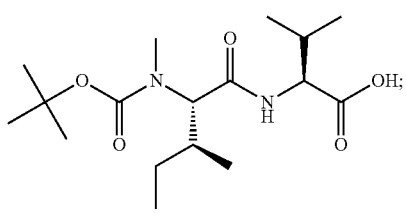

Chem. 41a or a salt, amide or ester thereof.

150. The compound of any of embodiments 145-147, wherein Boc-NMe-Val-Val-OH refers to

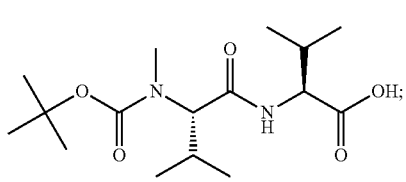

Chem. 42a or a salt, amide or ester thereof.

151. The compound of any of embodiments 145-147, wherein Boc-NMe-Gly-Val-OH refers to

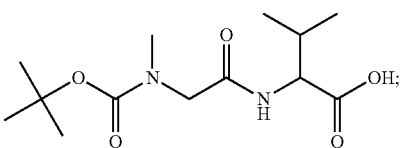

Chem. 44 or a salt, amide or ester thereof.

152. The compound of any of embodiments 145-147 wherein Boc-NMe-Gly-Val-OH refers to

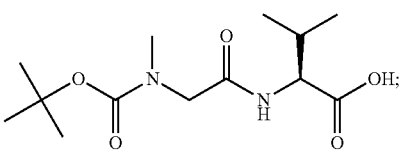

Chem. 44a or a salt, amide or ester thereof.

153. A compound selected from the following: 2-[2-[2-[[2-[2-[2-[[(4S)-5-tert-butoxy-4-[10-(4-tert-butoxycarbonyl-phenoxy)decanoylamino]-5-oxo-pentanoyl]amino]ethoxy]ethoxy]-acetyl]amino]ethoxy]ethoxy]acetic acid; and

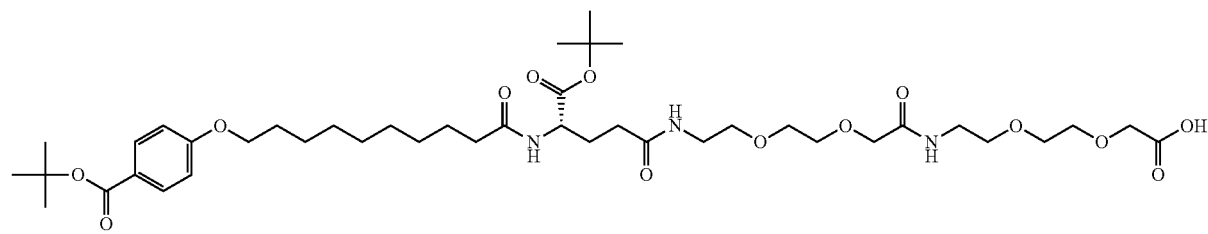

Chem. 43 or a pharmaceutically acceptable salt, amide, or ester thereof.

154. A method of achieving release in vivo of an active and stabilised parent drug GLP-1 compound of the general formula II: (HOHis)-(GLP-1 peptide), or a pharmaceutically acceptable, salt, amide, or ester thereof, by administering a prodrug thereof as defined in any of the above embodiments 1-136.

155. The method of embodiment 154, wherein the prodrug is transformed in vivo to release the active drug with a long $t\frac{1}{2}$.

156. A compound according to any of embodiments 1-144, for use as a medicament.

157. A compound according to any of embodiments 1-144, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

158. A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression—by administering a pharmaceutically active amount of a compound according to any of embodiments 1-144.

Additional Particular Embodiments

The following are particular embodiments of the invention:

1. A GLP-1 compound of the general formula I:

R1-(NHXaa1)-Xaa2-(OHis)-(GLP-1 peptide)   (Formula I)

wherein
R1 is lower alkyl;
(NHXaa1) is an amino acid;
Xaa2 is an amino acid; and
(OHis) is a radical of imidazole-lactic acid of formula Chem. 1:

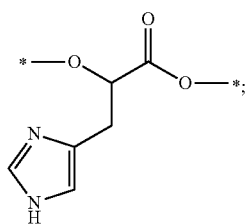

Chem. 1 or a pharmaceutically acceptable salt, amide, or ester thereof.

2. The compound of embodiment 1, which is a GLP-1 prodrug.
3. The compound of any of embodiments 1 and 2, which is a GLP-1 ester prodrug.
4. The compound of any of embodiments 1-3, which is a GLP-1 depsipeptide.
5. The compound of any of embodiments 1-4, wherein the bond between Xaa2 and (OHis) is an ester bond.
6. The compound of any of embodiments 1-5, wherein the bond between (NHXaa1) and Xaa2 is an amide bond.
7. The compound of any of embodiments 1-6, wherein the bond between (OHis) and (GLP-1 peptide) is an amide bond.
8. The compound of any of embodiments 1-7, wherein R1 is attached to the alpha-amino group of (NHXaa1).
9. The compound of any of embodiments 1-8, which is an N-terminally extended GLP-1 peptide.
10. The compound of any of embodiment 1-9, wherein R1 has from one to six carbon atoms.
11. The compound of any of embodiments 1-10, wherein R1 is straight alkyl.
12. The compound of any of embodiments 1-10, wherein R1 is branched alkyl.
13. The compound of any of embodiments 1-11, wherein R1 is methyl.
14. The compound of any of embodiments 1-13, wherein (NHXaa1) is Gly, Val, or Ile.
15. The compound of any of embodiments 1-14, wherein (NHXaa1) is Gly.
16. The compound of any of embodiments 1-14, wherein (NHXaa1) is Val.
17. The compound of any of embodiments 1-14, wherein (NHXaa1) is Ile.
18. The compound of any of embodiments 1-17, wherein Xaa2 does not comprise an N-alkylated amino acid.
19. The compound of any of embodiments 1-18, wherein Xaa2 is a proteinogenic amino acid.
20. The compound of any of embodiments 1-19, wherein Xaa2 is a beta-branched amino acid.
21. The compound of any of embodiments 1-20, wherein Xaa2 is Val.
22. The compound of any of embodiments 1-21, wherein (OHis) has the formula of Chem. 2:

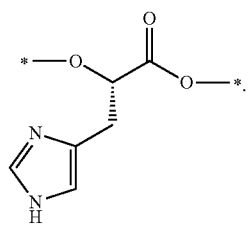

Chem. 2

23. The compound of any of embodiments 1-22, wherein (OHis) is attached to the N-terminus of the GLP-1 peptide.
24. The compound of any of embodiments 1-23 wherein GLP-1 peptide is GLP-1(8-37) (SEQ ID NO: 1) or an analogue thereof.
25. The compound of embodiment 24, wherein the analogue has a maximum of 6 amino acid changes as compared to GLP-1(8-37) (SEQ ID NO: 1).
26. The compound of embodiment 24, wherein the analogue has a maximum of 5 amino acid changes as compared to GLP-1(8-37) (SEQ ID NO: 1).
27. The compound of embodiment 24, wherein the analogue has a maximum of 4 amino acid changes as compared to GLP-1(8-37) (SEQ ID NO: 1).
28. The compound of embodiment 24, wherein the analogue has a maximum of 3 amino acid changes as compared to GLP-1(8-37) (SEQ ID NO: 1).
29. The compound of embodiment 24, wherein the analogue has a maximum of 2 amino acid changes as compared to GLP-1(8-37) (SEQ ID NO: 1).
30. The compound of embodiment 24, wherein the analogue has a maximum of 1 amino acid change as compared to GLP-1(8-37) (SEQ ID NO: 1).
31. The compound of embodiment 24, wherein the analogue has a minimum of 1 amino acid changes as compared to GLP-1(8-37) (SEQ ID NO: 1).
32. The compound of embodiment 24, wherein the analogue has a minimum of 2 amino acid changes as compared to GLP-1(8-37) (SEQ ID NO: 1).
33. The compound of embodiment 24, wherein the analogue has a minimum of 3 amino acid changes as compared to GLP-1(8-37) (SEQ ID NO: 1).
34. The compound of embodiment 24, wherein the analogue has a minimum of 4 amino acid changes as compared to GLP-1(8-37) (SEQ ID NO: 1).

35. The compound of embodiment 24, wherein the analogue has a minimum of 5 amino acid changes as compared to GLP-1(8-37) (SEQ ID NO: 1).
36. The compound of embodiment 24, wherein the analogue has a minimum of 6 amino acid change as compared to GLP-1(8-37) (SEQ ID NO: 1).
37. The compound of any of embodiments 24-36, wherein the analogue, when compared to GLP-1(8-37) (SEQ ID NO: 1), comprises at least one amino acid substitution selected from the following: 18K, 22E, 25V, 26R, 31K, 34R or 34Q, and/or 37K, wherein the position numbering refers to GLP-1(8-37).
38. The compound of any of embodiments 24-37, wherein the analogue is the variant (18K, 22E, 25V, 26R, 31K, 34R) of GLP-1(8-37) (SEQ ID NO: 1).
39. The compound of any of embodiments 24-37, wherein the analogue is the variant (34R, 37K) of GLP-1(8-37) (SEQ ID NO: 1).
40. The compound of any of embodiments 24-38, wherein the analogue is the variant (18K, 22E, 34Q) of GLP-1(8-37) (SEQ ID NO: 1).
41. The compound of any of embodiments 1-23, wherein GLP-1 peptide is a derivative of a) GLP-1(8-37) (SEQ ID NO: 1), or b) the analogue as defined in any of embodiments 24-40.
42. The compound of embodiment 41, wherein at least one substituent is covalently attached to the peptide defined in a) or b).
43. The compound of any of embodiments 41-42, wherein the substituent is a side chain.
44. The compound of embodiment 43, wherein the side chain is capable of forming non-covalent aggregates with albumin.
45. The compound of any of embodiments 43-44, wherein the side chain is an albumin binding moiety.
46. The compound of embodiment 45, wherein the albumin binding moiety comprises a protracting moiety and optionally a linker.
47. The compound of any of embodiments 45-46, wherein the albumin binding moiety, the protracting moiety, or the linker is covalently attached to a lysine residue of the peptide by acylation, preferably to the epsilon amino group thereof.
48. The compound of any of embodiments 46-47, wherein the protracting moiety is selected from a) fatty diacids, and b) fatty acids, optionally with a terminal, or distal, phenyl or phenoxy group, both optionally substituted.
49. The compound of embodiment 48, wherein a carboxy group of the fatty acid or fatty diacid is acylated, optionally via a linker, to a lysine residue of the peptide, preferably at the epsilon-amino group thereof.
50. The compound of any of embodiments 47-49, wherein the protracting moiety is Chem. 3: HOOC—$C_6H_4$—O—$(CH_2)_9$—CO—*; wherein preferably the HOOC-group is in the para position.
51. The compound of any of embodiments 46-50, wherein the albumin binding moiety, in addition to a protracting moiety, comprises a linker.
52. The compound of embodiment 51, wherein the linker is between the protracting moiety and the peptide.
53. The compound of embodiment 52, wherein the linker is covalently attached to a lysine residue of the peptide by acylation, preferably to the epsilon amino group of a lysine residue in the peptide.
54. The compound of any of embodiments 51-53, wherein the linker includes one or more linker elements.
55. The compound of embodiment 54, wherein a first linker element is a di-radical of 8-amino-3,6-dioxaoctanic acid, that may be represented by the formula Chem. 4:
Chem. 4: *—NH—$(CH_2)_2$—O—$(CH_2)_2$—O—$CH_2$—CO—*, and/or that may be designated OEG.
56. The compound of any of embodiments 54-55, wherein a second linker element is a di-radical of Glu, such as gamma-Glu, or briefly gGlu, where the gamma carboxy group of the amino acid glutamic acid is used for connection to another linker element, or to the epsilon-amino group of lysine.
57. The compound of any of embodiments 54-56, wherein the linker includes one or more first linker elements, and/or one or more second linker elements.
58. The compound of any of embodiments 51-57 wherein the linker is gGlu-2×OEG.
59. The compound of embodiment 58, wherein the alpha-amino group of gGlu forms an amide bond with the carboxy group of the protracting moiety, the gamma carboxy group of gGlu forms an amide bond with the N-terminal end of OEG, and the C-terminal end of OEG forms an amide bond with an epsilon amino group of a Lys residue in the peptide.
60. The compound of any of embodiments 42-59, wherein the at least one substituent is attached to the epsilon amino group of a Lys residue at a position corresponding to at least one, respectively, of the following positions of GLP-1(8-37) (SEQ ID NO: 1): 18, 26, 31, and/or 37.
61. The compound of embodiment 60, which has two substituents attached to position a) 18 and 31, b) 26 and 37, or c) 18 and 26, wherein the position numbering refers to GLP-1(8-37); wherein the compound preferably has one substituent attached to a) each of positions 18 and 31, b) each of positions 26 and 37, or c) each of positions 18 and 26.
62. The compound of any of embodiments 1-61, wherein GLP-1 peptide is selected from the following:

Chem. 21a:

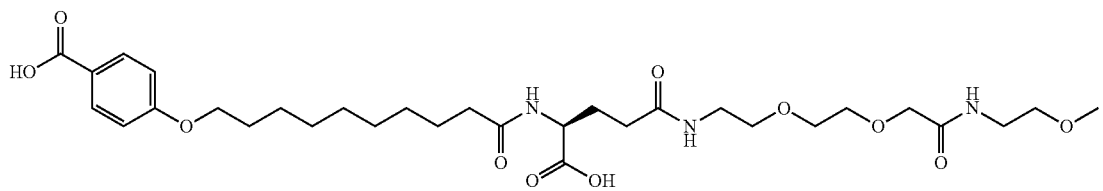

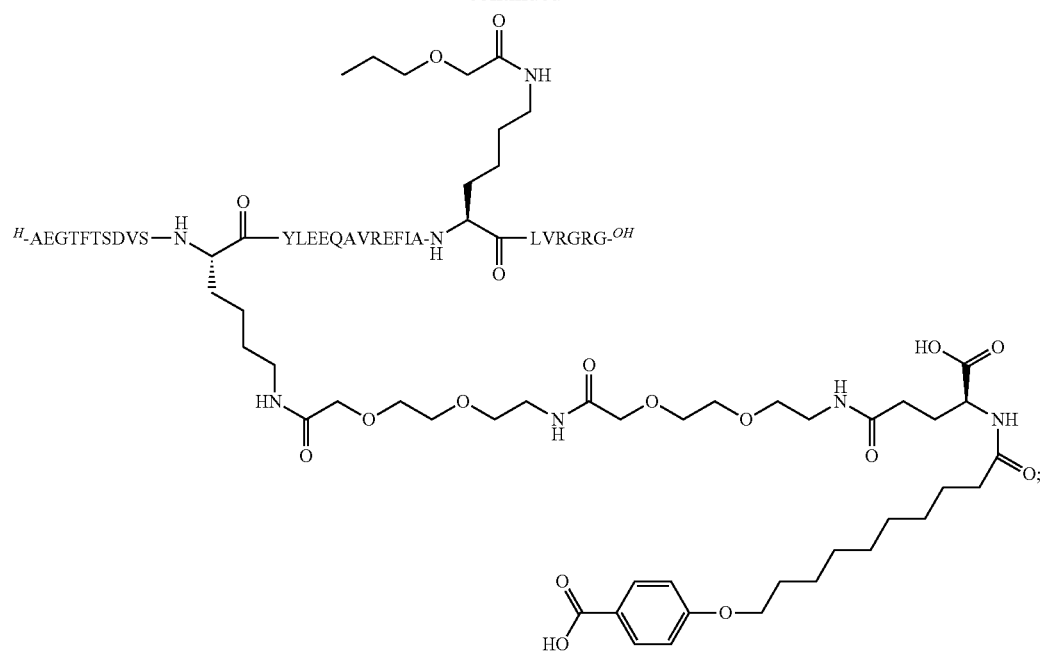
Chem. 22a:
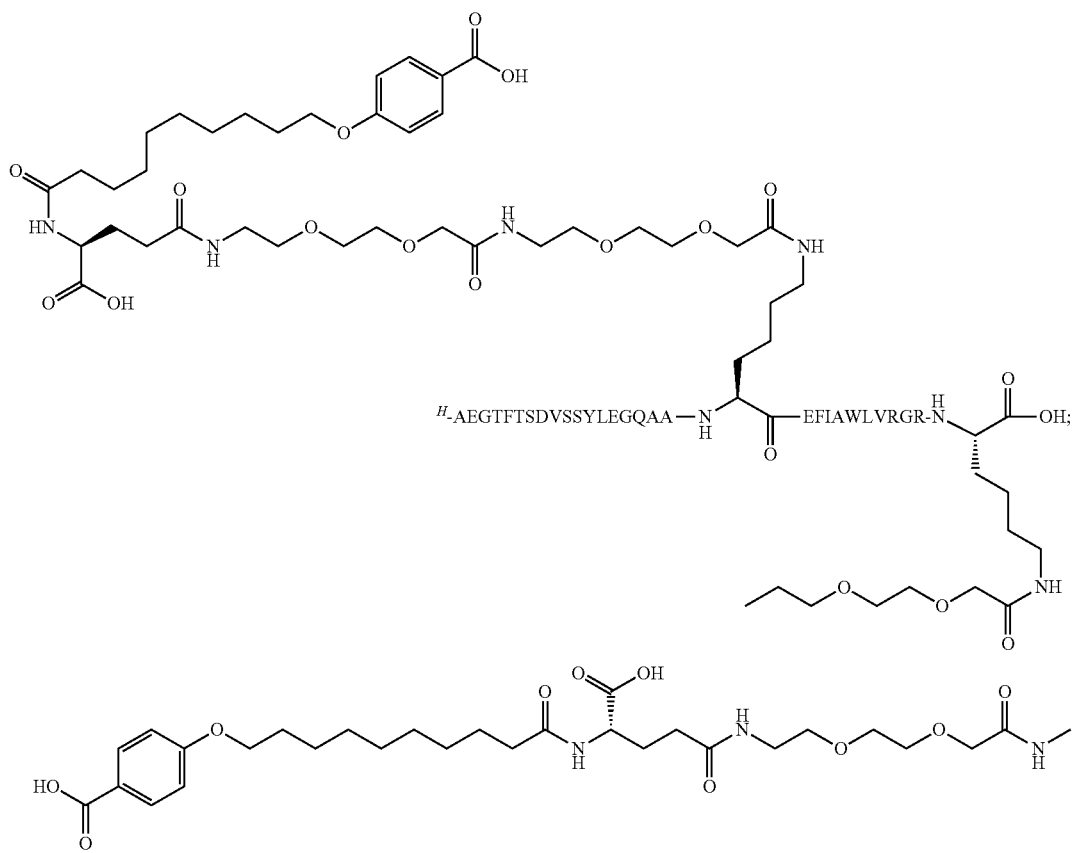

Chem. 23a:

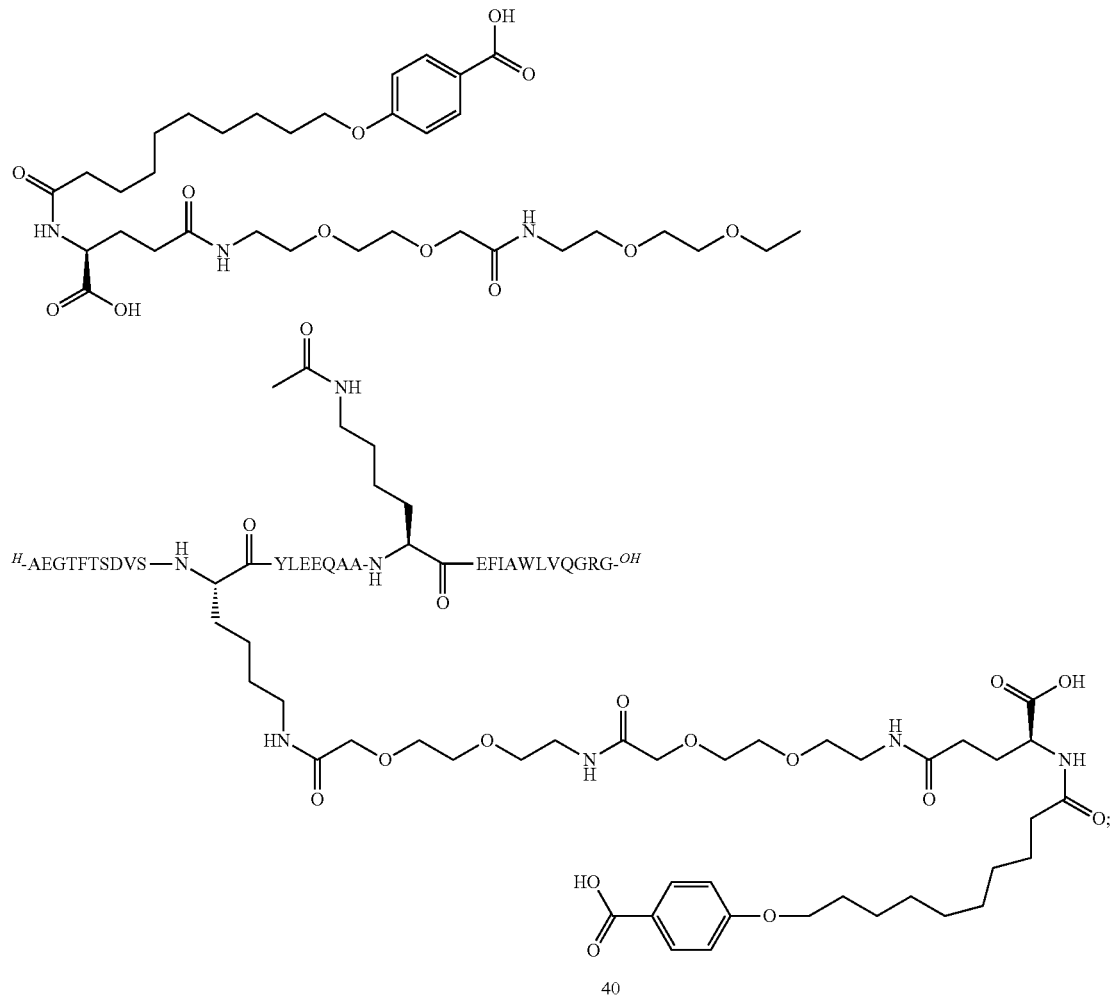

or a pharmaceutically acceptable salt, amide, or ester thereof.

63. The compound of any of embodiments 1-50 which has an extended half-life, preferably an extended half-life in vitro, or in vivo; for example as compared to the corresponding comparative compound in which R1 is H.

64. The compound of embodiment 63, wherein the in vitro prodrug half-life is measured at 37° C. in
  a) 25 mM phosphate buffer (pH 7.4); and/or
  b) a solution of 200 ul 200 mM phosphate buffer (pH 7.4) and 800 ul plasma;
and wherein the concentration of the compound may be determined using any suitable method, such as UPLC.

65. The compound of embodiment 64, wherein the prodrug half-life is determined using a) the Buffer method and/or b) the Plasma method, for example generally as described in Example 7.

66. The compound of any of embodiments 63-65 which has a prodrug half-life that is at least 2 times, preferably at least 3 times, more preferably at least 4 times, even more preferably at least 5 times, or most preferably at least 6 times that of the comparative compound.

67. The compound of any of embodiments 1-66, which includes in its structure a compound element of the formula II: (HOHis)-(GLP-1 peptide) (Formula II), wherein (HOHis) is imidazole-lactic acid corresponding to the (OHis) radical of Chem 1, and the bond, and GLP-1 peptide are as defined in any of embodiments 1-66 above, which compound element of formula II has GLP-1 activity.

68. The compound of embodiment 67, wherein (HOHis) has the formula Chem. 1a:

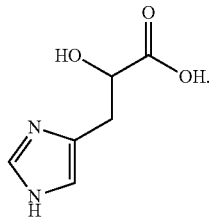 [SMILES: O=C(O)C(O)Cc1c[nH]cn1]

69. The compound of embodiment 67, wherein (HOHis) has the formula Chem. 2a:

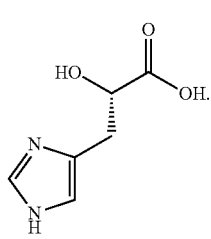 [SMILES: O=C(O)[C@@H](O)Cc1c[nH]cn1]

70. The compound of any of embodiments 67-69, wherein the compound element is a GLP-1 parent drug.
71. The compound of any of embodiments 67-70, wherein GLP-1 activity of the compound element refers to the capability of activating the human GLP-1 receptor.
72. The compound of embodiment 71, wherein activation of the human GLP-1 receptor is measured in an in vitro assay, as the potency of cAMP production.
73. The compound of any of embodiments 67-72, wherein the compound element has a potency corresponding to an $EC_{50}$
a) below 2000 pM, preferably below 1800 pM, more preferably below 1600 pM, even more preferably below 1400 pM, or most preferably below 1200 pM;
c) below 1000 pM, preferably below 800 pM, more preferably below 600 pM, even more preferably below 500 pM, or most preferably below 400 pM; or
d) below 300 pM, preferably below 250 pM, more preferably below 200 pM, even more preferably below 150 pM, or most preferably below 100 pM.
74. The compound of any of embodiments 72-73, wherein the potency is determined as $EC_{50}$ for stimulation of the formation of cAMP in a medium containing the human GLP-1 receptor, preferably using a stable transfected cell-line such as BHK467-12A (tk-ts13), and/or using for the determination of cAMP a functional receptor assay, e.g. based on competition between endogenously formed cAMP and exogenously added biotin-labelled cAMP, in which assay cAMP is more preferably captured using a specific antibody, and/or wherein an even more preferred assay is the AlphaScreen cAMP Assay, most preferably the one described in Example 8.
75. The compound of any of embodiments 72-74, wherein the reciprocal of (the $EC_{50}$ value of the compound element of formula II, divided by the $EC_{50}$ value of the corresponding comparative drug of the formula III:
(His7)-(GLP-1 peptide) (Formula III), wherein (His7) refers to L-His at position 7 of GLP-1(8-37) (SEQ ID NO: 1 extended by an N-terminal His), the bond is an amide bond, and the GLP-1 peptide is the same as in the compound),
is at least 0.1, preferably at least 0.2, more preferably at least 0.3, even more preferably at least 0.4, or most preferably at least 0.5.
76. The compound of any of embodiments 67-76, wherein GLP-1 activity of the compound element refers to the capability of binding to the human GLP-1 receptor in the presence of low albumin.
77. The compound of embodiment 76, for which the GLP-1 receptor binding affinity ($IC_{50}$) of the compound element in the presence of 0.005% HSA (low albumin) is
a) below 1000 nM, preferably below 500 nM, more preferably below 100 nM, or most preferably below 50 nM;
b) below 40 nM, preferably below 30.0 nM, still more preferably below 20.0 nM, even more preferably below 10.0 nM, or most preferably below 5.00 nM.
78. The compound of any of embodiments 76-77, wherein the binding affinity to the GLP-1 receptor is measured by way of displacement of $^{125}I$-GLP-1 from the receptor, preferably using a SPA binding assay, more preferably as described in Example 10.
79. The compound of any of embodiments 76-78, wherein the reciprocal of (the $IC_{50}$ value of the compound element of formula II divided by the $IC_{50}$ value of the corresponding comparative drug of the formula III:
(His7)-(GLP-1 peptide) (Formula III), wherein (His7) refers to L-His at position 7 of GLP-1(7-37) (SEQ ID NO: 1 extended by an N-terminal His), the bond is an amide bond, and the GLP-1 peptide is the same as in the compound),
is at least 0.1, preferably at least 0.2, more preferably at least 0.3, even more preferably at least 0.4, or most preferably at least 0.5.
80. A compound selected from Chem. 51, Chem. 52, Chem. 53, Chem. 54, and Chem. 55; or a pharmaceutically acceptable salt, amide or ester thereof.
81. A compound, preferably according to embodiment 80, the structure of which is selected from the structures shown in Examples 1, 2, 3, 4, and 5; or a pharmaceutically acceptable salt, amide or ester thereof.
82. A compound, preferably according to any of embodiments 80 and/or 81, the name of which is selected from the names of the compounds of Examples 1, 2, 3, 4, and 5; or a pharmaceutically acceptable salt, amide or ester thereof.
83. The compound of any of embodiments 80-82 which is a compound as defined in any of embodiments 1-79.
84. A compound selected from Chem. 21, Chem. 22, and Chem. 23; or a pharmaceutically acceptable salt, amide or ester thereof.
85. The compound of embodiment 84 which is a GLP-1 parent drug.
86. The compound of any of embodiments 84-85 which has GLP-1 activity, wherein GLP-1 activity is preferably defined as in any of embodiments 67-79 above.
87. The compound of any of embodiments 84-86 which is stabilised against degradation by DPP-IV.
88. The compound of any of embodiments 84-87 which has an extended half-life.
89. A compound selected from Boc-NMe-Ile-Val-OH, and Boc-NMe-Val-Val-OH; or a salt, amide or ester thereof.
90. The compound of claim 89 which is an intermediate compound.
91. The compound of any of claims 89-90 wherein Boc-NMe-Ile-Val-OH refers to

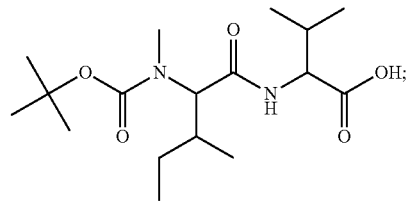

Chem. 41 or a salt, amide or ester thereof.
92. The compound of any of claims 89-91 wherein Boc-NMe-Val-Val-OH refers to

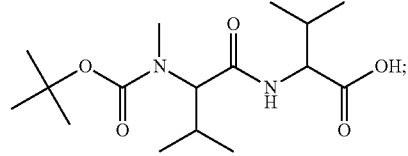

Chem. 42 or a salt, amide or ester thereof.

93. The compound of any of claims 89-91, wherein Boc-NMe-Ile-Val-OH refers to

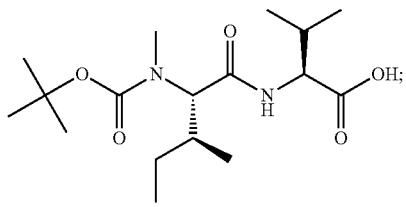
Chem. 41a or a salt, amide or ester thereof.

94. The compound of any of claims 89-91, wherein Boc-NMe-Val-Val-OH refers to

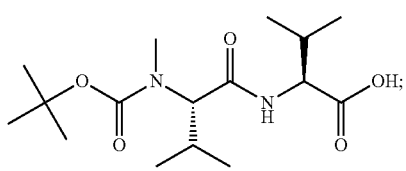
Chem. 42a or a salt, amide or ester thereof.

95. A compound according to any of embodiments 1-83, for use as a medicament.

96. A compound according to any of embodiments 1-83, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

97. A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression— by administering a pharmaceutically active amount of a compound according to any of embodiments 1-83.

98. A compound according to any of embodiments 84-88, for use as a medicament.

99. A compound according to any of embodiments 84-88, for use in the treatment and/or prevention of all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression.

100. A method for treating or preventing all forms of diabetes and related diseases, such as eating disorders, cardiovascular diseases, gastrointestinal diseases, diabetic complications, critical illness, and/or polycystic ovary syndrome; and/or for improving lipid parameters, improving β-cell function, and/or for delaying or preventing diabetic disease progression—by administering a pharmaceutically active amount of a compound according to any of embodiments 84-88.

EXAMPLES

This experimental part starts with a list of abbreviations, and is followed by a section including general methods for synthesising and characterising prodrugs and drugs of the invention. Then follows a number of examples which relate to the preparation of specific prodrugs, and at the end a number of examples have been included relating to the activity and properties of these prodrugs and drugs (section headed pharmacological methods).

The examples serve to illustrate the invention.

LIST OF ABBREVIATIONS

Aib: α-Aminoisobutyric acid
API: Active Pharmaceutical Ingredient
AUC: Area Under the Curve
BG: Blood Glucose
BHK Baby Hamster Kidney
BSA: Bovine Serum Albumin
BW: Body Weight
Boc: t-Butyloxycarbonyl
BSA: Bovine serum albumin
CAS: Chemical Abstracts Service
$CDCl_3$: Deuterated chloroform
Collidine: 2,4,6-Trimethylpyridine
DCM: Dichloromethane
Dde: 1-(4,4-Dimethyl-2,6-dioxocyclohexylidene)ethyl
DesH: Des-amino histidine (may also be referred to as imidazopropionic acid, Imp)
DIC: Diisopropylcarbodiimide
DIPEA: Diisopropylethylamine
DMEM: Dulbecco's Modified Eagle's Medium (DMEM)
DMSO: Dimethylsulfoxide
DPP-IV: Dipeptidyl peptidase-4
EDAC    1-Ethyl-3-[3-dimethylaminopropyl]carbodiimide hydrochloride
EDTA: Ethylenediaminetetraacetic acid
EGTA: Ethylene glycol tetraacetic acid
EtOAc Ethylacetate
EtOH: Ethanol
FCS: Fetal Calf Serum
Fmoc: 9-Flu orenylmethyloxycarbonyl
HEPES:    4-(2-Hydroxyethyl)-1-piperazineethanesulfonic acid
HOAt: 1-Hydroxy-7-azabenzotriazole
HOBt: 1-Hydroxybenzotriazole
HPLC: High Performance Liquid Chromatography
HSA: Human Serum Albumin
IBMX: 3-Isobutyl-1-methylxanthine
Imp: Imidazopropionic acid (also referred to as des-amino histidine, DesH)
i.v. Intravenously
ivDde:    1-(4,4-Dimethyl-2,6-dioxocyclohexylidene)-3-methylbutyl
IVGTT: Intravenous Glucose Tolerance Test
LCMS: Liquid Chromatography Mass Spectroscopy
LYD: Landrace Yorkshire Duroc
MALDI-MS: See MALDI-TOF MS
MALDI-TOF MS: Matrix-Assisted Laser Desorption/Ionisation Time of Flight Mass Spectroscopy
MeOH: Methanol
MES: 2-(N-morpholino)ethanesulfonic acid
Mmt: 4-Methoxytrityl
MSNT: 1-(Mesitylene-2-sulfonyl)-3-nitro-1,2,4-triazole
Mtt: 4-Methyltrityl
NaOEt: Sodium ethanolat NMP: N-Methyl pyrrolidone
OEG: 8-Amino-3,6-dioxaoctanic acid
OtBu: Tert-butyl ester
Pbf: 2,2,4,6,7-Pentamethyldihydrobenzofuran-5-sulfonyl
PBS: Phosphate Buffered Saline
PD: Pharmacodynamic
Pen/Strep: Pencillin/Streptomycin
PK: Pharmacokinetic
PyBob Benzotriazol-1-yl-oxytripyrrolidinophosphonium hexafluorophosphate
RP: Reverse Phase
RP-HPLC: Reverse Phase High Performance Liquid Chromatography
RT: Room Temperature
Rt: Retention time
s.c.: Subcutaneously
SD: Standard Deviation
SEC-HPLC: Size Exclusion High Performance Liquid Chromatography
SEM: Standard Error of Mean
SPA: Scintillation Proximity Assay
SPPS: Solid Phase Peptide Synthesis
TBDMS: Tert-butyldimethylsilyl or tert-butyldimethylsilane
TBTU: (2-(1H-Benzotriazol-1-yl-)-1,1,3,3 tetramethyluronium tetrafluoroborate)
tBu: Tert-butyl
TEA: Triethylamine
TFA: Trifluoroacetic acid
TFE: Trifluoroethanol
THF: Tetrahydrofuran
TIS: Triisopropylsilane
TLC: Thin Layer Chromatography
TNBS: Trinitrobenzene sulfonate
Tol Toluene
Tris: Tris(hydroxymethyl)aminomethane or 2-amino-2-hydroxymethyl-propane-1,3-diol
Trt: Triphenylmethyl (trityl)
Tween20: Polyoxyethylene (20) sorbitan monolaurate
UPLC: Ultra Performance Liquid Chromatography
Materials and Methods
Unless otherwise stated all reagents were reagent-grade.
Materials
L-beta-Imidazolelactic acid, (2S)-2-hydroxy-3-(1H-imidazol-4-yl)propanoic acid (CAS 14403-45-3)
H-Val-OMe.HCl, L-Valine methyl ester hydrochloride (CAS 6306-52-1)
Fmoc-8-amino-3,6-dioxaoctanoic acid (CAS 166108-71-0)
Fmoc-L-Glutamic acid 1-tert-butyl ester (CAS 84793-07-7)
10-(4-tert-butoxycarbonylphenoxy)decanoic acid (prepared as described in Example 25, step 2 of WO 2006/082204)
Chemical Methods This section is divided in two: Section A relating to general methods (of preparation (A1); and of detection and characterisation (A2)), and section B, in which the preparation and characterisation of a number of specific intermediate compounds (B1), parent drugs (B2), and prodrugs (B3) is described.

A. General Methods

A1. Methods of Preparation

This section relates to methods for solid phase peptide synthesis (SPPS methods, including methods for de-protection of amino acids, methods for cleaving the peptide from the resin, and for its purification), as well as methods for detecting and characterising the resulting peptide (LCMS, MALDI, and UPLC methods). The solid phase synthesis of peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used (available from, e.g., Novabiochem, see also W. R. Sampson (1999), J. Pep. Sci. 5, 403). The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, or, Fmoc-Val-OH etc. supplied from e.g. Anaspec, Bachem, Iris Biotech, or Novabiochem. Where nothing else is specified the natural L-form of the amino acids are used. The N-terminal amino acid was Boc protected at the alpha amino group (e.g. Boc-His(Boc)-OH, or Boc-His(Trt)-OH for peptides with His at the N-terminus). In case of modular albumin binding moiety attachment using SPPS the following suitably protected building blocks such as but not limited to Fmoc-8-amino-3,6-dioxaoctanoic acid, Fmoc-tranexamic acid, Fmoc-Glu-OtBu, octadecanedioic acid mono-tert-butyl ester, nonadecanedioic acid mono-tert-butyl ester, tetradecanedioic acid mono-tert-butyl ester, or 4-(9-carboxynonyloxy) benzoic acid tert-butyl ester were used. All operations stated below were performed at 250-μmol synthesis scale.

1. Synthesis of Resin Bound Protected Peptide Backbone Method: SPPS_A

The protected peptidyl resin was synthesised according to the Fmoc strategy on an Applied Biosystems 433 peptide synthesiser in a 250-μmol scale with four fold excess of Fmoc-amino acids, using a modified version of the manufacturer supplied FastMoc UV protocol in which for every coupling 4 eq DIC (1 M in NMP) and 4 eq HOBt (1 M in NMP) was added first to the amino acid vial to pre-activate the amino acid for 10 minutes before adding to the resin. After addition of the activated amino acid the resin was shaken for 30 minutes after which 4 eq DIPEA (2 M in NMP) was added and reaction continued for another 30 minutes. Deprotection of Fmoc groups were according to manufacturer method with 20% Piperidine in NMP and UV monitoring and 2-5 feedback loops of the deprotection of the Fmoc protection group, in some cases double couplings were used, meaning that after the first coupling, the resin is drained and another vial of Fmoc-amino acid was activated and added to the resin. Coupling time was ~20 minutes without addition of base. The resin used for the synthesis of the peptide C-terminal amides was Rink-Amide resin and either preloaded Wang (e.g. low load Fmoc-Gly-Wang or Fmoc-Lys(Mtt)-wang) or chlorotrityl resin for peptides with a carboxy C-terminal. The protected amino acid derivatives used were standard Fmoc-amino acids (supplied from e.g. Anaspec, or Novabiochem) supplied in pre-weighed cartridges suitable for the ABI433A synthesiser with the exception of unnatural amino acids such as Fmoc-Aib-OH (Fmoc-aminoisobutyric acid). The N terminal amino acid was either Fmoc or Boc protected at the alpha amino group. The epsilon amino group of lysines in the sequence were either protected with Mtt, Mmt, Dde, ivDde, or Boc, depending on the route for attachment of the albumin binding moiety and spacer. The synthesis of the peptides may in some cases be improved by the use of dipeptides protected on the dipeptide amide bond with a group that can be cleaved under acidic conditions such but not limited to 2-Fmoc-oxy-4-methoxybenzyl or 2,4,6-trimethoxybenzyl. In cases where a serine or a threonine is present in the peptide, the use of pseudoproline dipeptides may be used (see e.g. catalogue from Novobiochem 2009/2010 or newer version, or W. R. Sampson (1999), J. Pep. Sci. 5, 403).

Method: SPPS_B

SPPS method B refers to the synthesis of a protected peptidyl resin using Fmoc chemistry on a microwave-based Liberty peptide synthesiser (CEM Corp., North Carolina). A suitable resin is a pre-loaded, low-load Wang resin available from Novabiochem (e.g. low load Fmoc-Lys(Mtt)-Wang resin, 0.35 mmol/g). Fmoc-deprotection was with 5% piperidine in NMP at up to 70 or 75° C. The coupling chemistry was DIC/HOAt in NMP. Amino acid/HOAt solutions (0.3 M in NMP at a molar excess of 3-10 fold) were added to the resin followed by the same molar equivalent of DIC (0.75M in NMP). For example, the following amounts of 0.3M amino acid/HOAt solution were used per coupling for the following scale reactions: Scale/ml, 0.10 mmol/2.5 ml, 0.25 mmol/5 ml, 1 mmol/15 ml. Coupling times and temperatures were generally 5 minutes at up to 70 or 75° C. Longer coupling times were used for larger scale reactions, for example 10 min. Histidine amino acids were double coupled at 50° C., or quadruple coupled if the previous amino acid was sterically hindered (e.g. Aib). Arginine amino acids were coupled at RT for 25 min then heated to 70 or 75° C. for 5 min. Some amino acids such as but not limited to Aib, were "double coupled", meaning that after the first coupling (e.g. 5 min at 75° C.), the resin is drained and more reagents are added (amino acid, HOAt and DIC), and the mixture in heated again (e.g. 5 min at 75° C.). When a chemical modification of a lysine sidechain was desired, the lysine was incorporated as Lys(Mtt). The Mtt group was removed by washing the resin with DCM and suspending the resin in neat (undiluted) hexafluoroisopropanol for 20 minutes followed by washing with DCM and NMP. The chemical modification of the lysine was performed either by manual synthesis or by one or more automated steps on the Liberty peptide synthesiser as described above, using suitably protected building blocks (see General methods), optionally including a manual coupling.

Method: SPPS_P

SPPS_P was performed on a Prelude Solid Phase Peptide Synthesiser from Protein Technologies (Tucson, Ariz. 85714 U.S.A.) at 250-µmol scale using six fold excess of Fmoc-amino acids (300 mM in NMP with 300 mM HOAt) relative to resin loading, e.g. low load Fmoc-Gly-Wang (0.35 mmol/g). Fmoc-deprotection was performed using 20% piperidine in NMP. Coupling was performed using 3:3:3:4 amino acid/HOAt/DIC/collidine in NMP. NMP and DCM top washes (7 ml, 0.5 min, 2×2 each) were performed between deprotection and coupling steps. Coupling times were generally 60 minutes. Some amino acids including, but not limited to Fmoc-Arg(Pbf)-OH, Fmoc-Aib-OH or Boc-His (Trt)-OH were "double coupled", meaning that after the first coupling (e.g. 60 min), the resin is drained and more reagents are added (amino acid, HOAt, DIC, and collidine), and the mixture allowed to react again (e.g. 60 min).

Method: SC_M2

The N-ε-lysine Mtt protection group was removed with 1× treatment with 0.5% TFA in DCM followed by 3× treatment with neat (undiluted) hexafluoroisopropanol or hexafluoroisopropanol/DCM (75:25) at room temperature for 15 min followed by washing 5 times with DCM, followed by 5 times with NMP. The protracting moiety (4 molar equivalents compared to resin) was dissolved in NMP. The activating reagent such as TBTU (3.88 molar equivalents relative to resin) and DIC (4 molar equivalents relative to resin) was added and the solution was stirred for 15 min. The solution was added to the resin and DIPEA (4 molar equivalents relative to resin) was added. The resin was shaken 2 to 24 hours at room temperature. The resin was washed twice with NMP, twice with NMP/DCM (1:1) and twice with DCM.

2. Cleavage of Resin Bound Peptide with or without Attached Side Chains and Purification Method: CP_M1

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% acetic acid) and purified by standard RP-HPLC on a C18, 5 µM column, using acetonitrile/water/TFA. The fractions were analysed by a combination of UPLC, and LC-MS methods, and the appropriate fractions were pooled and lyophilised.

Method: CP_M2

This method contains the following steps 1-5:

Step 1. Fmoc Removal:

The Fmoc protecting group on the terminal Glu was removed by treatment with 20% piperidine in NMP for 2 min+18 min followed by 6 times wash with NMP.

Step 2. Coupling of Fmoc-Ala-OH:

Fmoc-Ala-OH (4 molar equivalents compared to resin) was activated with TBTU (3.8 eq), HOBt (4 eq), and DIPEA (4 eq) for 10 minutes, then added to the resin and coupled for 2 h or until negative TNBS test (W. S. Hancock, J. E. Battersby, Analytical Biochemistry 1976, 71(1), 260-264). The resin was washed 6 times with NMP and 10 times with DCM.

Step 3. ε-Lys Mtt Deprotection:

The two ε-Lys Mtt protecting groups were removed by treatment with 0.5% TFA in DCM for 5 min followed by 3 times 15 min with neet hexafluoroisopropanol. The resin was washed with 6 times with DCM and 6 times with NMP. TNBS test was positive.

Step 4. Sidechain Coupling:

Bis-t-Butyl protected side chain (2-[2-[2-[[2-[2-[2-[[(4S)-5-tert-butoxy-4-[10-(4-tert-butoxycarbonylphenoxy)decanoylamino]-5-oxo-pentanoyl]amino]ethoxy]ethoxy] acetyl]amino]ethoxy]ethoxy]acetic acid) (4 molar equivalents compared to resin) was dissolved in NMP and pre-activated with TBTU (3.8 eq), HOBt (4 eq), and DIPEA (4 eq) for 15 min., then added to the resin and reacted for 2.5 hours or until TNBS test showed clear beads. The N-terminal Fmoc on Ala8 was removed as above.

Step 5. L-β-Imidazolelactic Acid Coupling:

L-beta-Imidazolelactic acid (4 molar equivalents compared to resin) was dissolved in NMP and activated with PyBOB (3.8 eq), HOBt (4 eq), and TEA (4 eq) for 10 minutes before added to the resin and coupling for 1.5 h.

A2. General Methods for Detection and Characterisation

1. LC-MS Methods

Method: LCMS_4

LCMS_4 was performed on a setup consisting of Waters Acquity UPLC system and LCT Premier XE mass spectrometer from Micromass. Eluents: A: 0.1% Formic acid in water B: 0.1% Formic acid in acetonitrile The analysis was performed at RT by injecting an appropriate volume of the sample (preferably 2-10 µl) onto the column which was eluted with a gradient of A and B. The UPLC conditions, detector settings and mass spectrometer settings were: Column: Waters Acquity UPLC BEH, C-18, 1.7 µm, 2.1 mm×50 mm. Gradient: Linear 5%-95% acetonitrile during 4.0 min (alternatively 8.0 min) at 0.4 mL/min. Detection: 214 nm (analogue output from TUV (Tunable UV detector)) MS ionisation mode: API-ES Scan: 100-2000 amu (alternatively 500-2000 amu), step 0.1 amu.

2. UPLC Methods
Method: B2_1
The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 40% A, 60% B over 16 minutes at a flow-rate of 0.40 ml/min.

Method: B4_1
The RP-analysis was performed using a Waters UPLC system fitted with a dual band detector. UV detections at 214 nm and 254 nm were collected using an ACQUITY UPLC BEH130, C18, 130 Å, 1.7 µm, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 95% A, 5% B over 16 minutes at a flow-rate of 0.40 mL/min.

Method: B29_1
The RP-analysis was performed using a Waters UPLC system fitted with a dual band detector. UV detections at 215 nm and 254 nm were collected using a kinetex 1.7u C18, 100A 2.1×150 mm column, 60° C. The UPLC system was connected to two eluent reservoirs containing: A: 90% water and 10% $CH_3CN$ with 0.045M $(NH_4)_2HPO_4$, pH 3.6, B: 20% 2-propanol, 20% water and 60% $CH_3CN$. The following step gradient was used: 35% B and 65% A over 2 minutes, then 35% B, 65% A to 65% B, 35% A over 15 minutes, then 65% B, 35% A to 80% B, 20% A over 3 minutes at a flow-rate of 0.5 ml/min.

Method: UPLC_A
The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 63% A, 37% B to 53% A, 47% B over 16 minutes at a flow-rate of 0.40 ml/min and autosampler temperature at 37° C.

Method: UPLC_B
The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 65% A, 35% B to 50% A, 50% B over 16 minutes at a flow-rate of 0.40 ml/min and autosampler temperature at 37° C.

NMR Method:
Proton NMR spectra were recorded using a Brucker Avance DPX 400 (400 MHz) with tetramethylsilane as an internal standard. Chemical shifts (δ) are given in ppm and splitting patterns are designated as follows: s, singlet; d, doublet; dd, double doublet; dt, double triplet t, triplet, tt, triplet of triplets; q, quartet; quint, quintet; sext, sextet; m, multiplet, and br=broad.

B. Specific Examples

B1. Intermediate Compounds

B1.1

S)-2-(2-Hydroxy-acetylamino)-3-methyl-butyric acid (N-hydroxyacetyl-S-valine

L-Valine (5.86 g; 0.05 mmol) was suspended in abs. EtOH (150 mL). A solution of freshly prepared NaOEt in EtOH (0.5 M, 100 mL, 1 eq) was added dropwise over 1 h at RT whereby Valine dissolved as its Na salt. The solution was stirred for another 0.5 h and filtered from little unreacted Valine. The solution was evaporated to yield the sodium salt of Valine as a white powder. The solid was transferred to a 100 mL round bottom flask and benzylglycolate (25 g, 0.15 mol, 3 eq) was added and the mixture was stirred at 85° C. overnight (15 h). The content of the flask had solidified as yellowish solid. Ether (100 mL) was added and the solid was thoroughly triturated to a fine powder. Filtered and washed 4× with ether and the white solid was dried shortly in vacuo). Yield 10.1 g (approximately 100%).

The white solid was transferred to a beaker and dissolved in 50 mL water leaving an unclear light yellowish solution. The aqueous phase was extracted 2× with ether to remove potential residual benzylglycolate by which the aqueous phase turned clear and light yellow. The aqueous phase was treated with excess (approximately 20 g, 4.7 meq/g dry resin), approximately 2 eq compared to L-Valine used) pre-washed Amberlyst 15 (H+ form) ion exchange resin (Fluka cat. no. 06423) and the resin was filtered off and washed 3× with little water.

The aqueous phase was evaporated at 45° C. in vacuo to a yellow brownish oil, which was then flushed with toluene to remove residual water. The oil was crystallised by dissolving an aliquot in EtOAc and adding toluene while triturating. The resulting white crystals were added to the oil which fast crystallised to yield 7.89 g (91%) containing some toluene.

The solid was dissolved in boiling EtOAc (25 mL) and filtered on paper to remove some dark insoluble impurities. To the re-heated filtrate was added hot toluene (10-15 mL) and colourless crystals formed upon cooling. The sample was left at 5° C. overnight, filtered and washed with EtOAc/ Tol, ether and heptane. The resulting crystals were somewhat "soft" and greasy (5.7 g, 65%), probably due to co-precipitation of some light brownish oil, so everything was recrystallised from EtOAc (25 mL). This gave a light yellow solution from which colourless crystals formed upon cooling. The compound was isolated on glass filter (G3) and washed with cold EtOAc, EtOAc/Heptane (1:1), and heptane and dried in vacuo. Yield: 5.26 g (60%)

NMR method: $^1$H NMR (DMSO-$d_6$): δ711H) 7.47 (d, 1H), 5-6 (br, 1H); 4.22 (d, 1H), 3.87 (d, 2H), 3.35 (br, 1H), 2.11 (m, 1H), 0.86 (d, 3H), 0.82 (d, 3H).

B1.2

(S)-2-[2-(tert-Butyl-dimethyl-silanyloxy)-acetylamino]-3-methyl-butyric acid

N-Hydroxyacetyl-S-valine (1.00 g, 5.74 mmol) from example B1.1 was dissolved in NMP (15 mL). TBDMS (2.40 g, 15.96 mmol, 2.8 eq) was added. Imidazole (2.58 g, 37.9 mmol, 6.6 eq) was added in portions controlling that the temperature of the solution did not raise above 30° C. by cooling in water). The clear colourless solution was stirred overnight at RT under nitrogen.

The solution was then cooled to approximately 0° C. and iced water (50 mL) was added and the unclear solution extracted twice with ether (2×50 mL). The ether was cooled to −10° C. and washed fast with cooled (below 0° C.) 1 N HCl, iced water (2×) and brine. Ether was dried over $Na_2SO_4$ and evaporated to a colourless oil (approximately 2.85 g). The oil was dissolved in MeOH (40 mL)+THF (13 mL) and a solution of $K_2CO_3$ (2.15 g, 15.6 mmol) in water (22 mL) was added. The suspension was stirred vigorously for 1 h after which it was concentrated to approximately half volume on rotary evaporator giving a clear colourless solution. This solution was extracted with hexane (3×50 mL) to remove any excess silyl reagent. Brine (45 mL) was added to the aqueous phase to give a cloudy mixture which was cooled to −10° C. and carefully acidified with cold 1 M $NaHSO_4$ (aq) to pH approximately 4-5. Upon acidification, white precipitate and $CO_2$ foaming occurred. The suspension was extracted in the cold with ether (3×50 mL) and the combined ether phases were washed with brine (2×) and dried over $Na_2SO_4$. Evaporation yielded the product as a white solid 1.17 g (70%).

NMR method: $^1$H NMR (400 MHz, $CDCl_3$): δ 6.00 (br, 2H); 4.91 (dd, 1H); 4.05 (s, 2H); 2.33 (m, 1H); 0.87 (d, 3H); 0.84 (d, 3H); 0.82 (s, 9H); 0.02 (s, 6H).

B1.3

$H_2$N-Val-O-chlorotrityl Resin 16 g 2-chlorotrityl-resin (1.5 mmol/g; 24 mmol) was swelled in DCM (150 mL) for 45 min, and DCM was drained off. A mixture of Fmoc-Val-OH (16.29 g; 48.0 mmol) and DIPEA (20.54 mL) in DCM (150 mL) was added to the resin and the mixture was shaken for 50 min. before addition of 30 mL MeOH to quench un-reacted resin. The mixture was stirred for another 10 min, before the resin was drained and washed once with DCM (150 mL). A mixture of DCM, MeOH, and DIPEA (80:15:5) was added to the resin and reacted for 10 min. before the resin was washed with DCM (3×) followed by NMP (3×).

The Fmoc group was removed by standard conditions 20% Piperidine in NMP: 2 min+18 min. The resin was then washed with NMP (6×). A standard TNBS-test was positive. The resin was washed with DCM (6×) and Ether (2×) and dried.

B1.4

2S)-2-[[(2S)-2-(tert-butoxycarbonylamino)-3-methyl-butanoyl]amino]-3-methyl-butanoic acid (Boc-Val-Val-OH ⅓ of the $H_2$N-Val-O-chlorotrityl resin (approximately 8 mmol) from example B1.3 was swelled in DCM and drained. Boc-Val-OH (5.52 g, 24 mmol) was dissolved in NMP (50 mL) and HOAt (3.26 g, 24 mmol) was added followed by DIC (3.66 mL, 24 mmol). The mixture was stirred for 10 min, before addition to the resin, and another 30 mL NMP was added. The reaction was stirred for 2½ hour until a TNBS test was negative. The resin was drained and washed with NMP (4×70 mL) and DCM (10×70 mL) followed by ether (1×100 mL).

The dipeptide was cleaved from the resin by treating the resin with HOAc:TFE:DCM (1:2:7) (100 mL) for 30 min. The solvent was drained and collected and the resin was washed with DCM (50 mL). The combined filtrate was added water (150 mL), the layers were separated and the organic phase was dried with $Na_2SO_4$ and after filtration the solvents removed by evaporation to give a white sticky foam. The product was crystallised by dissolving in hot EtOAc (5 mL) and hot heptane (20 mL) was added and the solution left to cool for crystallization at 5° C. for 2 hours. The white crystals were isolated by filtration, and washed EtOAc/heptane (1:6) and with petrol ether (40-60). After drying in vacuo the yield was 1.79 g (70%).

LCMS method: LCMS_4: Rt: 2.23 min, Exact mass: 316.200 Da, M/1: 317.03

NMR method: $^1$H NMR (400 MHz, $CDCl_3$): δ 6.76 (d, 1H); 5.27 (br. d, 1H); 4.58 (dd, 1H); 3.96 (dd, 1H); 2.25 (m, 1H); 2.07 (m, 1H); 1.44 (s, 9H); 0.92-0.99 (4× d, 12H)

B1.5

2S)-2-[[(2S)-2-[tert-butoxycarbonyl(methyl)amino]-3-methyl-pentanoyl]amino]-3-methyl-butanoic acid (Boc-N-Me-Ile-Val-OH ⅓ of the $H_2$N-Val-O-chlorotrityl resin (approximately 8 mmol) from example B1.3 was swelled in DCM and drained. Boc-N(Me)Ile-OH (5.88 g, 24 mmol) was dissolved in NMP (50 mL) and HOAt (3.26 g, 24 mmol) was added followed by DIC (3.66 mL, 24 mmol). The mixture was stirred for 10 min, before addition to the resin, and another 30 mL NMP was added. The reaction was stirred for 2½ hour until a TNBS test was negative. The resin was drained and washed with NMP (4×70 mL) and DCM (10×70 mL) followed by ether (1×100 mL).

The dipeptide was cleaved from the resin by treating the resin with HOAc:TFE:DCM (1:2:7) (100 mL) for 30 min. The solvent was drained and collected and the resin was washed with DCM (50 mL). The combined filtrate was added water (150 mL), the layers were separated and the organic phase was dried with $Na_2SO_4$ and the solvents removed by evaporation to give a white sticky foam. The product was recrystallised from EtOAc and heptane to yield white crystals. Yield 1.72 g (63%).

LCMS method: LCMS_4: Rt: 2.85 min, Exact mass: 344.231 Da; M/1: 345.04

NMR method: $^1$H NMR (400 MHz, $CDCl_3$): δ 6.86 (d, 1H); 4.53 (br, 1H); 4.19 (d, 1H); 2.80 (s, 3H); 2.24 (m, 1H); 2.10 (m, 1H); 1.47 (s, 9H); 1.05 (m, 1H); 0.84-0.97 (4×d, 12H)

B1.6

2S)-2-[[2-[tert-butoxycarbonyl(methyl)amino]acetyl]amino]-3-methyl-butanoic acid (Boc-N-Me-Gly-Val-OH ⅓ of the $H_2$N-Val-O-chlorotrityl (approximately 8 mmol) resin from Example B1.3 was swelled in DCM and drained. Boc-N(Me)Gly-OH (4.54 g, 24 mmol) was dissolved in NMP (50 mL) and HOAt (3.26 g, 24 mmol) was added followed by DIC (3.66 mL, 24 mmol). The mixture was stirred for 10 min, before addition to the resin, and another 30 mL NMP was added. The reaction was stirred for 2½ hour until a TNBS test was negative. The resin was drained and washed with NMP (4×70 mL) and DCM (10×70 mL) followed by ether (1×100 mL).

The dipeptide was cleaved from the resin by treating the resin with HOAc:TFE:DCM (1:2:7) (100 mL) for 30 min. The solvent was drained and collected and the resin was washed with DCM (50 mL). The combined filtrate was added water (150 mL), the layers were separated and the organic phase was dried with $Na_2SO_4$ and the solvents removed by evaporation to give a colorless oil. Yield 2.35 g (approximately 100%).

LCMS method: LCMS_4: Rt: 1.93 min, Exact mass 288.169 Da; M/1: 289.03

NMR method: $^1$H NMR (400 MHz, CDCl$_3$): δ 6.91 (br. d, 1H); 4.7-4.5 (br, 1H); 4.11 (d, 1H); 3.80 (d, 1H); 2.96 (s, 3H); 2.23 (m, 1H); 1.46 (s, 9H); 0.97 (d, 3H); 0.93 (d, 3H)

B1.7

2S)-2-[[2-(tert-butoxycarbonylamino)acetyl]amino]-3-methyl-butanoic acid (Boc-Gly-Val-OH Boc-Gly-OH (5.80 g, 33.11 mmol), EDAC (6.98 g, 36.4 mmol, 1.1 eq) and H-Val-OMe.HCl (4.78 g, 36.4 mmol, 1.1 eq) was dissolved in THF (50 mL) and DCM was added until a clear solution was obtained. After 20 minutes of stirring DIPEA (4.89 mL, 28.5 mmol, 2.5 eq) was added and the mixture was stirred at room temperature overnight. The solvents were evaporated and the residue dissolved in EtOAc (100 mL). The organic phase was washed with aqueous KHSO$_4$ (100 mL, 1 M) and the aqueous phase back extracted with EtOAc (100 mL). The combined organic phases were washed with 10% NaHCO$_3$ (aq) (1×100 mL) and brine (1×100 mL) and dried over MgSO$_4$. The solvents were removed on a rotary evaporator leaving Boc-Gly-Val-OMe as a light yellow oil. Yield: 8.0 g (84%).

The oil was dissolved in THF (150 mL) and LiOH (100 mL, 1 M) was added. The reaction was stirred at room temperature for 3 hours after which TLC showed full conversion of starting material. The THF was removed in vacuo, and the remaining aqueous layer was acidified by addition of 1 M KHSO4 to pH 2-3. The product was extracted twice with EtOAc (100 mL) and the combined EtOAc extracts were washed with brine (×2), dried with MgSO$_4$, filtered, and the solvents evaporated to give Boc-Gly-Val-OH as a clear oil which after standing overnight turned into a white solid (6.78 g, 89%).

NMR method: $^1$H NMR (400 MHz, CDCl$_3$): δ 9.15-9.35 (br., 1H); 7.09 (br d, 1H); 5.64 (br s, 1H); 4.59 (br d, 1H); 3.95 (br d, 1H); 3.84 (br. d, 1H); 2.25 (m, 1H); 1.45 (s, 9H); 0.97 (d, 3H); 0.93 (d, 3H)

B1.7a

2S)-2-[[(2S)-2-[tert-butoxycarbonyl(methyl)amino]-3-methyl-butanoyl]amino]-3-methyl-butanoic acid (Boc-N-Me-Val-Val-OH)

H$_2$N-Val-O-chlorotrityl resin (~5.4 mmol) made as in Example B1.3 was swelled in DCM and drained. Boc-N(Me)Val-OH (5.55 g, 24 mmol) was dissolved in NMP (50 mL) and HOAt (3.26 g, 24 mmol) was added followed by DIC (3.66 mL, 24 mmol). The mixture was stirred for 10 min, before addition to the resin, and another 30 mL NMP was added. The reaction was stirred for 2½ hour until a TNBS test was negative. The resin was drained and washed with NMP (4×70 mL) and DCM (10×70 mL) followed by ether (1×100 mL).

The dipeptide was cleaved from the resin by treating the resin with HOAc:TFE:DCM (1:2:7) (100 mL) for 30 min. The solvent was drained and collected and the resin was washed with DCM (50 mL). The combined filtrate was added water (150 mL), the layers were separated and the organic phase was dried with Na$_2$SO$_4$ and the solvents removed by evaporation to give a colorless oil. The oil containing residual NMP was re-dissolved in EtOAc (40 mL), washed 3 times with water (40 mL) and the organic phase was dried for 15 min with Na$_2$SO$_4$. Salts were filtered off and solvents removed in vacuo yielding the product as a white sticky foam (1.49 g, 84%).

LCMS method: LCMS_4: Rt: 4.38 min; Exact mass: 330.215 Da; M/1: 331.24

NMR method: $^1$H NMR (400 MHz, CDCl$_3$): δ9.48 (br, 1H), 6.97 (d, 1H), 4.15 (d, 1H), 2.82 (s, 3H), 2.25 (m, 2H), 1.47 (s, 9H), 0.92 (m, 9H), 0.86 (d, 3H)

B1.7b

2S)-2-[[(2S)-2-(tert-butoxycarbonylamino)-3-methyl-pentanoyl]amino]-3-methyl-butanoic acid (Boc-Ile-Val-OH H$_2$N-Val-O-chlorotrityl (~5.4 mmol) resin made as in Example B1.3 was swelled in DCM and drained. Boc-Ile-OH (5.55 g, 24 mmol) was dissolved in NMP (50 mL) and HOAt (3.26 g, 24 mmol) was added followed by DIC (3.66 mL, 24 mmol). The mixture was stirred for 10 min, before addition to the resin, and another 30 mL NMP was added. The reaction was stirred for 2% hour until a TNBS test was negative. The resin was drained and washed with NMP (4×70 mL) and DCM (10×70 mL) followed by ether (1×100 mL).

The dipeptide was cleaved from the resin by treating the resin with HOAc:TFE:DCM (1:2:7) (100 mL) for 30 min. The solvent was drained and collected and the resin was washed with DCM (50 mL). The combined filtrate was added water (150 mL), the layers were separated and the organic phase was dried with Na$_2$SO$_4$ and the solvents removed by evaporation to give a colorless oil. The oil containing residual NMP was re-dissolved in EtOAc (40 mL), washed 3 times with water (40 mL) and the organic phase was dried for 15 min with Na$_2$SO$_4$. Salts were filtered off and solvents removed in vacuo yielding the product as a white sticky foam (1.79 g, ~100%).

LCMS method: LCMS_4: Rt: 4.0 min, Exact mass: 330.215 Da; M/1: 331.24

NMR method: $^1$H NMR (400 MHz, CDCl$_3$): δ 8.30 (br, 1H), 6.91 (d, 1H), 5.40 (d, 1H), 4.60 (dd, 1H), 4.03 (t, 1H), 2.25 (m, 1H), 1.81 (br, 1H), 1.54 (br, 1H), 1.43 (s, 9H), 1.14 (m, 1H), 0.97 (d, 3H), 0.92 (m, 9H)

B1.8

2-[2-[2-[[2-[2-[2-[[(4S)-5-tert-butoxy-4-[10-(4-tert-butoxycarbonylphenoxy)decanoylamino]-5-oxo-pentanoyl]amino]ethoxy]ethoxy]-acetyl]amino]ethoxy]ethoxy]acetic acid Chem. 43

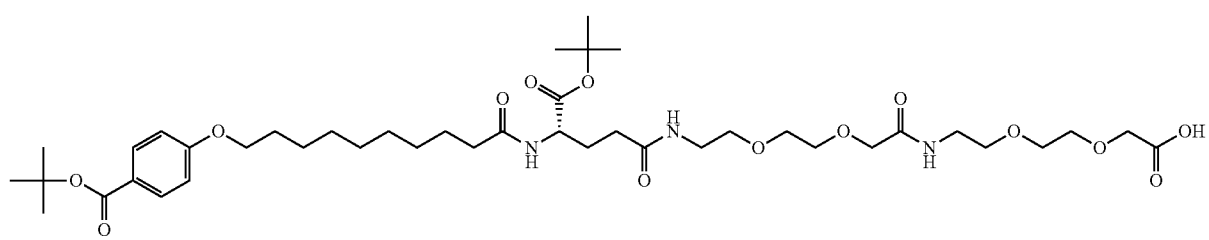

2-Chlorotrityl resin (7.70 g, 1.3 mmol/g, 10 mmol) was swelled for 20 min in DCM. Then a mixture of Fmoc-OEG-OH (19.27 g, 50 mmol) and DIPEA (8.5 mL) in DCM (100 mL) was added and the reaction was shaken for 2 hours. The resin was drained and washed with NMP (2×100 mL). The resin was then treated with a mixture of DCM, MeOH and DIPEA (80:15:5) (2×100 mL) (10 min each). After wash with NMP (3×100 mL) Fmoc-deprotection was made by standard procedure (2 min+18 min with 20% piperidine in NMP (100 ml each)). The resin was washed 6× with NMP.

Fmoc-OEG-OH (15.42 g, 40 mmol, 4 eq), HOAt (6.10 g, 40 mmol, 4 eq), and DIC (6.10 mL, 40 mmol, 4 eq) was mixed in DCM/NMP (1:1) (100 mL) and stirred for 10 minutes after which the mixture was added to the resin. After 15 min DIPEA (6.85 mL, 40 mmol, 4 eq) was added and the mixture was shaken for 2 h at room temperature.

The resin was drained and the resin was washed with NMP (6×100 mL). TNBS test was negative. Fmoc-deprotection was made by standard procedure (2 min+18 min with 20% piperidine in NMP (100 ml each)). The resin was washed 6× with NMP.

Fmoc-Glu-Otbu (12.70 g, 30 mmol, 3 eq), HOAt: (4.05 g, 30 mmol, 3 eq), and DIC (4.58 mL, 30 mmol, 3 eq) were mixed in DCM/NMP (1:1) (100 mL) and stirred for 10 minutes after which the mixture was added to the resin. After 15 min DIPEA (5.14 mL, 30 mmol, 3 eq) was added and the mixture was shaken for 3 h at room temperature. The resin was drained and the resin was washed with NMP (6×100 mL). TNBS test was negative.

Fmoc-deprotection was made by standard procedure (2 min+18 min with 20% piperidine in NMP (100 ml each)). The resin was washed 6× with NMP.

10-(4-tert-butoxycarbonylphenoxy)decanoic acid (10.94 g, 30 mmol, 3 eq), HOAt: (4.05 g, 30 mmol, 3 eq), and DIC (4.58 mL, 30 mmol, 3 eq) were mixed in DCM/NMP (1:1) (100 mL) and stirred for 10 minutes following which the mixture was added to the resin. The mixture was shaken for 3 hours at room temperature. TNBS test was negative.

The resin was then treated for 2 hours with a cleavage mixture of TFE (20 mL) and DCM (80 mL) following which the solution was drained into a roundbottomed flask 250 ml. Another 100 mL cleavage mixture was added to the resin and after shaking for 15 min the solution was combined with the first filtrate. The solvents were evaporated to give 6.94 g light brown oil.

The mixture was then dissolved in DCM, and purified by flash chromatography (gradient: 0-10% MeOH in DCM, flow 85 mL/min, 120 g silica column). Yield 2.40 g (29%)

LCMS method: LCMS_4: Rt: 3.48 min, exact mass: 839.478 Da; M/1: 840.56

NMR method: $^{1}$H-NMR (300 MHz, CDCl$_{3}$): δ 7.92 (dm, J=9.0 Hz, 2H); 7.37 (bs, 1H); 7.03 (bs, 1H); 6.86 (dm, J=8.9 Hz, 2H); 6.59 (d, J=7.7 Hz, 1H); 4.50-4.37 (m, 1H); 4.16 (s, 2H); 4.04-3.93 (m, 4H); 3.78-3.37 (m, 16H); 2.36-2.09 (m, 5H); 2.01-1.84 (m, 1H); 1.84-1.71 (m, 2H); 1.69-1.52 (m, 11H); 1.46 (s, 9H); 1.43-1.26 (m, 10H)

B2. Parent Drugs

B2.1

$N^{\epsilon 18}$-[2-[2-[2-[[2-[2-[2-[[(4S)-4-carboxy-4-[10-(4-carboxyphenoxyl)decanoylamino]butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-[10-(4-carboxyphenoxyl)decanoylamino]-butanoyl]amino]ethoxy]ethoxy]acetyl]amino]ethoxy]ethoxy]acetyl], $N^{\alpha 8}$-{3-[(2S)-2-hydroxy-3-(1H-imidazol-4-yl)propanoyl}-[Lys$^{18}$,Glu$^{22}$,Val$^{25}$,Arg$^{26}$,Lys$^{31}$,Gln$^{34}$]-GLP-1-(8-37)-peptide Chem. 21

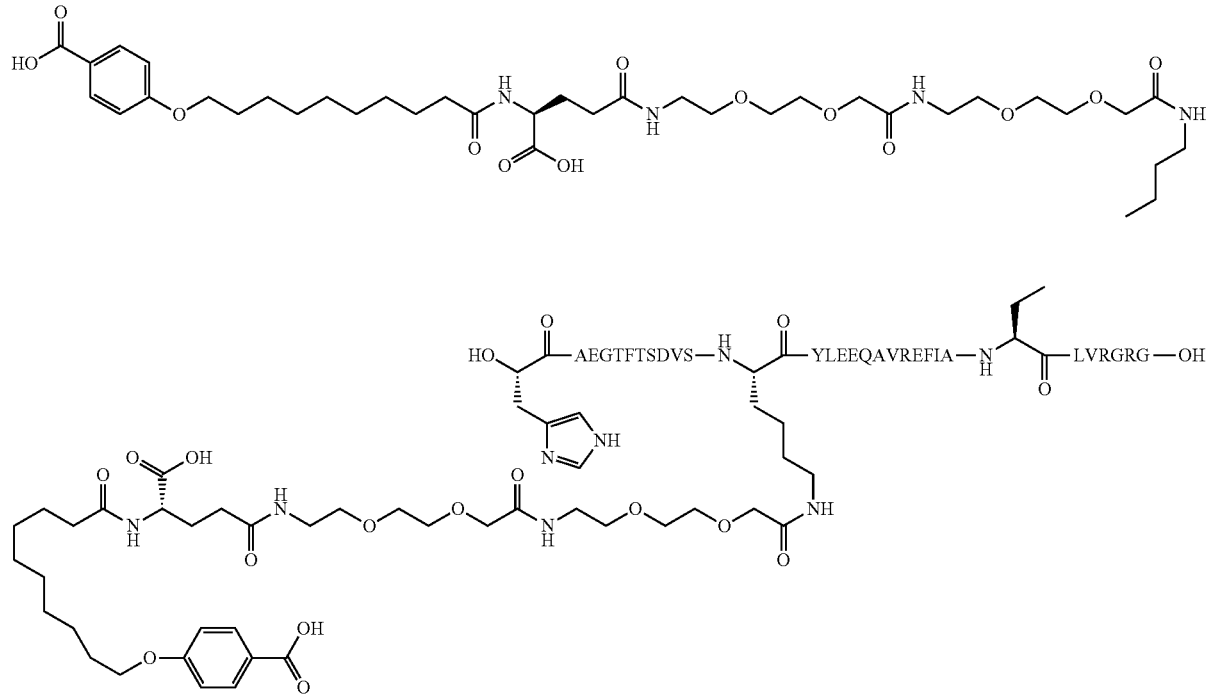

Fully protected [Lys$^{18}$,Glu$^{22}$,Val$^{25}$,Arg$^{26}$,Lys$^{31}$,Gln$^{34}$]-GLP-1-(9-37)-peptide was synthesised on Fmoc-Gly Wang LL resin according to general method SPPS_P leaving an Fmoc protected glutamic acid residue at the N-terminus.

The resin was further processed according to the general method: CP_M2.

The resulting fully protected peptide on resin was used for the synthesis of the compounds of Examples 1, 1a, 1b, 2, 2a, 3, and 3a.

The resin was cleaved and purified according to general method CP_M1 and the fractions containing the right compound were pooled and lyophilised to a white powder.

LCMS method: LCMS_4: Rt: 3.62 min; Exact mass: 4914.495 Da; M/5: 983.74; M/4: 1229.41; M/3: 1639.19

UPLC method: B4_1: Rt=8.42 min

UPLC method: B29_1: Rt=11.12 min

B2.2

N$^{\epsilon26}$-[2-[2-[2-[[2-[2-[2-[[(4S)-4-carboxy-4-[10-(4-carboxyphenoxyl)decanoylamino]butanoyl]amino] ethoxy]ethoxy]acetyl]amino]ethoxy]ethoxy]acetyl], N$^{\epsilon37}$-[2-[2-[2-[[2-[2-[2-[[(4S)-4-carboxy-4-[10-(4-carboxyphenoxyl)decanoylamino]-butanoyl]amino] ethoxy]ethoxy]acetyl]amino]ethoxy]ethoxy]acetyl], N$^{\alpha8}$-{3-[(2S)-2-hydroxy-3-(1H-imidazol-4-yl)propanoyl}-[Arg$^{34}$,Lys$^{37}$]-GLP-1-(8-37)-peptide

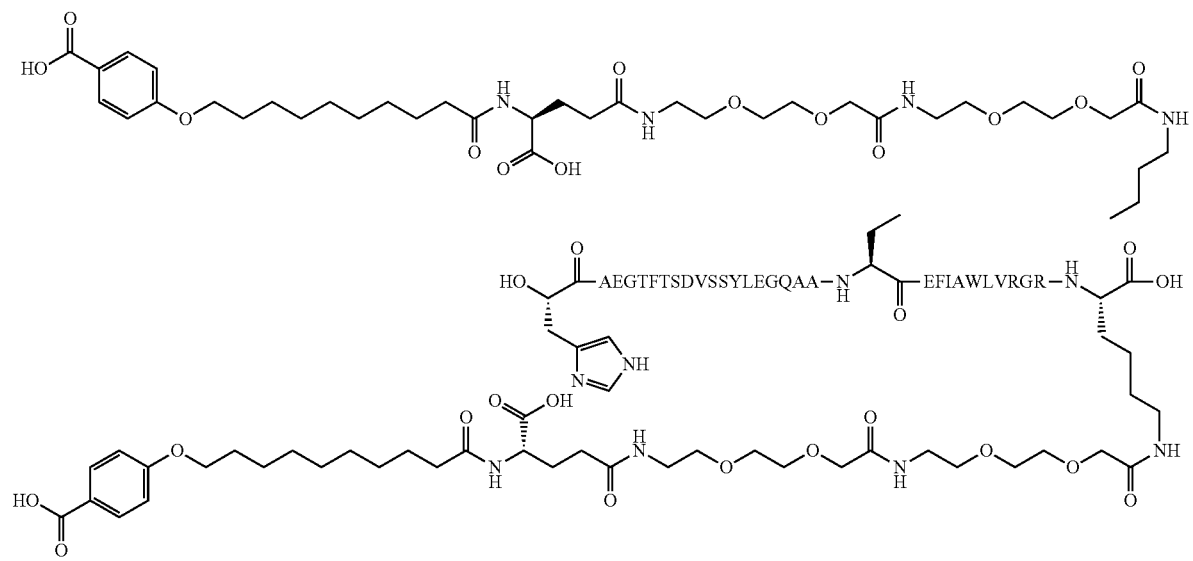

Chem. 22

Fully protected [Arg$^{34}$,Lys$^{37}$]-GLP-1-(9-37)-peptide was synthesised on Fmoc-Lys Wang LL resin according to general method SPPS_B leaving an Fmoc protected glutamic acid residue at the N-terminus.

The resin was further processed according to the general method: CP_M2.

The resulting fully protected peptide was used for the synthesis of the compounds of Example 4.

The resin was cleaved and purified according to general method CP_M1 and the fractions containing the right compound were pooled and lyophilised to a white powder.

LCMS method: LCMS_4: Rt: 2.27 min; Exact mass: 4872.416 Da; M/4: 1219.43; M/3: 1625.52

UPLC method: B4_1: Rt=8.75 min

UPLC method: B29_1: Rt=11.86 min

B2.3

$N^{\epsilon 18}$-[2-[2-[2-[[2-[2-[2-[[(4S)-4-carboxy-4-[10-(4-carboxyphenoxyl)decanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[10-(4-carboxyphenoxyl)decanoylamino]-butanoyl]amino]ethoxy]ethoxy]acetyl]amino]ethoxy]ethoxy]acetyl], $N^{\alpha 8}$-{3-[(2S)-2-hydroxy-3-(1H-imidazol-4-yl)propanoyl]}-[Lys$^{18}$,Glu$^{22}$,Gln$^{34}$]-GLP-1-(8-37)-peptide Chem. 23

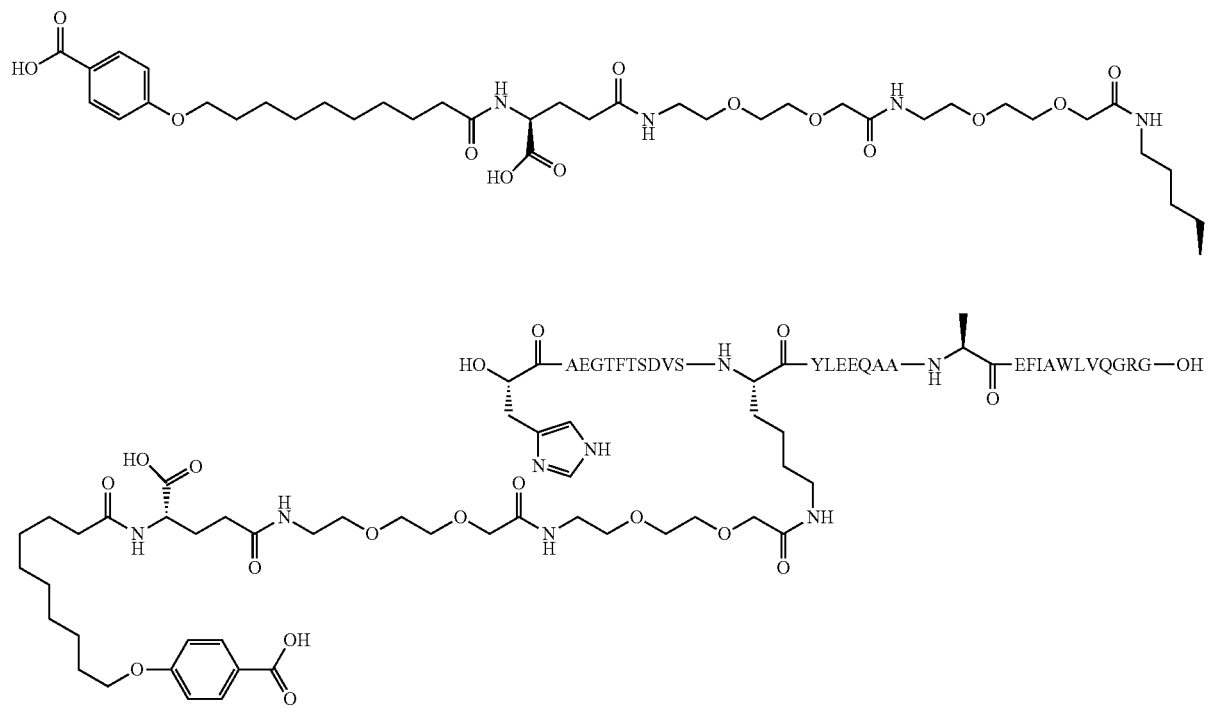

Fully protected [Lys$^{18}$,Glu$^{22}$,Gln$^{34}$]-GLP-1-(9-37)-peptide was synthesised on Fmoc-Gly Wang LL resin according to general method SPPS_B leaving an Fmoc protected glutamic acid residue at the N-terminus.

The resin was further processed according to the general method: CP_M2. The resulting fully protected peptide was used for the synthesis of the compound of Example 5.

The resin was cleaved and purified according to general method CP_M1 and the fractions containing the right compound were pooled and lyophilised to a white powder.

LCMS method: LCMS_4: Rt: 2.37 min; Exact mass: 4886.384 Da; M/4: 1222.92, M/3: 1630.50

UPLC method: B4_1: Rt=8.93 min

UPLC method: B29_1: Rt=12.36 min

B2.4

N^ε27 [(S)-(22,40-dicarboxy-10,19,24-trioxo-3,6,12,15-tetraoxa-9,18,23-triazatetracontan-1-oyl)]-N^α8-{3-[(2S)-2-hydroxy-3-(1H-imidazol-4-yl)propanoyl}-Aib⁸,Glu²²,Arg²⁶,Lys²⁷,Arg³⁴]-GLP-1-(8-37)-peptide Chem. 24

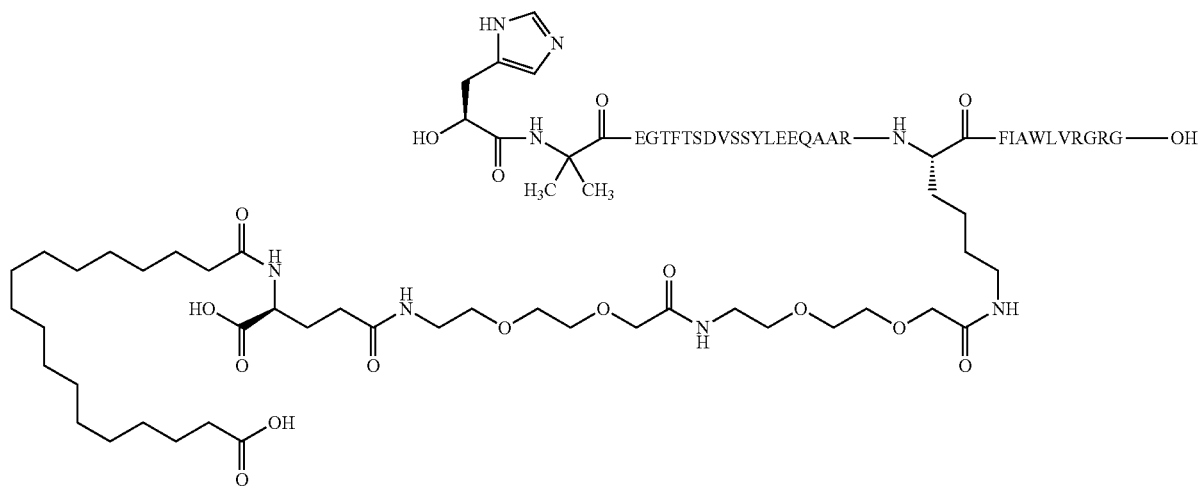

Step 1. Fully Protected Peptide Back Bone Synthesis
Fully protected [Glu²²,Arg²⁶,Lys²⁷,Arg³⁴]-GLP-1-(9-37)-peptide was synthesised on Fmoc-Gly Wang LL resin according to general method SPPS_B leaving an Fmoc protected Glu residue at the N-terminus.

Step 2. ε-Lys Mtt Deprotection:
The ε-Lys Mtt protecting group were removed by treatment with 0.5% TFA in DCM for 5 min followed by 3 times 15 min with neet hexafluoroisopropanol. The resin was washed with 6 times with DCM and 6 times with NMP. TNBS test was positive.

Step 3. Sidechain Coupling:
Bis-t-Butyl protected side chain (17-((S)-1-tert-butoxycarbonyl-3-{2-[-2-({2-[2-(2,5-dioxopyrrolidin-1-yloxycarbonylmethoxy)ethoxy]ethylcarbamoyl}methoxy)ethoxy]ethylcarbamoyl}propylcarbamoyl)heptadecanoic acid tert-butyl ester)(4 molar equivalents compared to resin) was dissolved in NMP and pre-activated with TBTU (3.8 eq), HOBt (4 eq), and DIPEA (4 eq) for 15 min., then added to the resin and reacted over night or until TNBS test showed clear beads.

Step 4. Fmoc Removal:
The Fmoc protecting group on the terminal Glu was removed by treatment with 20% piperidine in NMP for 2 min+18 min followed by 6 times wash with NMP.

Step 2. Coupling of Fmoc-Aib-OH:
Fmoc-Aib-OH (4 molar equivalents compared to resin) was dissolved in NMP and activated with Oxyma (4.0 eq), DIC (4 eq) for 15 minutes, then added to the resin and coupled overnight until negative TNBS test. The resin was washed 6 times with NMP and 10 times with DCM.

Step 5. L-β-Imidazolelactic Acid Coupling:
L-beta-Imidazolelactic acid (4 molar equivalents compared to resin) was dissolved in NMP and activated with PyBOB (3.8 eq), HOBt (4 eq), and TEA (4 eq) for 10 minutes before added to the resin and coupling for 1.5 h. The coupling was repeated 3 times.

The resin was cleaved and purified according to general method CP_M1 and the fractions containing the right compound were pooled and lyophilised to a white powder.

LCMS method: LCMS_4: Rt: 2.25 min; Exact mass: 4211.179 Da; M/4: 1053.78, M/3: 1404.74

UPLC method: B4_1: Rt=8.73 min

UPLC method: B29_1: Rt=14.56 min

B2.5

N^ε26 [(S)-(22,40-dicarboxy-10,19,24-trioxo-3,6,12,15-tetraoxa-9,18,23-triazatetracontan-1-oyl)]-N^α8-{3-[(2S)-2-hydroxy-3-(1H-imidazol-4-yl)propanoyl}-Aib⁸,Arg²³,Arg³⁴]-GLP-1-(8-37)-peptide Chem. 25

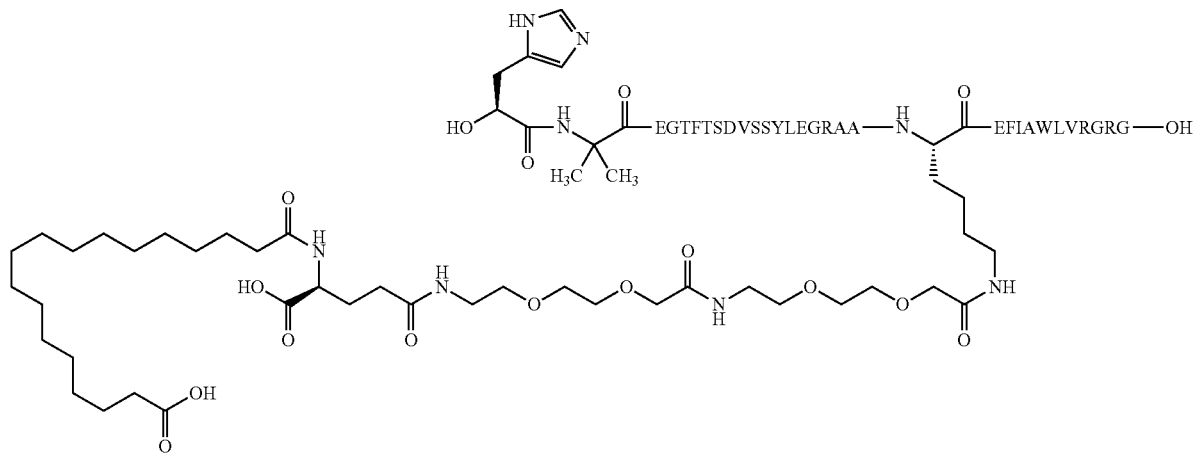

Step 1. Fully Protected Peptide Back Bone Synthesis:
Fully protected Aib⁸,Arg²³,Arg³⁴]-GLP-1-(8-37)-peptide was synthesised on Fmoc-Gly Wang LL resin according to general method SPPS_P leaving an Fmoc protected Aib residue at the N-terminus.

Step 2. Fmoc Removal:
The Fmoc protecting group on the terminal Glu was removed by treatment with 20% piperidine in NMP for 2 min+18 min followed by 6 times wash with NMP.

Step 3. L-Beta-Imidazolelactic Acid Coupling:
L-beta-Imidazolelactic acid (4 molar equivalents compared to resin) was dissolved in NMP and activated with PyBOB (3.8 eq), HOBt (4 eq), and TEA (4 eq) for 10 minutes before added to the resin and coupling for 1.5 h. The coupling was repeated 2 times.

Step 4. Cleavage from the Resin:
The resin was washed with NMP and DCM, and the peptide was cleaved from the resin by a 2.5 hour treatment with TFA/TIS/water (95:2.5:2.5) followed by precipitation of the crude peptide with diethylether.

Step 5. Side Chain Acylation:
The crude peptide was dissolved water and NaOH (1 N, aq) was added dropwise until total dissolution of the peptide and pH 10.6.

With an autotitrator pH was kept constant at pH 11.3 by addition of dilute NaOH (0.1 M, aq).

NHS activated sidechain (Example 7 of WO 2009/083549) 17-((S)-1-Carboxy-3-{2-[2-({2-[2-(2,5-dioxo-pyrrolidin-1-yloxycarbonylmethoxy)-ethoxy]ethylcarbamoyl}-methoxy)-ethoxy]-ethylcarbamoyl}-propylcarbamoyl)-heptadecanoic acid (1.2 eq) sidechain was dissolved in DMF and added dropwise to the solution. After 1 h the reaction mixture was quenched by adding 1 volume of acetic acid.

Step 6. Purification:
The peptide was purified by standard RP-HPLC on a C18, 5 μM column using acetonitrile/water/TFA. The fractions were analysed by a combination of UPLC, and LC-MS methods, and the appropriate fractions were pooled and lyophilised.

LCMS method: LCMS_4: Rt: 2.22 min; Exact mass: 4140.142 Da; M/4: 1036.03, M/3: 1381.36

UPLC method: B4_1: Rt=8.80 min

UPLC method: B29_1: Rt=14.76 min

B3. Specific Examples

Example 1

N^ε18^-[2-[2-[2-[[2-[2-[2-[[(4S)-4-carboxy-4-[10-(4-carboxyphenoxyl)decanoylamino]butanoyl]amino]ethoxy]ethoxy]acetyl]amino]ethoxy]ethoxy]acetyl], N^ε31^-[2-[2-[2-[[2-[2-[2-[[(4S)-4-carboxy-4-[10-(4-carboxyphenoxyl)decanoylamino]-butanoyl]amino]ethoxy]ethoxy]acetyl]amino]ethoxy]ethoxy]acetyl], N^α8^-{(2S)-3-(1H-imidazol-4-yl)-2-[(2S)-3-methyl-2-[[2-(methylamino)acetyl]amino]butanoyl]oxy-propanoyl}-[Lys$^{18}$,Glu$^{22}$,Val$^{25}$,Arg$^{28}$,Lys$^{31}$,Gln$^{34}$]-GLP-1-(8-37)-peptide

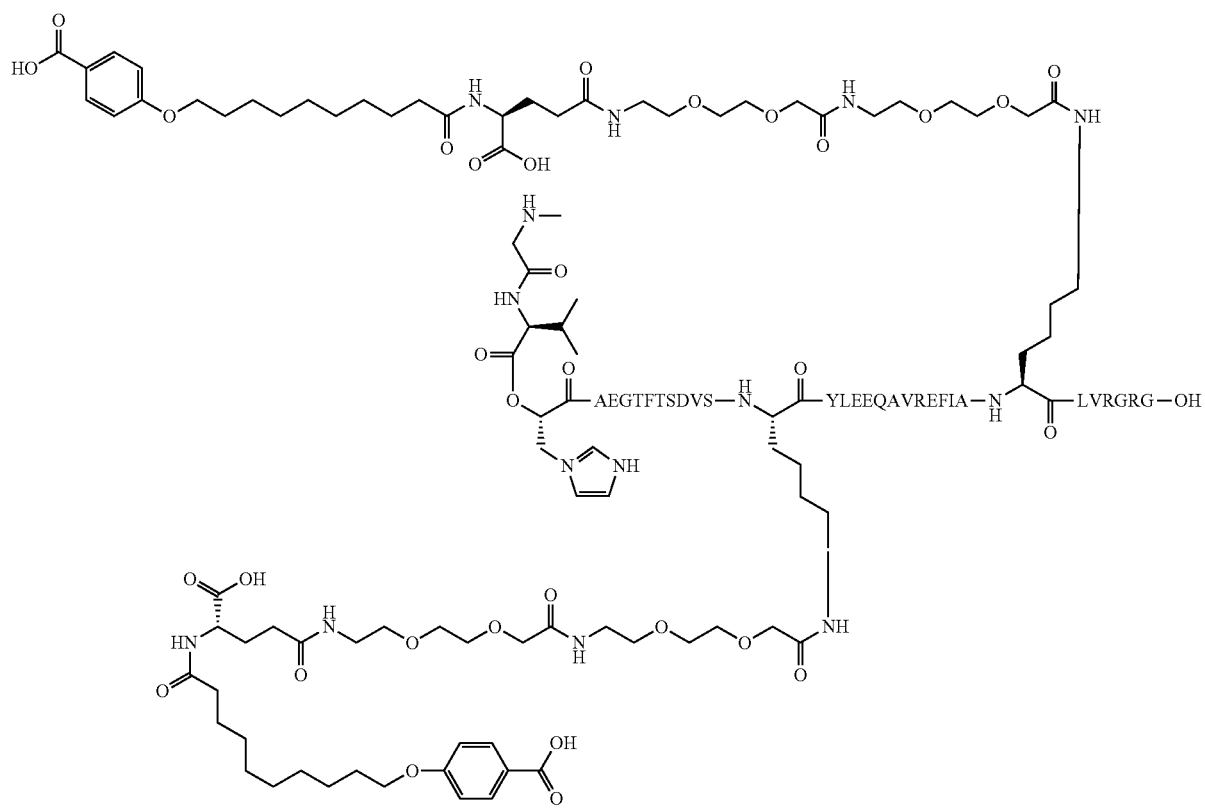

Chem. 51

Fully protected [Lys$^{18}$,Glu$^{22}$,Val$^{25}$,Arg$^{26}$,Lys$^{31}$,Gln$^{34}$]-GLP-1-(9-37)-peptide (i.e., SEQ ID NO: 1 in which Ala$^8$ is deleted, and the amino acids at positions 18, 22, 25, 26, 31, and 34 have been substituted with Lys$^{18}$,Glu$^{22}$,Val$^{25}$, Arg$^{26}$,Lys$^{31}$, and Gln$^{34}$, respectively) was synthesised on Fmoc-Gly Wang LL resin according to general method SPPS_P leaving an Fmoc protected glutamic acid residue at the N-terminus.

The resin was further processed according to the general method: CP_M2.

For coupling of Boc-NMe-Gly-Val-OH, Boc-N-Me-Gly-Val-OH (6 molar equivalents compared to resin) was dissolved in DCM. MSNT (6 eq) was added followed by methylimidazol (9 eq). The mixture was allowed to stand for 10 minutes after which it was added to the resin prepared above. The resin was shaken for 4 h, then drained and washed 6 times with DCM.

The resin was cleaved and purified according to general method CP_M1 and the fractions containing the right compound were pooled and lyophilised to a white powder.

LCMS method: LCMS_4: Rt: 2.05 min; Exact mass: 5082.585 Da; M/5: 1017.75; M/4: 1271.98

UPLC method: B4_1: Rt=8.09 min

UPLC method: B29_1: Rt=11.20 min

Comparative Example 1a

N^ε18-[2-[2-[2-[[2-[2-[2-[[(4S)-4-carboxy-4-[10-(4-carboxyphenoxyl)decanoylamino]butanoyl]amino]ethoxy]ethoxy]acetyl]amino]ethoxy]ethoxy]acetyl], N^ε31-[2-[2-[2-[[2-[2-[2-[[(4S)-4-carboxy-4-[10-(4-carboxyphenoxyl)decanoylamino]-butanoyl]amino]ethoxy]ethoxy]acetyl]amino]ethoxy]ethoxy]acetyl], N^α8-{(2S)-2-[(2S)-2-[(2-aminoacetyl)amino]-3-methyl-butanoyl]oxy-3-(1H-imidazol-4-yl)propanoyl}-}-[Lys^18,Glu^22,Val^25,Arg^28,Lys^31,Gln^34]-GLP-1-(8-37)-peptide

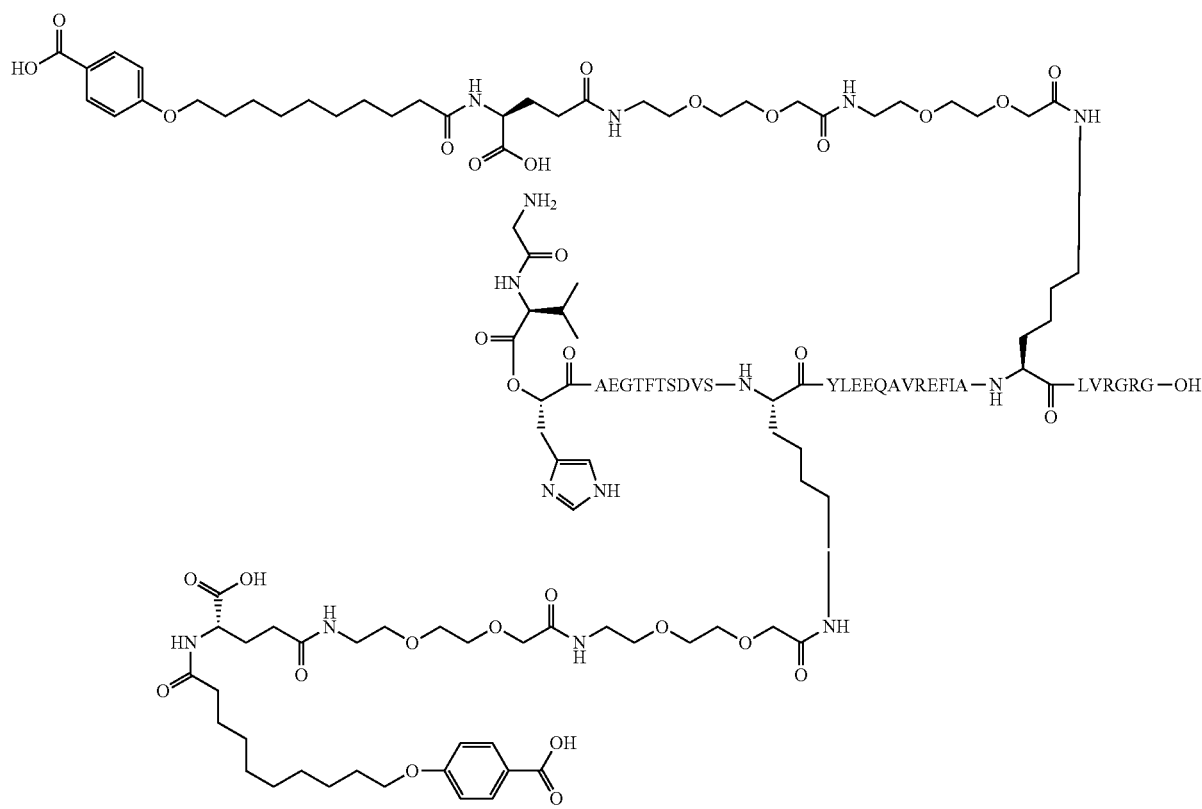

Chem. 30

Fully protected [Lys^18,Glu^22,Val^25,Arg^28,Lys^31,Gln^34]-GLP-1-(9-37)-peptide (i.e., SEQ ID NO: 1 in which Ala^8 is deleted, and the amino acids at positions 18, 22, 25, 26, 31, and 34 have been substituted with Lys^18,Glu^22,Val^25,Arg^28, Lys^31, and Gln^34, respectively) was synthesised on Fmoc-Gly Wang LL resin according to general method SPPS_A leaving an Fmoc protected glutamic acid residue at the N-terminus.

The resin was further processed according to the general method: CP_M2.

For coupling of Boc-Gly-Val-OH, Boc-Gly-Val-OH (6 molar equivalents compared to resin) was dissolved in DCM. MSNT (6 eq) was added followed by methylimidazol (9 eq). The mixture was allowed to stand for 10 minutes after which it was added to the resin prepared above. The resin was shaken for 4 h, then drained and washed 6 times with DCM.

The resin was cleaved and purified according to standard method CP_M1 and the fractions containing the right compound were pooled and lyophilised to a white powder.

LCMS method: LCMS_4: Rt: 2.36 min; Exact mass: 5068.5696 Da; M/5: 1014.97; M/4: 1268.46.

UPLC method: B4_1: Rt=9.35 min

UPLC method: B29_1: Rt=9.10 min

Comparative Example 1b

N^ε18^-[2-[2-[2-[[2-[2-[2-[[(4S)-4-carboxy-4-[10-(4-carboxyphenoxyl)decanoylamino]butanoyl]amino]ethoxy]ethoxy]acetyl]amino]ethoxy]ethoxy]acetyl], N^ε31^-[2-[2-[2-[[2-[2-[2-[[(4S)-4-carboxy-4-[10-(4-carboxyphenoxyl)decanoylamino]-butanoyl]amino]ethoxy]ethoxy]acetyl]amino]ethoxy]ethoxy]acetyl], N^α8^-{(2S)-2-[(2S)-2-[(2-hydroxyacetyl)amino]-3-methyl-butanoyl]oxy-3-(1H-imidazol-4-yl)propanoyl}-[Lys$^{18}$,Glu$^{22}$,Val$^{25}$,Arg$^{28}$,Lys$^{31}$,Gln$^{34}$]-GLP-1-(8-37)-peptide

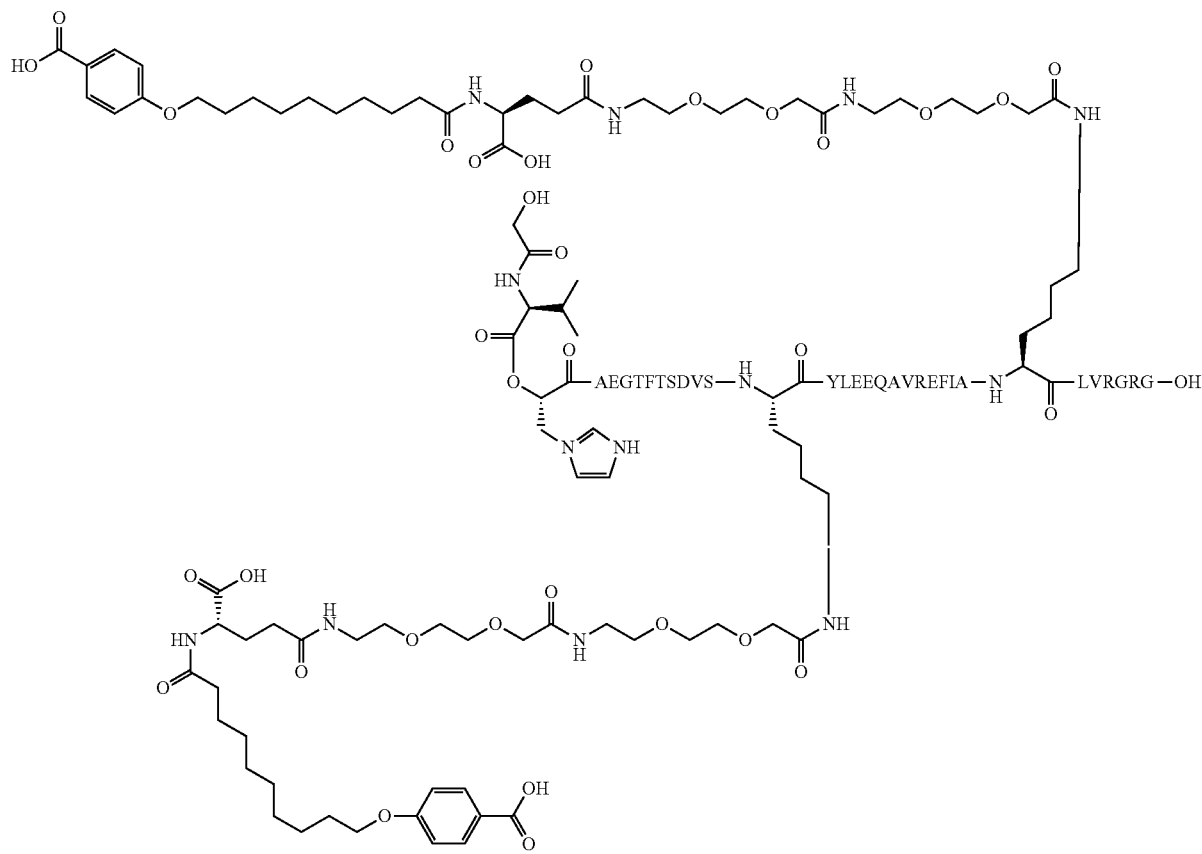

Chem. 31

Fully protected [Lys$^{18}$,Glu$^{22}$,Val$^{25}$,Arg$^{28}$,Lys$^{31}$,Gln$^{34}$]-GLP-1-(9-37)-peptide (i.e., SEQ ID NO: 1 in which Ala$^8$ is deleted, and the amino acids at positions 18, 22, 25, 26, 31, and 34 have been substituted with Lys$^{18}$,Glu$^{22}$,Val$^{25}$,Arg$^{28}$, Lys$^{31}$, and Gln$^{34}$, respectively) was synthesised on Fmoc-Gly Wang LL resin according to general method SPPS_A leaving an Fmoc protected glutamic acid residue at the N-terminus.

The resin was further processed according to the general method: CP_M2.

For coupling of tBuMe$_2$SiOCH$_2$—C(O)-Val-OH, (S)-2-[2-(tert-Butyl-dimethyl-silanyloxy)-acetylamino]-3-methyl-butyric acid (6 molar equivalents compared to resin) was dissolved in DCM. MSNT (6 eq) was added followed by methylimidazol (9 eq). The mixture was allowed to stand for 10 minutes after which it was added to the resin prepared above. The resin was shaken for 4 h, then drained and washed 6 times with DCM.

The resin was cleaved and purified according to the general method CP_M1 and the fractions containing the right compound were pooled and lyophilised to a white powder.

LCMS method: LCMS_4: Rt: 3.67 min; Exact mass: 5071.569 Da; M/4: 1268.71; M/3: 1692.23

UPLC method: B4_1: Rt=8.69 min

UPLC method: B29_1: Rt=9.51 min

Example 2

N^ε18-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl],
N^ε31-[2-[2-[2-[[2-[2-[2-[[(4S)-4-carboxy-4-[10-(4-carboxyphenoxyl)decanoylamino]-butanoyl]amino]ethoxy]ethoxy]acetyl]amino]ethoxy]ethoxy]acetyl],
N^α8-{(S)-3-(1H-Imidazol-4-yl)-2-[(S)-3-methyl-2-((S)-3-methyl-2-methylamino-butyrylamino)-butyryloxy]-propionyl}-[Lys$^{18}$,Glu$^{22}$,Val$^{25}$,Arg$^{28}$,Lys$^{31}$,Gln$^{34}$]-GLP-1-(8-37)-peptide Chem. 52

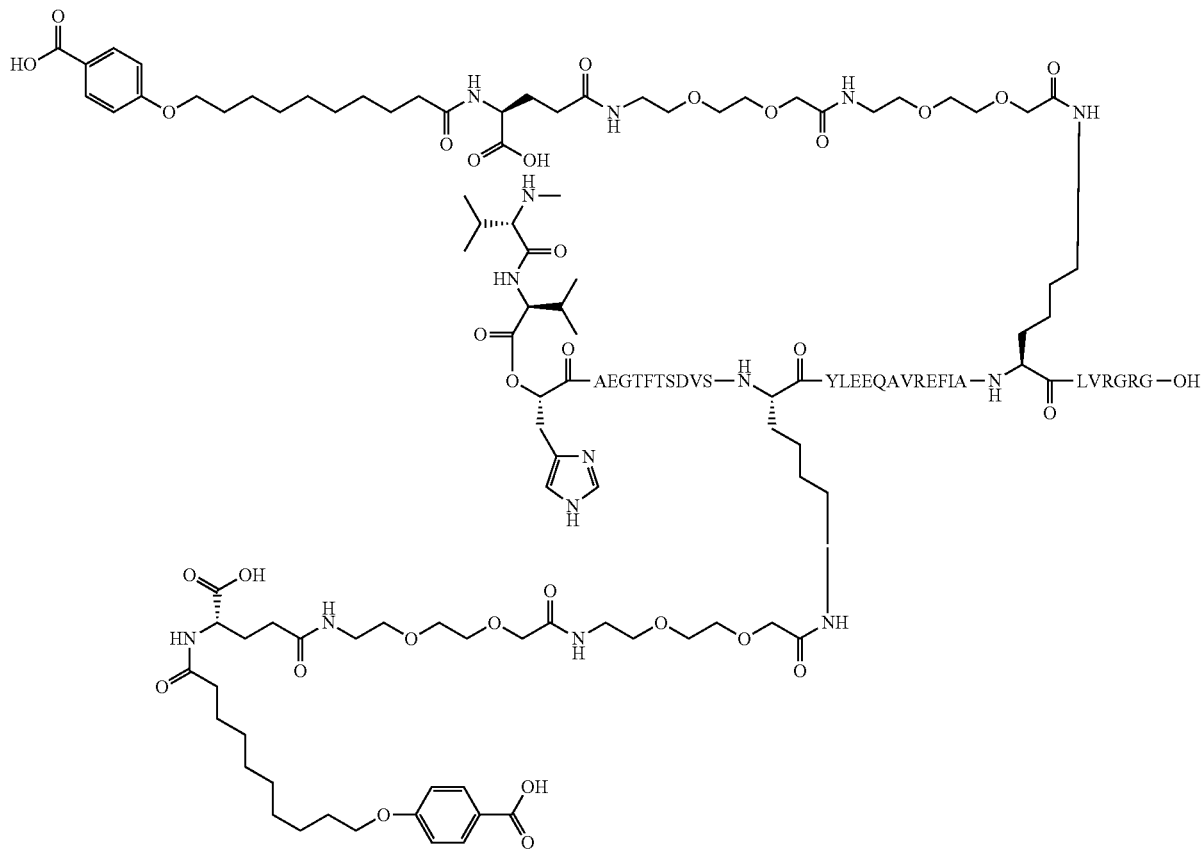

Fully protected [Lys$^{18}$,Glu$^{22}$,Val$^{25}$,Arg$^{28}$,Lys$^{31}$,Gln$^{34}$]-GLP-1-(9-37)-peptide (i.e., SEQ ID NO: 1 in which Ala$^8$ is deleted, and the amino acids at positions 18, 22, 25, 26, 31, and 34 have been substituted with Lys$^{18}$,Glu$^{22}$,Val$^{25}$,Arg$^{28}$, Lys$^{31}$, and Gln$^{34}$, respectively) was synthesized on Fmoc-Gly Wang LL resin according to standard method SPPS_P leaving an Fmoc protected glutamic acid residue at the N-terminus.

The resin was further processed according to the general method: CP_M2.

For coupling of Boc-N-Me-Val-Val-OH, Boc-N-Me-Val-Val-OH (6 molar equivalents compared to resin) was dissolved in DCM. MSNT (6 eq) was added followed by methylimidazol (9 eq). The mixture was allowed to stand for 10 minutes after which it was added to the resin prepared above. The resin was shaken for 4 h, then drained and washed 6 times with DCM.

The resin was cleaved and purified according to the general method CP_M1 and the fractions containing the right compound was pooled and lyophilized to a white powder.

LCMS method: LCMS_4: Rt: 2.12 min; Exact mass: 5124.632 Da; M/5: 1025.93; M/4: 1282.15

UPLC method: B4_1: Rt=8.07 min

Comparative Example 2a

N^ε18-[2-[2-[2-[[2-[2-[2-[[(4S)-4-carboxy-4-[10-(4-carboxyphenoxyl)decanoylamino]butanoyl]amino]ethoxy]ethoxy]acetyl]amino]ethoxy]ethoxy]acetyl], N^ε31-[2-[2-[2-[[2-[2-[2-[[(4S)-4-carboxy-4-[10-(4-carboxyphenoxyl)decanoylamino]-butanoyl]amino]ethoxy]ethoxy]acetyl]amino]ethoxy]ethoxy]acetyl], N^α8-{(2S)-2-[(2S)-2-[[(2S)-2-amino-3-methyl-butanoyl]amino]-3-methyl-butanoyl]oxy-3-(1H-imidazol-4-yl)propanoyl}-[Lys$^{18}$,Glu$^{22}$,Val$^{25}$,Arg$^{28}$,Lys$^{31}$,Gln$^{34}$]-GLP-1-(8-37)-peptide Chem. 32

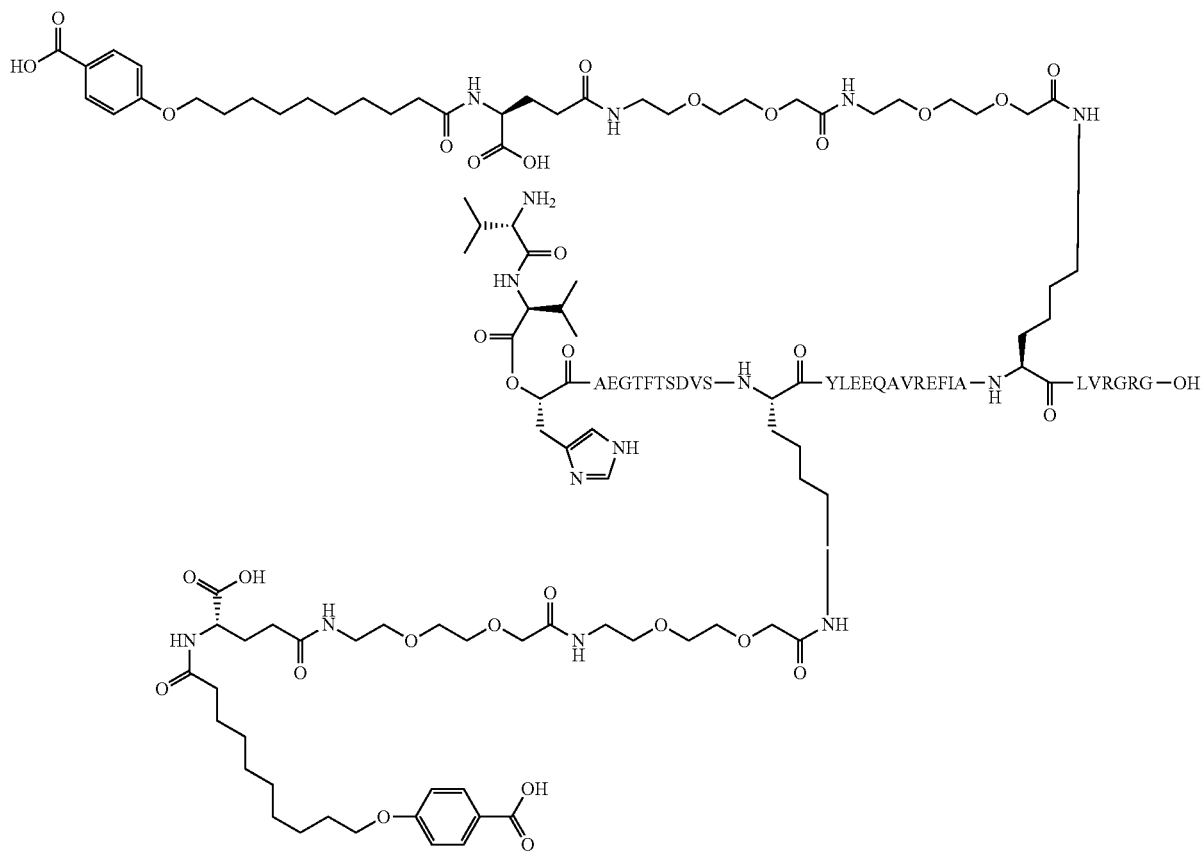

Fully protected [Lys$^{18}$,Glu$^{22}$,Val$^{25}$,Arg$^{28}$,Lys$^{31}$,Gln$^{34}$]-GLP-1-(9-37)-peptide (i.e., SEQ ID NO: 1 in which Ala$^8$ is deleted, and the amino acids at positions 18, 22, 25, 26, 31, and 34 have been substituted with Lys$^{18}$,Glu$^{22}$,Val$^{25}$,Arg$^{26}$, Lys$^{31}$, and Gln$^{34}$, respectively) was synthesised on Fmoc-Gly Wang LL resin according to general method SPPS_B leaving an Fmoc protected glutamic acid residue at the N-terminus.

The resin was further processed according to the general method: CP_M2.

For coupling of Boc-Val-Val-OH, Boc-Val-Val-OH (6 molar equivalents compared to resin) was dissolved in DCM. MSNT (6 eq) was added followed by methylimidazol (9 eq). The mixture was allowed to stand for 10 minutes after which it was added to the resin prepared above. The resin was shaken for 4 h, then drained and washed 6 times with DCM.

The resin was cleaved and purified according to general method CP_M1 and the fractions containing the right compound were pooled and lyophilised to a white powder.

LCMS method: LCMS_4: Rt: 2.05 min; Exact mass: 5110.617 Da; M/5: 1023.37; M/4: 1278.99

UPLC method: B2_1: Rt=12.41 min

UPLC method: B29_1: Rt=11.13 min

Example 3

N$^{\epsilon18}$-[2-[2-[2-[[2-[2-[2-[[(4S)-4-carboxy-4-[10-(4-carboxyphenoxyl)decanoylamino]butanoyl]amino]ethoxy]ethoxy]acetyl]amino]ethoxy]ethoxy]acetyl],
N$^{\epsilon31}$-[2-[2-[2-[[2-[2-[2-[[(4S)-4-carboxy-4-[10-(4-carboxyphenoxyl)decanoylamino]-butanoyl]amino]ethoxy]ethoxy]acetyl]amino]ethoxy]ethoxy]acetyl],
N$^{\alpha8}$-{(S)-3-(1H-imidazol-4-yl)-2-[(S)-3-methyl-2-((S)-3-methyl-2-methylamino-pentanoylamino)-butyryloxy]-propionyl}-[Lys$^{18}$,Glu$^{22}$,Val$^{25}$,Arg$^{28}$, Lys$^{31}$,Gln$^{34}$]-GLP-1-(8-37)-peptide

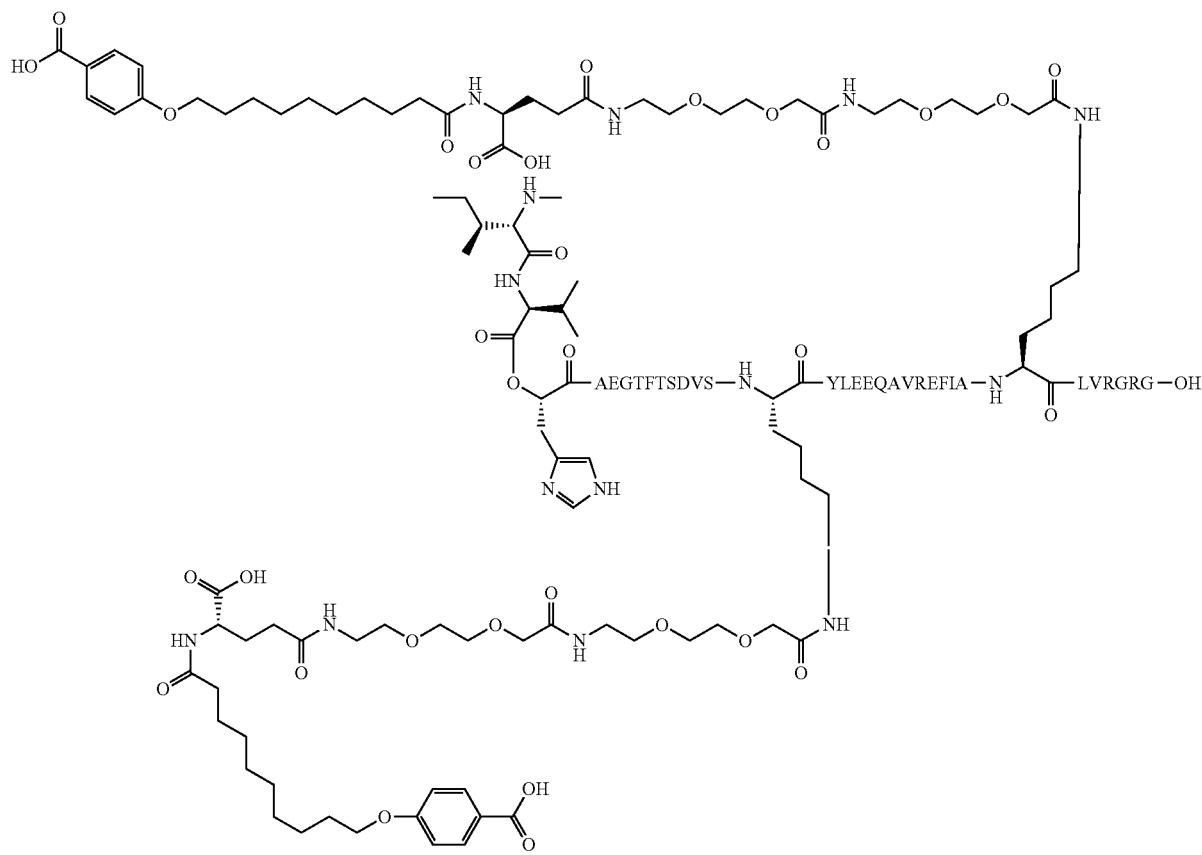

Chem. 53

Fully protected [Lys$^{18}$,Glu$^{22}$,Val$^{25}$,Arg$^{28}$,Lys$^{31}$,Gln$^{34}$]-GLP-1-(9-37)-peptide (i.e., SEQ ID NO: 1 in which Ala$^8$ is deleted, and the amino acids at positions 18, 22, 25, 26, 31, and 34 have been substituted with Lys$^{18}$,Glu$^{22}$,Val$^{25}$,Arg$^{28}$, Lys$^{31}$, and Gln$^{34}$, respectively) was synthesised on Fmoc-Gly Wang LL resin according to general method SPPS_P leaving an Fmoc protected glutamic acid residue at the N-terminus.

The resin was further processed according to the general method: CP_M2.

For coupling of Boc-N-Me-Ile-Val-OH, Boc-N-Me-Ile-Val-OH (6 molar equivalents compared to resin) was dissolved in DCM. MSNT (6 eq) was added followed by methylimidazol (9 eq). The mixture was allowed to stand for 10 minutes after which it was added to the resin prepared above. The resin was shaken for 4 h, then drained and washed 6 times with DCM.

The resin was cleaved and purified according to general method CP_M1 and the fractions containing the right compound was pooled and lyophilised to a white powder.

LCMS method: LCMS_4: Rt: 2.05 min; Exact mass: 5140.666 Da; M/5: 1028.97; M/4: 1286.00

UPLC method: B2_1: Rt=12.37 min

UPLC method: B29_1: Rt=11.22 min

Comparative Example 3a $N^{\epsilon 18}$-[2-[2-[2-[[2-[2-[2-[[(4S)-4-carboxy-4-[10-(4-carboxyphenoxyl)decanoylamino]butanoyl]amino]ethoxy]ethoxy]acetyl]amino]ethoxy]ethoxy]acetyl], $N^{\epsilon 31}$-[2-[2-[2-[[2-[2-[2-[[(4S)-4-carboxy-4-[10-(4-carboxyphenoxyl)decanoylamino]-butanoyl]amino]ethoxy]ethoxy]acetyl]amino]ethoxy]ethoxy]acetyl], $N^{\alpha 8}$-{(S)-2-[(S)-2-((S)-2-amino-3-methyl-pentanoylamino)-3-methyl-butyryloxy]-3-(1H-imidazol-4-yl)-propionyl}-[Lys$^{18}$,Glu$^{22}$,Val$^{25}$,Arg$^{28}$,Lys$^{31}$,Gln$^{34}$]-GLP-1-(8-37)-peptide

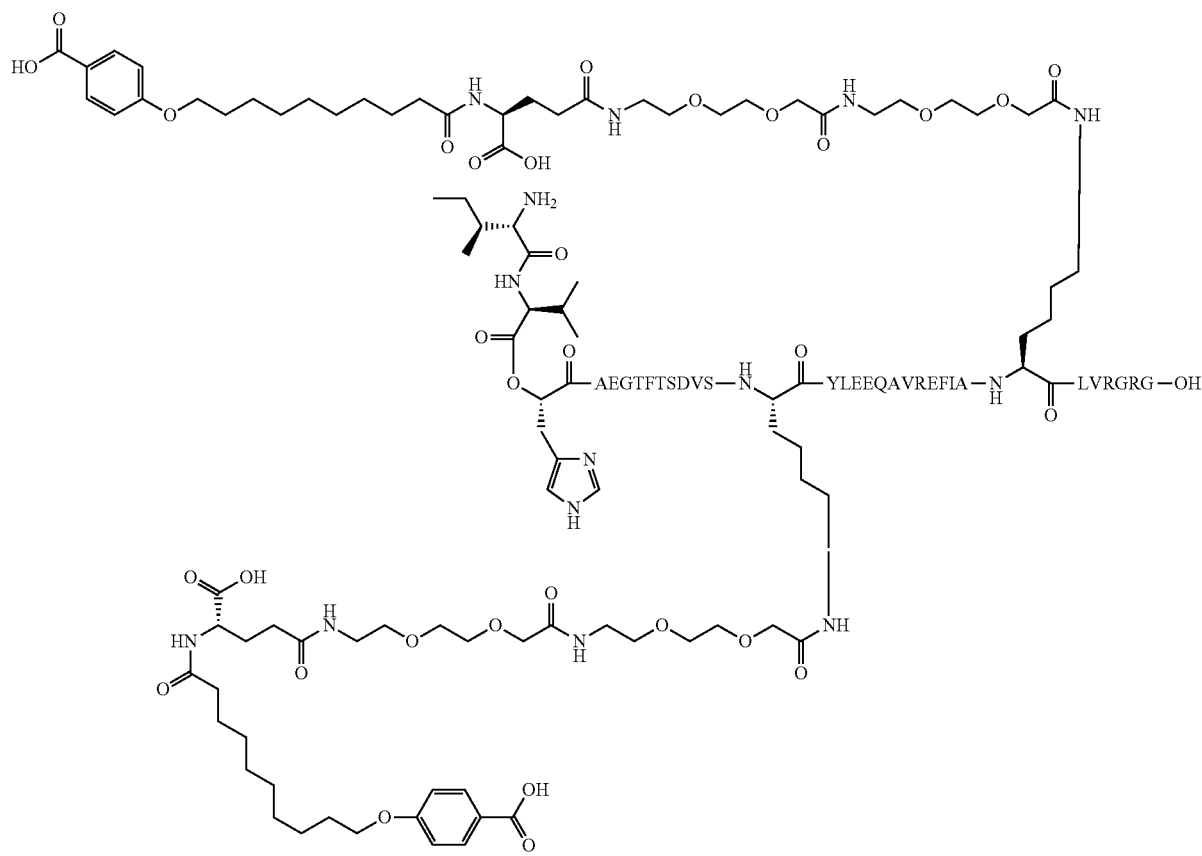

Chem. 33

Fully protected [Lys$^{18}$,Glu$^{22}$,Val$^{25}$,Arg$^{26}$,Lys$^{31}$,Gln$^{34}$]-GLP-1-(9-37)-peptide (i.e., SEQ ID NO: 1 in which Ala$^8$ is deleted, and the amino acids at positions 18, 22, 25, 26, 31, and 34 have been substituted with Lys$^{18}$, Glu$^{22}$, Val$^{25}$, Arg$^{26}$, Lys$^{31}$, and Gln$^{34}$, respectively) was synthesized on Fmoc-Gly Wang LL resin according to standard method SPPS_P leaving an Fmoc protected glutamic acid residue at the N-terminus.

The resin was further processed according to the general method: CP_M2.

For coupling of Boc-Ile-Val-OH, Boc-Ile-Val-OH (6 molar equivalents compared to resin) was dissolved in DCM. MSNT (6 eq) was added followed by methylimidazol (9 eq). The mixture was allowed to stand for 10 minutes after which it was added to the resin prepared above. The resin was shaken for 4 h, then drained and washed 6 times with DCM.

The resin was cleaved and purified according to the general method CP_M1 and the fractions containing the right compound was pooled and lyophilized to a white powder.

LCMS method: LCMS_4: Rt: 2.10 min; Exact mass: 5124.632 Da; M/5: 1025.93; M/4: 1282.15

UPLC method: B4_1: Rt=8.07 min

Example 4

N^ε26^-[2-[2-[2-[[2-[2-[2-[[(4S)-4-carboxy-4-[10-(4-carboxyphenoxyl)decanoylamino]butanoyl]amino]ethoxy]ethoxy]acetyl]amino]ethoxy]ethoxy]acetyl], N^ε37^-[2-[2-[2-[[2-[2-[2-[[(4S)-4-carboxy-4-[10-(4-carboxyphenoxyl)decanoylamino]-butanoyl]amino]ethoxy]ethoxy]acetyl]amino]ethoxy]ethoxy]acetyl], N^α8^-{(S)-3-(1H-imidazol-4-yl)-2-[(S)-3-methyl-2-((S)-3-methyl-2-methylamino-pentanoylamino)-butyryloxy]-propionyl}-[Arg^34^,Lys^37^]-GLP-1-(8-37)-peptide

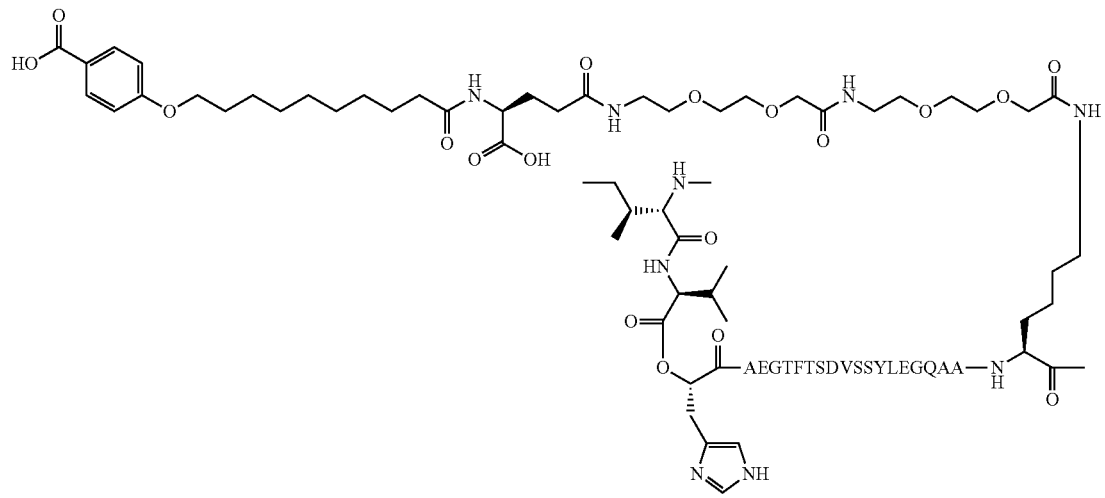

Chem. 54

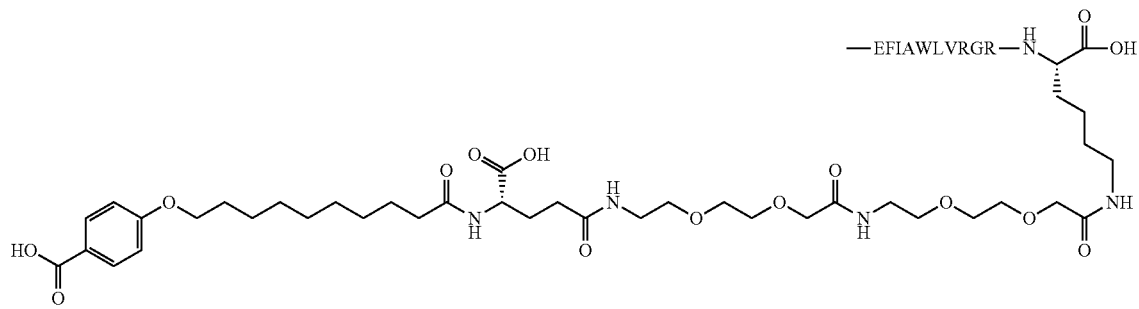

Fully protected [Arg$^{34}$,Lys$^{37}$]-GLP-1-(9-37)-peptide (i.e., SEQ ID NO: 1 in which Ala$^8$ is deleted, and the amino acids at positions 34 and 37 have been substituted with Arg$^{34}$ and Lye, respectively) was synthesised on Fmoc-Lys(Mtt) Wang LL resin according to general method SPPS_P using Fmoc-Lys(Mtt)-OH for lysine positions and leaving an Fmoc protected glutamic acid residue at the N-terminus.

The resin was further processed according to the general method: CP_M2.

For coupling of Boc-NMe-Ile-Val-OH, Boc-N-Me-Ile-Val-OH (6 molar equivalents compared to resin) was dissolved in DCM. MSNT (6 eq) was added followed by methylimidazol (9 eq). The mixture was allowed to stand for 10 minutes after which it was added to the resin prepared above. The resin was shaken for 4 h, then drained and washed 6 times with DCM.

The resin was cleaved and purified according to general method CP_M1 and the fractions containing the right compound were pooled and lyophilised to a white powder.

LCMS method: LCMS_4: Rt: 2.23 min; Exact mass: 5098.584 Da; M/5: 1020.99; M/4: 1275.98

UPLC method: B4_1: Rt=9.485 min

UPLC method: B29_1: Rt=13.070 min

Example 5

$N^{\epsilon 18}$-[2-[2-[2-[[2-[2-[2-[[(4S)-4-carboxy-4-[10-(4-carboxyphenoxyl)decanoylamino]butanoyl]amino]ethoxy]ethoxy]acetyl]amino]ethoxy]ethoxy]acetyl], $N^{\epsilon 26}$-[2-[2-[2-[[2-[2-[2-[[(4S)-4-carboxy-4-[10-(4-carboxyphenoxyl)decanoylamino]-butanoyl]amino]ethoxy]ethoxy]acetyl]amino]ethoxy]ethoxy]acetyl], $N^{\alpha 8}$-{(S)-3-(1H-imidazol-4-yl)-2-[(S)-3-methyl-2-((S)-3-methyl-2-methylamino-pentanoylamino)-butyryloxy]-propionyl}-[Lys$^{18}$,Glu$^{22}$,Gln$^{34}$]-GLP-1-(8-37)-peptide Chem. 55

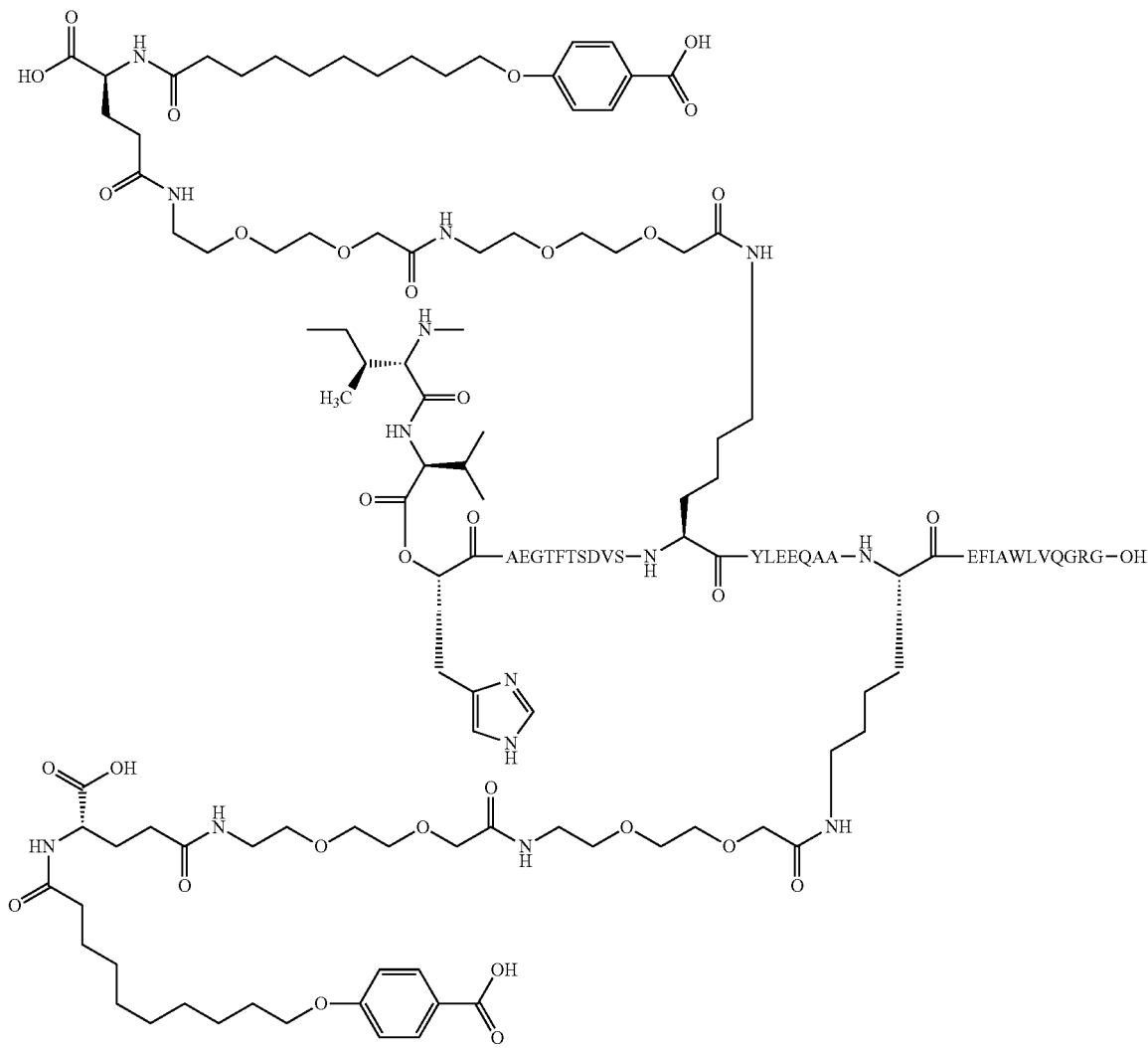

Fully protected [Lys$^{18}$,Glu$^{22}$,Gln$^{34}$]-GLP-1-(9-37)-peptide (i.e., SEQ ID NO: 1 in which Ala$^8$ is deleted, and the amino acids at positions 18, 22, and 34 have been substituted with Lys$^{18}$,Glu$^{22}$, and Gln$^{34}$, respectively) was synthesised on Fmoc-Lys(Mtt) Wang LL resin according to general method SPPS_P using Fmoc-Lys(Mtt)-OH for lysine positions and leaving an Fmoc protected glutamic acid residue at the N-terminus.

The resin was further processed according to the general method: CP_M2.

For coupling of Boc-NMe-Ile-Val-OH, Boc-N-Me-Ile-Val-OH (6 molar equivalents compared to resin) was dissolved in DCM. MSNT (6 eq) was added followed by methylimidazol (9 eq). The mixture was allowed to stand for 10 minutes after which it was added to the resin prepared above. The resin was shaken for 4 h, then drained and washed 6 times with DCM.

The resin was cleaved and purified according to general method CP_M1 and the fractions containing the right compound were pooled and lyophilised to a white powder.

LCMS method: LCMS_4: Rt: 2.30 min; Exact mass: 5112.552 Da; M/5: 1023.78; M/4: 1279.71

UPLC method: B4_1: Rt=11.05 min

UPLC (method: B29_1): Rt=19.60 min

Example 6

N^ε27-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl], N^α8-{(S)-3-(1H-Imidazol-4-yl)-2-[(S)-3-methyl-2-((S)-3-methyl-2-methylamino-butyrylamino)-butyryloxy]-propionyl}-[Aib^8,Glu^22,Arg^26,Lys^27,Arg^34]-GLP-1-(8-37)-peptide

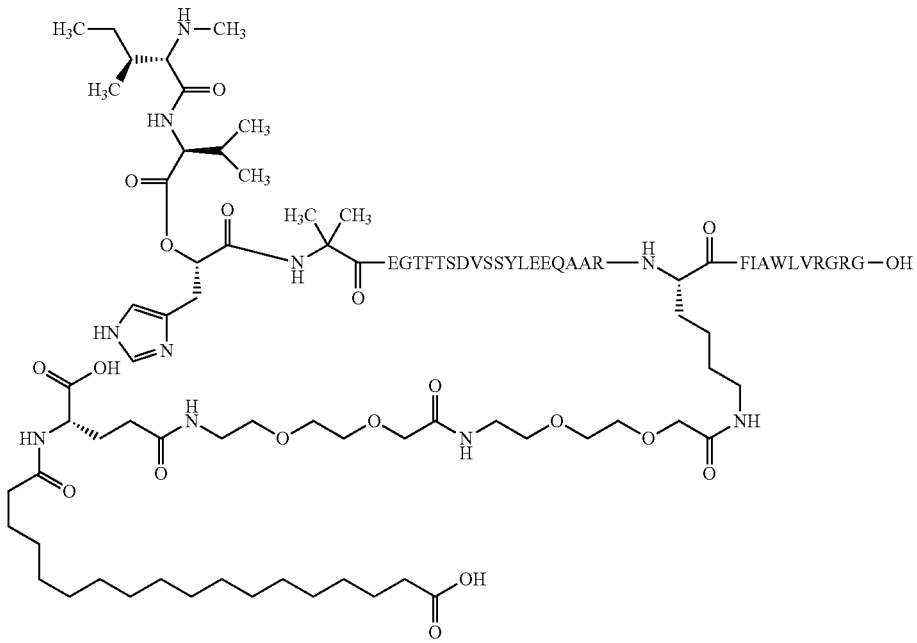

Chem. 56

Fully protected [Glu^22,Arg^26,Lys^27,Arg^34]-GLP-1-(9-37)-peptide (i.e., SEQ ID NO: 1 in which Ala^8 is deleted, and the amino acids at positions 22, 26, 27, and 34 have been substituted with Glu^22, Arg^26, Lys^27, and Arg^34, respectively) was synthesized on Fmoc-Gly Wang LL resin according to standard method SPPS_B leaving an Fmoc protected glutamic acid residue at the N-terminus. The last part of the synthesis was performed as in the following steps:

Step 1. Fmoc Removal:
The Fmoc protecting group on the terminal Glu was removed by treatment with 20% piperidine in NMP for 2 min+18 min followed by 6 times wash with NMP.

Step 2. Coupling of Fmoc-Aib-OH:
Fmoc-Aib-OH (4 molar equivalents compared to resin) was activated with TBTU (3.8 eq), HOBt (4 eq), and DIPEA (4 eq) for 10 minutes, then added to the resin and coupled for 2 h or until negative TNBS test (W. S. Hancock, J. E. Battersby, Analytical Biochemistry 1976, 71(1), 260-264). The resin was washed 6 times with NMP and 10 times with DCM.

Step 3. ε-Lys Mtt Deprotection:
The ε-Lys Mtt protecting group was removed by treatment with 0.5% TFA in DCM for 5 min followed by 3 times 15 min with neet hexafluoroisopropanol. The resin was washed with 6 times with DCM and 6 times with NMP. TNBS test was positive.

Step 4. Side Chain Coupling:
Bis-t-Butyl protected side chain (2-[2-[2-[[2-[2-[2-[[(4S)-5-tert-butoxy-4-[(18-tert-butoxy-18-oxo-octadecanoyl)amino]-5-oxo-pentanoyl]amino]ethoxy]ethoxy]acetyl]amino]ethoxy]ethoxy]acetic acid) (see US2010317057 A1, e.g. Example 4)(4 molar equivalents compared to resin) was dissolved in NMP and pre-activated with TBTU (3.8 eq), HOBt (4 eq), and DIPEA (4 eq) for 15 min., then added to the resin and reacted for 2.5 hours or until TNBS test showed clear beads. The N-terminal Fmoc on Aib8 was removed as above.

Step 5. L-β-Imidazolelactic Acid Coupling:
L-beta-Imidazolelactic acid (4 molar equivalents compared to resin) was dissolved in NMP and activated with PyBOB (3.8 eq), HOBt (4 eq), and TEA (4 eq) for 10 minutes before added to the resin and coupling for 1.5 h.

For coupling of Boc-N-Me-Ile-Val-OH, Boc-N-Me-Ile-Val-OH (6 molar equivalents compared to resin) was dissolved in DCM. MSNT (6 eq) was added followed by methylimidazol (9 eq). The mixture was allowed to stand for 10 minutes after which it was added to the resin prepared above. The resin was shaken for 4 h, then drained and washed 6 times with DCM.

The resin was cleaved and purified according to the general method CP_M1 and the fractions containing the right compound was pooled and lyophilized to a white powder.

LCMS method: LCMS_4: Rt: 2.67 min; Exact mass: 4437.347 Da; M/5: 888.47; M/4: 1110.33; M/3: 1480.43

UPLC method: B4_1: Rt=8.55 min

UPLC method: B29_1: Rt=12.51 min

Comparative Example 6a $N^{\epsilon 27}$-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl], $N^{\alpha 8}$-{(2S)-2-[(2S)-2-[[(2S)-2-amino-3-methyl-butanoyl]amino]-3-methyl-butanoyl]oxy-3-(1H-imidazol-4-yl)propanoyl}-[Aib$^8$,Glu$^{22}$,Arg$^{26}$,Lys$^{27}$,Arg$^{34}$]-GLP-1-(8-37)-peptide

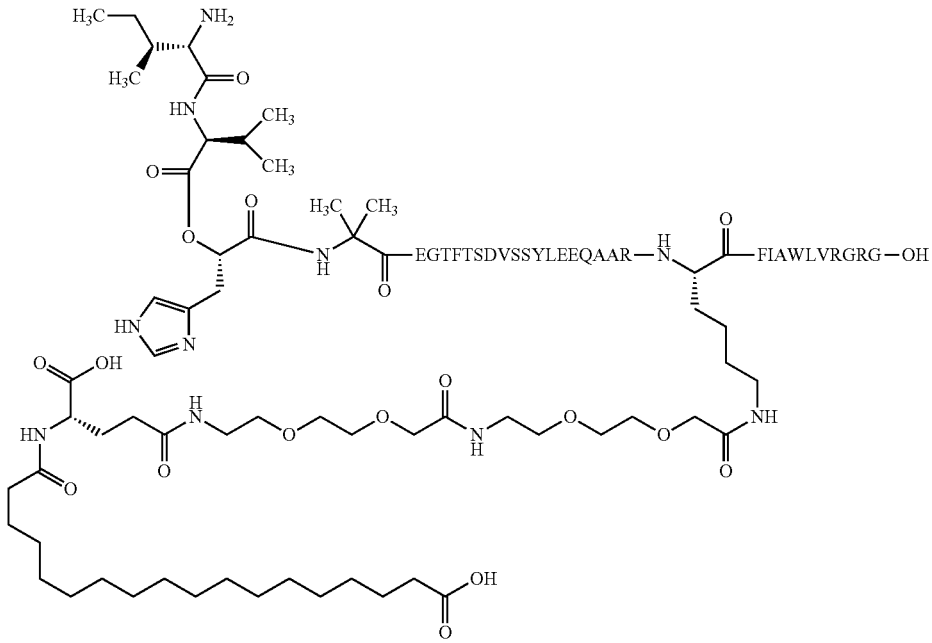

Chem. 34

Fully protected [Lys$^{18}$,Glu$^{22}$,Val$^{26}$,Arg$^{26}$,Lys$^{31}$,Gln$^{34}$]-GLP-1-(9-37)-peptide (i.e., SEQ ID NO: 1 in which Ala$^8$ is deleted, and the amino acids at positions 18, 22, 25, 26, 31, and 34 have been substituted with Lys$^{18}$,Glu$^{22}$,Val$^{25}$,Arg$^{26}$, Lys$^{31}$, and Gln$^{34}$, respectively) was synthesised on Fmoc-Gly Wang LL resin according to general method SPPS_B leaving an Fmoc protected glutamic acid residue at the N-terminus. The last part of the synthesis was performed as in the following steps:

Step 1. Fmoc Removal:

The Fmoc protecting group on the terminal Glu was removed by treatment with 20% piperidine in NMP for 2 min+18 min followed by 6 times wash with NMP.

Step 2. Coupling of Fmoc-Aib-OH:

Fmoc-Aib-OH (4 molar equivalents compared to resin) was activated with TBTU (3.8 eq), HOBt (4 eq), and DIPEA (4 eq) for 10 minutes, then added to the resin and coupled for 2 h or until negative TNBS test (W. S. Hancock, J. E. Battersby, Analytical Biochemistry 1976, 71(1), 260-264). The resin was washed 6 times with NMP and 10 times with DCM.

Step 3. ε-Lys Mtt Deprotection:

The ε-Lys Mtt protecting group was removed by treatment with 0.5% TFA in DCM for 5 min followed by 3 times 15 min with neet hexafluoroisopropanol. The resin was washed with 6 times with DCM and 6 times with NMP. TNBS test was positive.

Step 4. Side Chain Coupling:

Bis-t-Butyl protected side chain (2-[2-[2-[[2-[2-[2-[[(4S)-5-tert-butoxy-4-[(18-tert-butoxy-18-oxo-octadecanoyl)amino]-5-oxo-pentanoyl]amino]ethoxy]ethoxy]acetyl]amino]ethoxy]ethoxy]acetic acid) (US2010317057 A1, see e.g. Example 4) (4 molar equivalents compared to resin) was dissolved in NMP and pre-activated with TBTU (3.8 eq), HOBt (4 eq), and DIPEA (4 eq) for 15 min., then added to the resin and reacted for 2.5 hours or until TNBS test showed clear beads. The N-terminal Fmoc on Aib8 was removed as above.

Step 5. L-β-Imidazolelactic Acid Coupling:

L-beta-Imidazolelactic acid (4 molar equivalents compared to resin) was dissolved in NMP and activated with PyBOB (3.8 eq), HOBt (4 eq), and TEA (4 eq) for 10 minutes before added to the resin and coupling for 1.5 h.

For coupling of Boc-NH-Ile-Val-OH, Boc-NH-Ile-Val-OH (6 molar equivalents compared to resin) was dissolved in DCM. MSNT (6 eq) was added followed by methylimidazol (9 eq). The mixture was allowed to stand for 10 minutes after which it was added to the resin prepared above. The resin was shaken for 4 h, then drained and washed 6 times with DCM.

The resin was cleaved and purified according to the general method CP_M1 and the fractions containing the right compound was pooled and lyophilized to a white powder.

LCMS method: LCMS_4: Rt: 2.68 min; Exact mass: 4423.332 Da; M/5: 885.66; M/4: 1106.82; M/3: 1475.77
UPLC method: B4_1: Rt=8.55 min
UPLC method: B29_1: Rt=12.52 min Pharmacological Methods Example 7

Prodrug Half-Lives In Vitro

The purpose of this example is to test the in vitro half-lives (T½) of the GLP-1 prodrugs of the invention, in comparison to conceptually different prodrugs. In what follows two in vitro methods are described, viz. a method conducted in buffer, and a method conducted in plasma.

Buffer Method

Buffer: 25 mM Phosphate (Ionic strength: 154 mM, pH 7.4 at 37° C.)

$NaH_2PO_4 \cdot 2H_2O$ (1.95 g, 12.5 mmol) and NaCl (2.61 g, 44.7 mmol) were dissolved in millipore water (approximately 450 mL) and adjusted to pH=7.44 at approximately 20° C. with concentrated NaOH and 1 M NaOH. Water was added to 500.00 mL.

The compound to be tested was dissolved in buffer to a concentration of 1.0 mg/mL and incubated at 37° C. Samples were taken at adequate intervals and the % parent drug compared to prodrug formed as function of time was evaluated by the UPLC method as referred to in Table 1 by comparing the areas under the curves for the two corresponding peaks. These UPLC methods are described in the general experimental section above (UPLC_A, and UPLC_B).

The half life of the prodrug (T½) was calculated from the slope of a linear fit to the curve of ln(% prodrug (Y)) as a function of time (t), as follows:

$$Y = -\alpha t + k \qquad \text{Math. 1}$$

$$T\tfrac{1}{2} = \ln(2)/\alpha \qquad \text{Math. 2}$$

Plasma Method

Buffer: 200 mM Phosphate, pH 7.4 at 37° C.

$NaH_2PO_4 \cdot 2H_2O$ (15.61 g, 100 mmol) was dissolved in milliQ water (approximately 450 mL) and adjusted to pH=7.44 at approximately 20° C. with concentrated NaOH (aq) and 1 M NaOH (aq). Water was added to 500.00 mL.

Serum: Minipig Serum, Heparin-Plasma

Fresh blood was tapped from minipig into 9 mL LH lithium heparin Vacuette tubes from Greiner bio-one (catalogue number 455084). After cooling on ice it was centrifuged (10 min, 4° C., 3000 rpm/1942G) and the supernatant isolated and kept at −18° C. before use.

100 nmol of the compound to be tested was dissolved in 200 µL buffer, added to 800 µL plasma (centrifuged), and incubated at 37° C. Samples (50 µL) were drawn at appropriate intervals into 150 µL absolute EtOH. After a short stirring the sample was centrifuged and the supernatant transferred to the UPLC vial (10 µL injection).

The % parent drug compared to prodrug formed as a function of time was evaluated by UPLC, and the half-life calculated, both in the same way as described above under the Buffer method.

The resulting half-lives are set out in Table 1 below. For comparison, the T½ in buffer of native GLP-1(7-37) (His7 variant of SEQ ID NO: 1) was 13 minutes (0.2 hours).

TABLE 1

| Compound of Example no. | T½ in buffer (hours) | T½ in plasma (hours) |
| --- | --- | --- |
| 1 | 9.6 | 3.6 |
| 1a | 1.5 | n.d. |

TABLE 1-continued

| Compound of Example no. | T½ in buffer (hours) | T½ in plasma (hours) |
| --- | --- | --- |
| 1b | 0.65 | n.d. |
| 2* | 42.5 | 27.5 |
| 2a | 10.5 | 4.6 |
| 3 | 38.5 | 25.6 |
| 3a* | 7.5 | 5.0 |
| 4* | 58.9 | 27.9 |
| 5* | 37.9 | 32.2 |
| 6 | 45.6 | 35.4 |
| 6a | 11.0 | 7.6 |

*For these compounds UPLC method UPLC_B was used. For all other compounds UPLC_A was used.
n.d.: Not determined The results of Table 1 show that in the buffer in vitro system the prodrugs of the invention (Examples 1, 2, 3, and 6) have substantially improved half-lives as compared to the corresponding conceptually different prodrugs (compare with Examples 1a and 1 b, 2a, 3a, and 6a, respectively). This is confirmed in plasma (Examples 2, 3, and 6, versus Examples 2a, 3a, and 6a, respectively).

This is evidence that in vitro we can control the conversion constant, k (compare FIG. 1), for the conversion from prodrug to drug and make it long.

Example 8

In Vitro Potency of Drugs (AlphaScreen, Membranes)

The purpose of this example is to test the activity, or potency, in vitro of, for example, the GLP-1 parent drugs of the prodrugs of the invention.

The potencies of the parent GLP-1 drugs of Examples B2.1, B2.2, and B2.3 were determined as described below, i.e. as the stimulation of the formation of cyclic AMP (cAMP) in a medium containing membranes expressing the human GLP-1 receptor.

Principle

Purified plasma membranes from a stable transfected cell line, BHK467-12A (tk-ts13), expressing the human GLP-1 receptor were stimulated with the GLP-1 drug in question, and the potency of cAMP production was measured using the AlphaScreen™ cAMP Assay Kit from Perkin Elmer Life Sciences. The basic principle of The AlphaScreen Assay is a competition between endogenous cAMP and exogenously added biotin-cAMP. The capture of cAMP is achieved by using a specific antibody conjugated to acceptor beads.

Cell Culture and Preparation of Membranes

A stable transfected cell line and a high expressing clone were selected for screening. The cells were grown at 5% $CO_2$ in DMEM, 10% FCS, 1% Pen/Strep (Penicillin/Streptomycin) and preferably 0.5 (alternatively 1.0 mg/ml) of the selection marker G418.

Cells at approximate 80% confluence were washed twice with PBS and harvested with Versene (aqueous solution of the tetrasodium salt of ethylenediaminetetraacetic acid), centrifuged 5 min at 1000 rpm and the supernatant removed. The additional steps were all made on ice. The cell pellet was homogenised by the Ultrathurax for 20-30 s in 10 ml of Buffer 1 (20 mM Na-HEPES, 10 mM EDTA, pH=7.4), centrifuged 15 min at 20,000 rpm and the pellet resuspended in 10 ml of Buffer 2 (20 mM Na-HEPES, 0.1 mM EDTA, pH=7.4). The suspension was homogenised for 20-30 s and centrifuged 15 min at 20,000 rpm. Suspension in Buffer 2, homogenisation and centrifugation was repeated once and the membranes were resuspended in Buffer 2. The protein concentration was determined and the membranes stored at −80° C. until use.

The assay was performed in flat-bottom 96-well plates (Costar cat. no: 3693). The final volume per well was 50 μl.
Solutions and Reagents AlphaScreen cAMP Assay Kit from Perkin Elmer Life Sciences (cat. No: 6760625M); containing Anti-cAMP Acceptor beads (10 U/μl), Streptavidin Donor beads (10 U/μl) and Biotinylated-cAMP (133 U/μl).

AlphaScreen Buffer, pH=7.4: 50 mM TRIS-HCl (Sigma, cat. no: T3253); 5 mM HEPES (Sigma, cat. no: H3375); 10 mM $MgCl_2$, $6H_2O$ (Merck, cat. no: 5833); 150 mM NaCl (Sigma, cat. no: S9625); 0.01% Tween (Merck, cat. no: 822184). The following was added to the AlphaScreen Buffer prior to use (final concentrations indicated): BSA (Sigma, cat. no. A7906): 0.1%; IBMX (Sigma, cat. no. 15879): 0.5 mM; ATP (Sigma, cat. no. A7699): 1 mM; GTP (Sigma, cat. no. G8877): 1 μM.

cAMP standard (dilution factor in assay=5): cAMP Solution: 5 μL of a 5 mM cAMP-stock+495 μL AlphaScreen Buffer.

Suitable dilution series in AlphaScreen Buffer were prepared of the cAMP standard as well as the GLP-1 drug to be tested, e.g. the following eight concentrations of the GLP-1 compound: $10^{-7}$, $10^{-8}$, $10^{-9}$, $10^{-10}$, $10^{-11}$, $10^{-12}$, $10^{-13}$ and $10^{-14}$M, and a series from, e.g., $10^{-6}$ to $3 \times 10^{-11}$ of cAMP.
Membrane/Acceptor Beads Membranes were prepared from hGLP-1/BHK 467-12A cells with a concentration of, preferably, 6 μg/well (alternatively 3 μg/well) corresponding to 0.6 mg/ml (the amount of membranes used pr. well may vary)

"No membranes": Acceptor Beads (preferably 15 μg/ml final, alternatively 2 units/well final) in AlphaScreen buffer "6 (alternatively 3) μg/well membranes": membranes+ Acceptor Beads (15 μg/ml final, alternatively 2 units/well final) in AlphaScreen buffer An aliquot (10 μl) of "No membranes" was added to the cAMP standard (per well in duplicates) and the positive and negative controls An aliquot (10 μl) of "6 (alternatively 3) μg/well membranes" was added to the GLP-1 drugs (per well in duplicate or triplicate wells)

Pos. Control: 10 μl "no membranes"+10 μl AlphaScreen Buffer

Neg. Control: 10 μl "no membranes"+10 μl cAMP Stock Solution (50 μM)

As the beads are sensitive to direct light, any handling was in the dark (as dark as possible), or in green light. All dilutions were made on ice.
Procedure
1. Make the AlphaScreen Buffer.
2. Dissolve and dilute the GLP-1 drugs/cAMP standard in AlphaScreen Buffer.
3. Make the Donor Beads solution (by mixing streptavidin donor beads (2 units/well) and biotynylated cAMP (1.2 units/well) and incubate 20-30 min. in the dark at room temperature.
4. Add the cAMP/GLP-1 drugs to the plate: 10 μl per well.
5. Prepare membrane/Acceptor Beads solution and add this to the plates: 10 μl per well.
6. Add the Donor Beads: 30 μl per well.
7. Wrap the plate in aluminium foil and incubate on the shaker for 3 hours (very slowly) at room temperature.
8. Count on AlphaScreen—each plate pre incubates in the AlphaScreen for 3 minutes before counting.
Results The $EC_{50}$ [nM] values were calculated using the GraphPad Prism software (version 5) and are shown in Table 2 below.

If desired, the fold variation in relation to GLP-1 may be calculated as $EC_{50}$ (GLP-1)/$EC_{50}$ (drug)—3693.2.

TABLE 2

| Compound of Example no. | In vitro potency ($EC_{50}$/pM) |
|---|---|
| B2.1 | 100 |
| Comparative compound (Ex. 75 of PCT/EP2011/069738) | 50 |
| B2.2 | 460 |
| Comparative compound (Ex. 29 of WO 2011/080103) | 180 |
| B2.3 | 1300 |
| Comparative compound (Ex. 38 of PCT/EP2011/069738) | 220 |

The results of Table 2 confirm that all drugs tested have a satisfactory in vitro potency. A somewhat decreased potency was observed for the drugs of the invention as compared to the comparative drugs, however this was expected and is not discouraging and in no way prejudicial to the intended use of these drugs.

Example 9

In Vitro Potency of Drugs (CRE Luciferase; Whole Cells)

The purpose of this example is to test the activity, or potency, of, for example, the GLP-1 parent drugs of the prodrugs of the invention. The in vitro potency is the measure of human GLP-1 receptor activation in a whole cell assay. This method is an alternative to the method of Example 8.

The potencies of the parent GLP-1 drugs of Examples B2.4 and B2.5 were determined as described below.
Principle In vitro potency was determined by measuring the response of the human GLP-1 receptor in a reporter gene assay. The assay was performed in a stably transfected BHK cell line that expresses the human GLP-1 receptor and contains the DNA for the cAMP response element (CRE) coupled to a promoter and the gene for firefly luciferase (CRE luciferase). When the human GLP-1 receptor is activated it results in the production of cAMP, which in turn results in the luciferase protein being expressed. When assay incubation is completed the luciferase substrate (luciferin) is added and the enzyme converts luciferin to oxyluciferin to produce bioluminescence. The luminescence is measured as the readout for the assay.

In order to test the binding of the derivatives to albumin, the assay may if desired be performed in the absence of serum albumin as well as in the presence of a considerably higher concentration of serum albumin (1.0% final assay concentration). An increase of the in vitro potency, $EC_{50}$ value, in the presence of serum albumin would indicate an affinity to serum albumin and represents a method to predict a protracted pharmacokinetic profile of the test substance in animal models.
Cell Culture and Preparation The cells used in this assay (clone FCW467-12A/KZ10-1) were BHK cells with BHKTS13 as a parent cell line. The cells were derived from a clone (FCW467-12A) that expresses the human GLP-1 receptor and were established by further transfection with CRE luciferase to obtain the current clone.

The cells were cultured at 5% $CO_2$ in Cell Culture Medium. They were aliquoted and stored in liquid nitrogen. Before each assay an aliquot is taken up and washed twice in PBS before being suspended at the desired concentration in the assay specific buffer. For 96-well plates the suspension was made to give a final concentration of $5 \times 10^3$ cells/well.

Materials

The following chemicals were used in the assay: Pluronic F-68 (10%) (Gibco 2404), human serum albumin (HSA) (Sigma A9511), ovalbumin (Sigma A5503), DMEM w/o phenol red (Gibco 11880-028), 1 M Hepes (Gibco 15630), Glutamax 100x (Gibco 35050) and steadylite plus (PerkinElmer 6016757).

Cell Culture Medium consisted of DMEM medium with 10% FBS (Fetal Bovine Serum; Invitrogen 16140-071), 1 mg/ml G418 (Invitrogen 15140-122), 240 nM MTX (methotrexate; Sigma M9929) and 1% pen/strep (penicillin/streptomycin; Invitrogen 15140-122).

Assay Medium consisted of DMEM w/o phenol red, 10 mM Hepes and 1x Glutamax. The 1% Assay Buffer consisted of 2% ovalbumin, 0.2% Pluronic F-68 and 2% HSA inassay medium. The 0% Assay Buffer consisted of 2% ovalbumin and 0.2% Pluronic F-68 inAssay Medium.

Procedure

1) Cell stocks were thawed in a 37° C. water bath.
2) Cells were washed three times in PBS.
3) The cells were counted and adjusted to $5 \times 10^3$ cells/50 µl ($1 \times 10^5$ cells/ml) in Assay Medium. A 50 µl aliquot of cells was transferred to each well in the assay plate.
4) Stocks of the test compounds and reference compounds were diluted to a concentration of 0.2 µM in 0% Assay Buffer for the 0% HSA CRE luciferase assay and 1% Assay Buffer for the 1% HSA CRE luciferase assay. Compounds were diluted 10-fold to give the following concentrations: $2 \times 10^{-7}$ M, $2 \times 10^{-8}$ M; $2 \times 10^{-9}$ M, $2 \times 10^{-10}$ M, $2 \times 10^{-11}$ M, $2 \times 10^{-12}$ M, $2 \times 10^{-13}$ M, and $2 \times 10^{-14}$ M.
5) A 50 µl aliquot of compound or blank was transferred from the dilution plate to the assay plate. Compounds were tested at the following final concentrations: $1 \times 10^{-7}$ M, $1 \times 10^{-8}$ M; $1 \times 10^{-9}$ M, $1 \times 10^{-10}$ M, $1 \times 10^{-11}$ M, $1 \times 10^{-12}$ M, $1 \times 10^{-13}$ M, and $1 \times 10^{-14}$ M.
6) The assay plate was incubated for 3 h in a 5% $CO_2$ incubator at 37° C.
7) The assay plate was removed from the incubator and allowed to stand at room temperature for 15 min.
8) A 100 µl aliquot of steadylite plus reagent was added to each well of the assay plate (reagent was light sensitive).
9) Each assay plate was covered with aluminum foil to protect it from light and shaken for 30 min at room temperature.
10) Each assay plate was read in a Packard TopCount NXT instrument.

Calculations and Results

The data from the TopCount instrument were transferred to Graph Pad Prism software. The software performs a non-linear regression (log(agonist) vs response). $EC_{50}$ values which were calculated by the software and reported in pM are shown in Table 2 below.

A minimum of two replicates was measured for each sample. The reported values are averages of the replicates.

TABLE 3

| Compound of Example no. | In vitro potency ($EC_{50}$/pM) 0% HSA |
|---|---|
| B2.4 | 4.0 |
| B2.5 | 31 |
| Benchmark compound (Ex. 38 of PCT/EP2011/069738) | 25 |

The results of Table 3 confirm that the two drugs tested have a satisfactory in vitro potency generally on par with the benchmark compound.

Example 10

GLP-1 Receptor Binding

The purpose of this experiment is to test the receptor binding activity of the GLP-1 parent drugs of the prodrugs of the invention. The receptor binding is a measure of affinity of a parent drug for the human GLP-1 receptor. The parent GLP-1 drugs of Examples B2.1, B2.2, B2.3, B2.4, and B2.5 were tested as described below.

Principle

The receptor binding of the GLP-1 drugs to the human GLP-1 receptor was measured in a competitive binding assay. In this type of assay a labelled ligand (in this case $^{125}$I-GLP-1) is bound to the receptor. Each drug is added in a series of concentrations to isolated membranes containing the human GLP-1 receptor and displacement of the labelled ligand is monitored. The receptor binding is reported as the concentration at which half of the labelled ligand is displaced from the receptor, the $IC_{50}$ value.

In order to test the binding of the drugs to the receptor in the presence of albumin, the assay may be performed in a very low concentration of serum albumin (preferably max 0.001% final assay concentration (alternatively 0.005%—corresponding to the residual amount thereof in the tracer), as well as in the presence of a considerably higher concentration of serum albumin (2.0% final assay concentration). An increase of the $IC_{50}$ value in the presence of serum albumin indicates an affinity to serum albumin and represents a method to predict a protracted pharmacokinetic profile of the test substance in animal models.

Materials

The following chemicals were used in the assay: Human serum albumin (HSA) (Sigma A1653), DMEM w/o phenol red (Gibco 11880-028), Pen/strep (Invitrogen 15140-122), G418 (Invitrogen 10131-027), 1 M Hepes (Gibco 15630), EDTA (Invitrogen 15575-038), PBS (Invitrogen 14190-094), fetal calf serum (Invitrogen 16140-071), EGTA, $MgCl_2$ (Merck 1.05832.1000), Tween 20 (Amresco 0850C335), SPA particles (wheat germ agglutinin (WGA) SPA beads, Perkin Elmer RPNQ0001), [$^{125}$I]-GLP-1]-(7-36) $NH_2$ (produced in-house), OptiPlate™-96 (Packard 6005290).

Buffer 1 consisted of 20 mM Na-HEPES plus 10 mM EDTA and pH was adjusted to 7.4. Buffer 2 consisted of 20 mM Na-HEPES plus 0.1 mM EDTA and pH was adjusted to 7.4. Assay buffer consisted of 50 mM HEPES supplemented with 5 mM EGTA, 5 mM $MgCl_2$, 0.005% Tween 20 and pH was adjusted to 7.4. An 8% albumin stock consisted of HSA dissolved at 8% (w/v) in assay buffer. An 0.02% albumin stock consisted of HSA dissolved at 0.02% (w/v) in assay buffer.

Cell Culture and Membrane Preparation

Species (in vitro): Hamster
Biological End Point: Receptor Binding
Assay Method: SPA
Receptor: GLP-1 receptor
Cell Line: BHK tk-ts13

The cells used in this assay (clone FCW467-12A) were BHK cells with BHKTS13 as a parent cell line. The cells express the human GLP-1 receptor.

The cells were grown at 5% $CO_2$ in DMEM, 10% fetal calf serum, 1% Pen/Strep (Penicillin/Streptomycin) and 1.0 mg/ml of the selection marker G418. To make a membrane preparation the cells were grown to approximately 80% confluence. The cells were washed twice in phosphate-buffered saline and harvested, for example harvested with Versene (aqueous solution of the tetrasodium salt of ethylenediaminetetraacetic acid), centrifuged briefly, e.g. 5 min at 1000 rpm, and the supernatant removed. The cell pellet was kept on ice. The cell pellet was homogenised with ULTRA-THURRAX™ dispersing instrument for 20-30 seconds in a suitable amount of buffer 1 (e.g., 10 ml, or 10-20 ml). The homogenate was centrifuged for 15 minutes e.g. at 20,000 rpm. The pellet was re-suspended (homogenised) in a suitable amount such as 10 ml, or 10-20 ml, of buffer 2 and centrifuged as above. This step was repeated once more. The resulting pellet was re-suspended in buffer 2 and the protein concentration was determined. The membranes were aliquoted and stored at minus 80° C.

Procedure

For the SPA Binding assay, test compounds, membranes, SPA-particles and [$^{125}$I]-GLP-1(7-36)NH$_2$ were diluted in assay buffer. 25 ul (microliter) of test compounds are added to Optiplate. Buffer ("low albumin" experiment containing 0.005% HSA), was added (50 ul). 5-10 ug protein/sample was added (50 ul) corresponding to 0.1-0.2 mg protein/ml (to be preferably optimised for each membrane preparation). SPA-particles (Wheatgerm agglutinin SPA beads, Perkin Elmer, #RPNQ0001) were added in an amount of 0.5 mg/well (50 ul). The incubation was started with [$^{125}$I]-GLP-1(7-36)NH$_2$ (final concentration 0.06 nM corresponding to 49.880 DPM, 25 ul). The plates were sealed with PlateSealer and incubated for 120 minutes at 30° C. while shaking. The plates were centrifuged (1500 rpm, 10 min) and counted in Topcounter. The following procedure is preferably followed:

1. For the receptor binding assay in the presence of low HSA (0.005%) 50 µl of the assay buffer was added to each well of an assay plate. Assay continued with step 3.
2. For the receptor binding assay in the presence of high HSA (2%) 50 µl of the 8% albumin stock was added to each well of an assay plate. Assay continued with step 3.
3. Test compounds were serially diluted to give the following concentrations: $8 \times 10^{-7}$ M, $8 \times 10^{-8}$ M, $8 \times 10^{-9}$ M, $8 \times 10^{-10}$ M, $8 \times 10^{-11}$ M, $8 \times 10^{-12}$ M and $8 \times 10^{-13}$ M. Twenty-five µl were added to appropriate wells in the assay plate.
4. Cell membrane aliquots were thawed and diluted to their working concentration. Fifty µl were added to each well in the assay plate.
5. WGA SPA beads were suspended in assay buffer at 20 mg/ml. The suspension was diluted to 10 mg/ml in assay buffer just prior to addition to the assay plate. Fifty µl were added to each well in the assay plate.
6. The incubation was started by adding 25 µl of 480 pM solution of [$^{125}$I]-GLP-1]-(7-36)NH$_2$ to each well of the assay plate. A 25 µl aliquot was reserved for measuring total counts/well.
7. The assay plate was incubated for 2 h at 30° C.
8. The assay plate was centrifuged for 10 min.
9. The assay plate was read in a Packard TopCount NXT instrument.

Calculations

The data from the TopCount instrument were transferred to GraphPad Prism software. The software averaged the values for the replicates and performed a non-linear regression. IC$_{50}$ values were calculated by the software and reported in nM.

Results

The results are shown in Table 4 below.

TABLE 4

| Compound of Example no. | Receptor binding Low albumin (IC$_{50}$/nM) |
| --- | --- |
| B2.1 | 4.42 |
| Comparative compound (Ex. 75 of PCT/EP2011/069738) | 0.68 |
| B2.2 | 14.8 |
| Comparative compound (Ex. 29 of WO 2011/080103) | 1.90 |
| B2.3 | 28 |
| Comparative compound (Ex. 38 of of PCT/EP2011/069738) | 5.80 |
| B2.4 | 0.09 |
| B2.5 | 0.22 |

The results of Table 4 confirm that all drugs tested have a satisfactory biological activity, determined as binding to the GLP-1 receptor in the presence of a low concentration of albumin. As compared to the comparative drugs (where available) a somewhat decreased activity was observed for some of the drugs of the invention, however this was expected and is not discouraging and in no way prejudicial to the intended use of these drugs.

Example 11

Resistance to DPP-IV Degradation

The purpose of this experiment is to determine the degradation by Dipeptidyl peptidase-4 (DPP-IV) of the parent drugs of the prodrugs of the invention.

The stability of the parent GLP-1 drug of Example B2.1 was tested as described below.

Buffers
HEPES Buffer (50 mM HEPES Buffer with 0.005% Tween20, pH 7.4)
10 ml 1 M HEPES+100 µl 10% Tween20 adjusted to pH 7.4 and diluted with MilliQ water ad 200 mL Stock Solutions
Stock Solution of Parent GLP-1 Drug with BSA
  1.0 mM in HEPES buffer 0.1% BSA (Sigma cat. no. A9418)
Stock Solution of Parent GLP-1 Drug without BSA
  1.0 mM in hepes buffer pH 7.4
Stock Solution of DPP-IV
DPP-IV was Recombinant Dipeptidyl Peptidase, R&D Systems, cat no. 1180-SE
  50 µl of DPP-IV (0.2 mg/mL), 25 mM MES, 0.7 M NaCl, pH 5.0
Work Solution of DPP-IV
  Add 200 µl 25 mM TRIS pH 8.0 to Stock vial (DPP-IV concentration 40 µg/mL). Just before use: 210 µl (40 µg/ml) is added 210 µl 50 mM HEPES (DPP-IV concentration 20 µg/mL)

Incubations
Pre-Incubation of Plates
  Minimum 30 min, 37° C. with 600 µl 0.1% OVAlbumin. Then left overnight at 4° C. and washed times with 50 mM HEPES.
Before Experiment
  Minimum 150 min with HEPES buffer at 37° C.
Dishes
  Costar 96—semi deep well (cci-3957)
Total Incubation Volume
  300 µL
Incubation All

| 267 µL 50 HEPES buffer | T÷150 min |
| --- | --- |
| 3 µL of compound (1.0 mM) ± BSA | T÷150 min |
| 30 µL of work enzyme solution | T÷0 min |

Incubation Time
  1-30-60-120-180 and 1440 min (37° C.)
Stop of Incubation
  The reactions were terminated by moving 25 µl of the sample into 150 µl cooled 1% TFA in EtOH. Samples were collected in a v-shaped 96-well plate (polypropylene, Costar 3957), (Cat no. cci-3957)). Samples were sealed and kept on ice until analyses.
Analyses
LC-MS Analysis in Supernatants in a Non-Coated 96Well Plates (Polypropylene, WATERS No. 186002643)
  Samples were diluted 5 times in 50% acetonitrile (1% formic acid) (20 µL+80 µL) and analysed with UPLC-MS.
Results
  The results without BSA are shown in Table 5 below, and the results with BSA are shown in Table 6.

TABLE 5

Concentration of parent GLP-1 peptide drug vs time (without BSA)

| Time (t)/minutes | ln (concentration) |
|---|---|
| 1440 | 4.45 |
| 183 | 4.64 |
| 120 | 4.50 |
| 60 | 4.63 |
| 32 | 4.59 |
| 1.0 | 4.61 |

TABLE 6

Concentration of parent GLP-1 peptide drug vs time (with BSA)

| Time (t)/minutes | ln (concentration) |
|---|---|
| 1440 | 4.47 |
| 183 | 4.58 |
| 120 | 4.40 |
| 60 | 4.58 |
| 32 | 4.61 |
| 1.0 | 4.61 |

The amounts of parent GLP-1 drug and DPP-IV cleaved drug were measured from the total ion counts and T½ was determined from a linear fit to the curve of ln (% parent GLP-1 drug) (Y) as a function of time (t), as follows:

$$Y(t) = -\alpha t + k \quad \text{Math 3}$$

$$T\frac{1}{2} = \ln 2/\alpha \quad \text{Math 4}$$

T½ (÷BSA): 3466 min
T½ (+0.001% BSA): 2311 min

Example 12

Pharmacokinetic Study in Minipigs

Example 7 herein provides evidence that in vitro we can control the conversion constant, k (compare FIG. 1) for the conversion from prodrug to drug and make it long.

In vivo other reactions/mechanisms are added on top which complicate the picture, e.g. clearance.

The purpose of this study is to determine the pharmacokinetic (PK) profile in vivo of a prodrug of the invention (Example 4) and the corresponding parent drug (Example B2.2) after i.v. administration to minipigs, e.g. the prolongation of their time in the body and thereby their time of action. This is done in a PK study, where the terminal half-life of the compound in question is determined. By terminal half-life is generally meant the period of time it takes to halve a certain plasma concentration, measured after the initial distribution phase.

Three female Göttingen minipigs, obtained from Ellegaard Göttingen Minipigs (Dalmose, Denmark) approximately 6-8 months of age and weighing approximately 16-21 kg (prodrug pig 16.8 kg, drug pigs 21.3 and 21.1 kg), were used in the studies. The minipigs were housed individually and fed restrictedly once daily with SDS minipig diet (Special Diets Services, Essex, UK).

A permanent central venous catheter was implanted in vena cava caudalis in each animal after 2 weeks of acclimatisation.

The animals were fasted for approximately 18 h before dosing and from 0 to 4 h after dosing, but had ad libitum access to water during the whole period.

The prodrug of Example 4 and the corresponding drug of Example B2.2 were dissolved in 50 mM sodium phosphate, 145 mM sodium chloride, 0.05% polysorbate 80, pH 7.4 to a suitable concentration (for example, 169.6 nmol/ml for the prodrug). Intravenous injections (the volume corresponding to 8 nmol/kg for the prodrug or 3 nmol/kg for the drug of the compounds were given through the catheter, and blood was sampled at predefined time points for 12 days post dosing. Blood samples (0.8 ml for the drug, 1.5 ml for the prodrug) were collected in EDTA buffer (8 mM) and then centrifuged at 4° C. and 1942G for 10 minutes. After centrifugation the prodrug plasma was transferred ASAP into micronic tubes: 300 µl for analysing of the respective GLP-1 compound and snap-frozen ASAP (Dry ice). After centrifugation the drug plasma was pippetted into Micronic tubes on dry ice, and kept at −20° C. until analyzed for plasma concentration of the respective GLP-1 compound using ELISA or a similar antibody based assay such as LOCI, or LC-MS. Individual plasma concentration-time profiles were analyzed by a non-compartmental model in WinNonlin v. 5.0 or Phoenix v. 6.2 (Pharsight Inc., Mountain View, Calif., USA), or other relevant software for PK analysis, and the plasma concentration (pM) versus time (h) curves were plotted, see FIGS. 2 and 3. Also, the resulting terminal half-lives (harmonic mean/h) were determined, if possible.

Results

The half-life results are shown in Table 7 below

For the prodrug compound, which is converted during the experiment, we have estimated the apparent terminal half-life of the drug in the prodrug study. As we could not fit the data to a model we could not predict the very terminal part of the curve. The observed half-life of 68 h is thus estimated from the observed bell-shaped curve form which is the product of a complicated set of equlibria. The single data cannot be fitted to a two-compartment model due to over parameterisation (two many variables compared to statistic material).

TABLE 7

Terminal half-life (harmonic mean) parent GLP-1 peptide drug in vivo

| Compound of Example no. | Terminal half-life (harmonic mean/h) |
|---|---|
| 4 | apparent terminal half-life of corresponding drug: 68 h (estimated) |
| B2.2 | 37 h |

This example confirms that the conversion constants, Kc, for the clearance reactions (of prodrug and of drug) are very low in comparison to that of the conversion constant, k, from prodrug to drug (compare FIG. 1).

Thus, this example constitutes proof of the prodrug concept in vivo.

It is noted that as a result we get the desired bell-shaped curve of the drug, i.e. an improved plasma level profile without a high initial plasma concentration where we would risk to enter the toxic level. With an optimised dosage of the prodrug the bell-shaped plasma level profile allows for reaching a longer lasting pharmacodynamic effect within the relevant therapeutic window.

Figure 2:
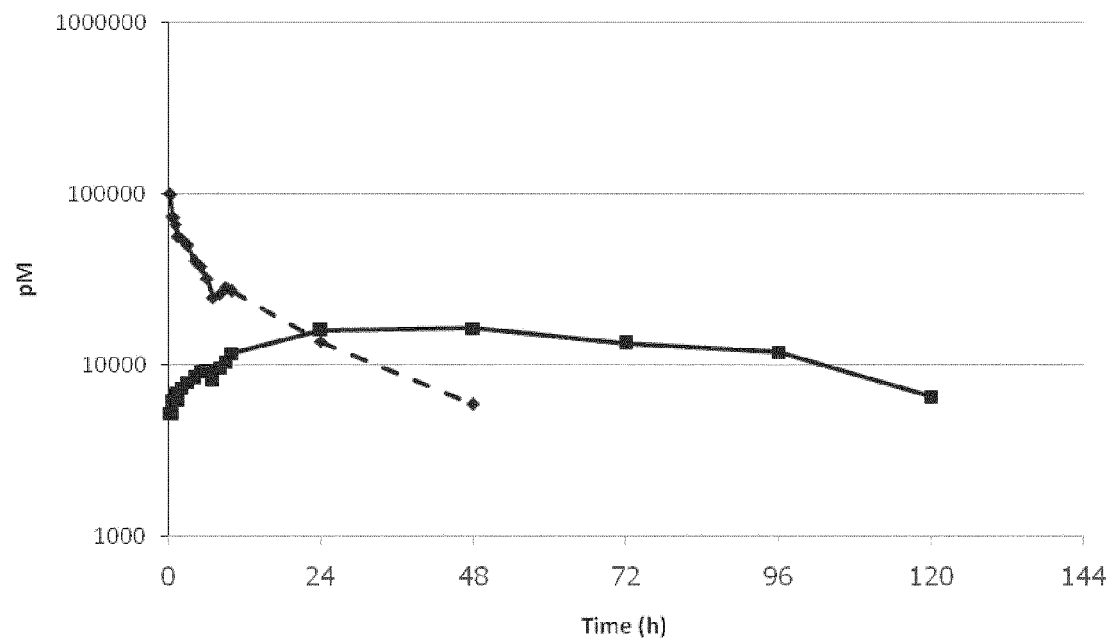
FIG. 2 shows the measured PK profiles of a prodrug of the invention and the corresponding parent drug in mini-pig (diamonds represent the prodrug of Example 4 herein and squares represent the parent drug of Example B2.2 herein)

FIG. 2 shows the measured PK profiles of prodrug and parent drug in mini-pig (the diamonds represent prodrug measurements, and the squares represent parent drug measurements).

Figure 3:
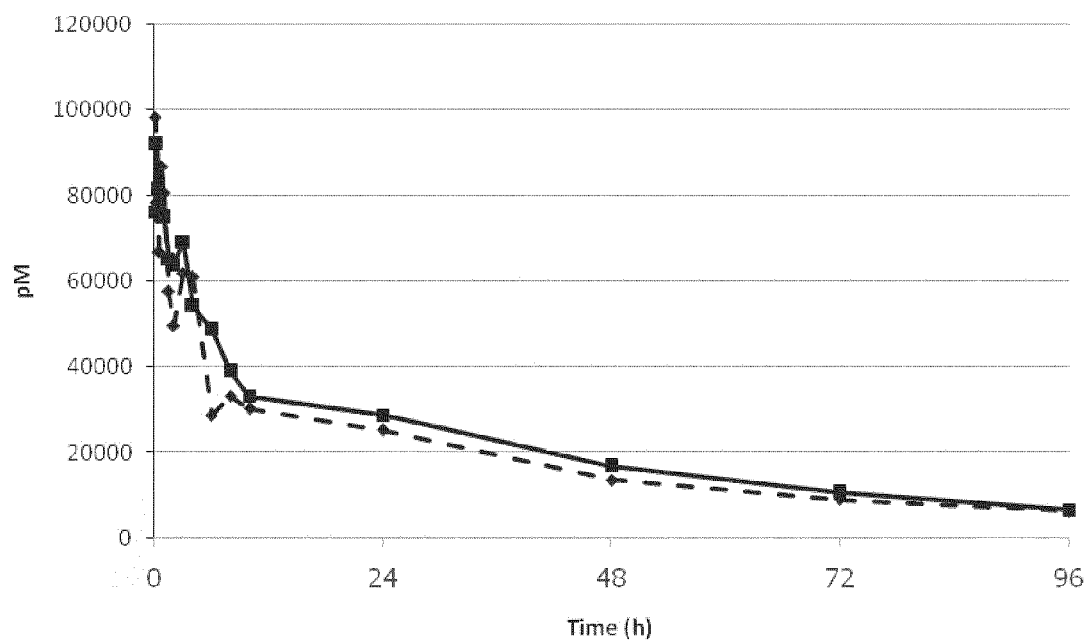
FIG. 3 shows the measured PK profile of a parent drug of the invention in mini-pig (parent drug of Example B2.2 herein; two animals, one represented with diamonds and one with squares).

FIG. 3 shows a PK profile of the parent drug administered as such (not as a prodrug). When compared with the PK profile of FIG. 2 we see the difference: FIG. 3 is a curve like that for the prodrug, not of the desirable bell-shape.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A GLP-1 compound of the general formula I:

R1-(NHXaa1)-Xaa2-(OHis)-(GLP-1 peptide)    (Formula I)

where (OHis) is a radical of imidazole-lactic acid of formula Chem. 1:

Chem. 1 and wherein the GLP-1 compound is produced via the left hand *—O in (OHis) forming an ester with the COOH at the C-terminal of the XAA2 amino acid and the right hand O—* in (OHis) forming an amide bond with the NH$_2$ terminus of the GLP-1 peptide, where the GLP-1 peptide is GLP-1(8-37) (SEQ ID NO: 1), an analogue of GLP-1(8-37) (SEQ ID NO: 1) having Formula III: Xaa$_8$-Glu-Gly-Thr-Xaa$_{12}$-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Lys-Xaa$_{38}$, wherein Xaa$_8$ is Ala, Gly, Val, Leu, Ile, Thr, Ser, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
Xaa$_{12}$ is Phe or Leu;
Xaa$_{16}$ is Val or Leu;
Xaa$_{18}$ is Ser, Val, Lys, or Leu;
Xaa$_{19}$ is Tyr or Gln;
Xaa$_{20}$ is Leu or Met;
Xaa$_{22}$ is Gly, Glu, or Aib;
Xaa$_{23}$ is Gln, Glu, or Arg;
Xaa$_{25}$ is Ala or Val;
Xaa$_{26}$ is Lys or Arg;
Xaa$_{27}$ is Lys, Glu, or Leu;
Xaa$_{30}$ is Ala, Glu, or Arg;
Xaa$_{31}$ is Trp, Lys, or His;
Xaa$_{33}$ is Val;
Xaa$_{34}$ is Glu, Asn, Gly, Gln, Arg, or His;
Xaa$_{35}$ is Gly or Aib;
Xaa$_{36}$ is Arg or Gly;
Xaa$_{37}$ is Lys, Arg, or Gly; and
Xaa$_{38}$ is Ser, Gly, Ala, Glu, Pro, Arg, or absent; or a derivative of an analogue of Formula III wherein at least one substituent comprising a fatty acid or fatty diacid is attached to the epsilon amino group of a Lys residue at a position corresponding to at least one of the following positions of Formula III: 18, 26, 27, 31, and/or 37;

R1 is lower alkyl;
(NHXaa1) is an amino acid; and
Xaa2 is an amino acid;

or a pharmaceutically acceptable salt, amide, or ester thereof.

2. The compound of claim 1, wherein the bonds between (NHXaa1) and Xaa2 is an amide bond, and wherein R1 is attached to the alpha-amino group of (NHXaa1).

3. The compound of claim 1, wherein R1 is methyl.

4. The compound of claim 1, wherein (NHXaa1) is Gly, Val, or Ile.

5. The compound of claim 1, wherein Xaa2 is Val.

6. The compound of claim 1, wherein the GLP-1 peptide is a derivative of an analogue of Formula III.

7. The compound of claim 6, wherein the GLP-1 peptide is a derivative which has
   i) one substituent attached to position 26 or 27; or
   ii) one substituent attached to a) each of positions 18 and 31, b) each of positions 26 and 37, or c) each of positions 18 and 26; wherein the position numbering refers to Formula III.

8. A compound selected from
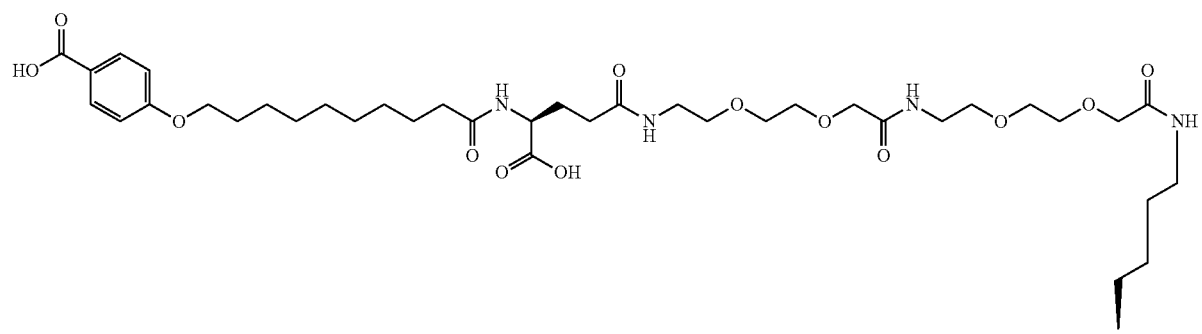
Chem. 51
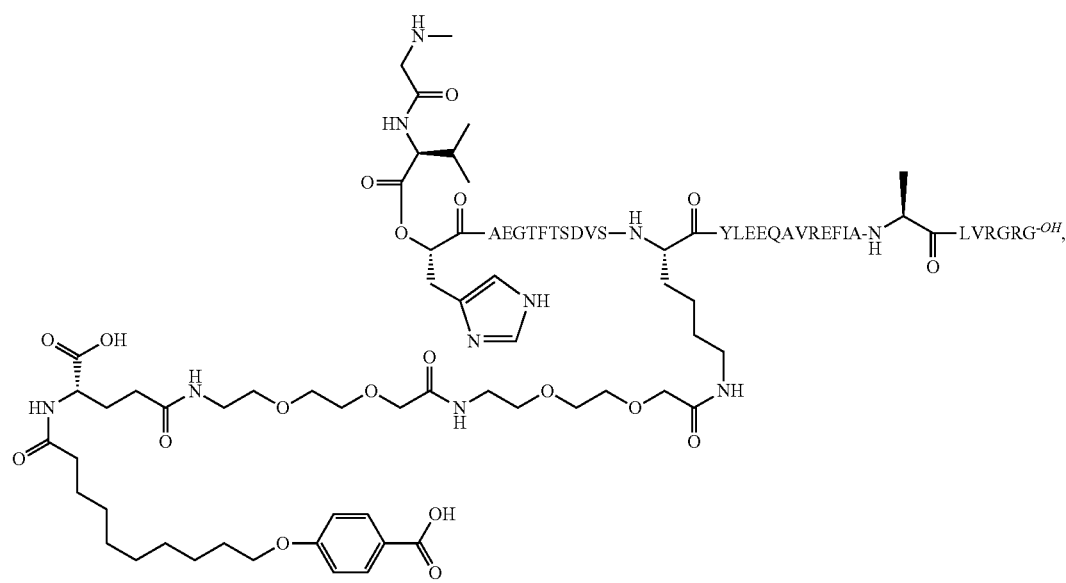
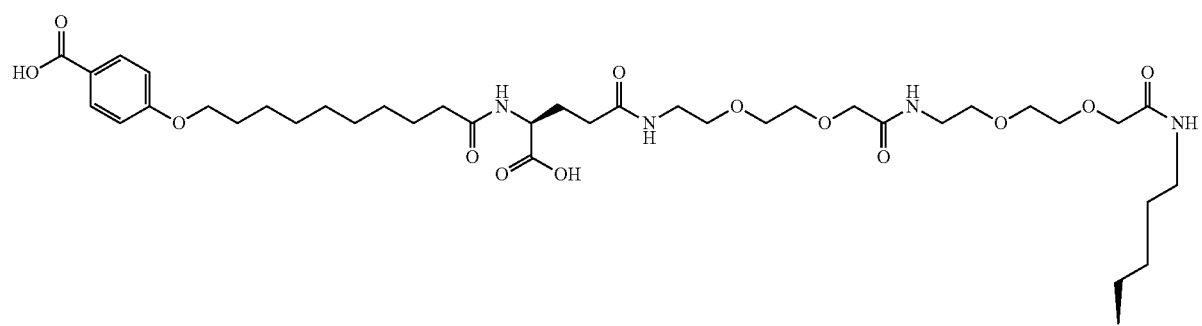
Chem. 52

-continued
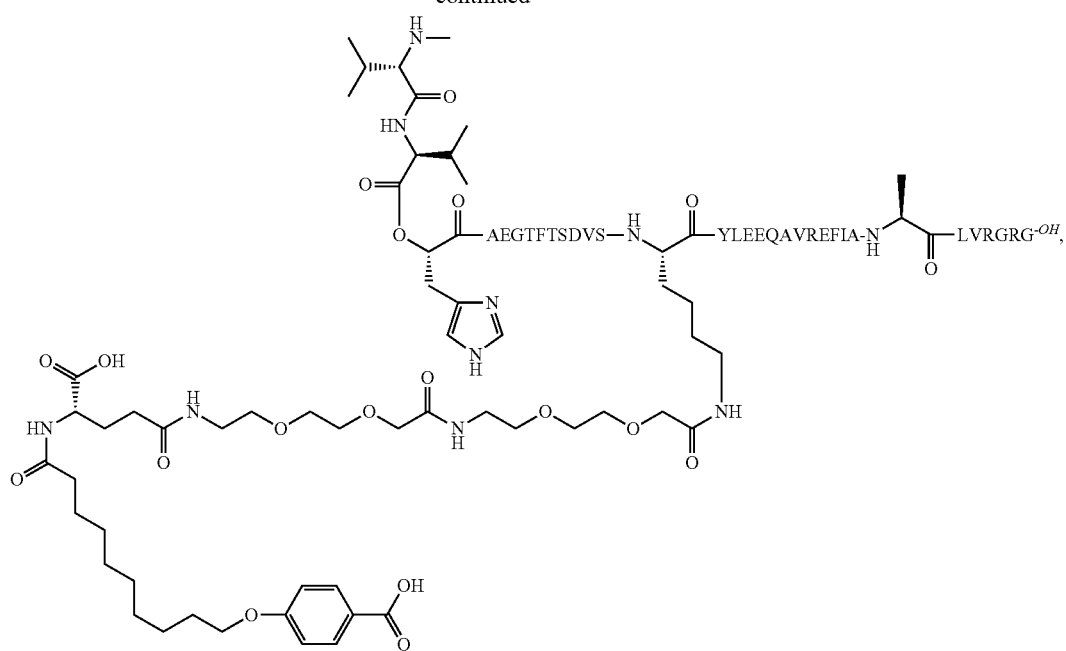
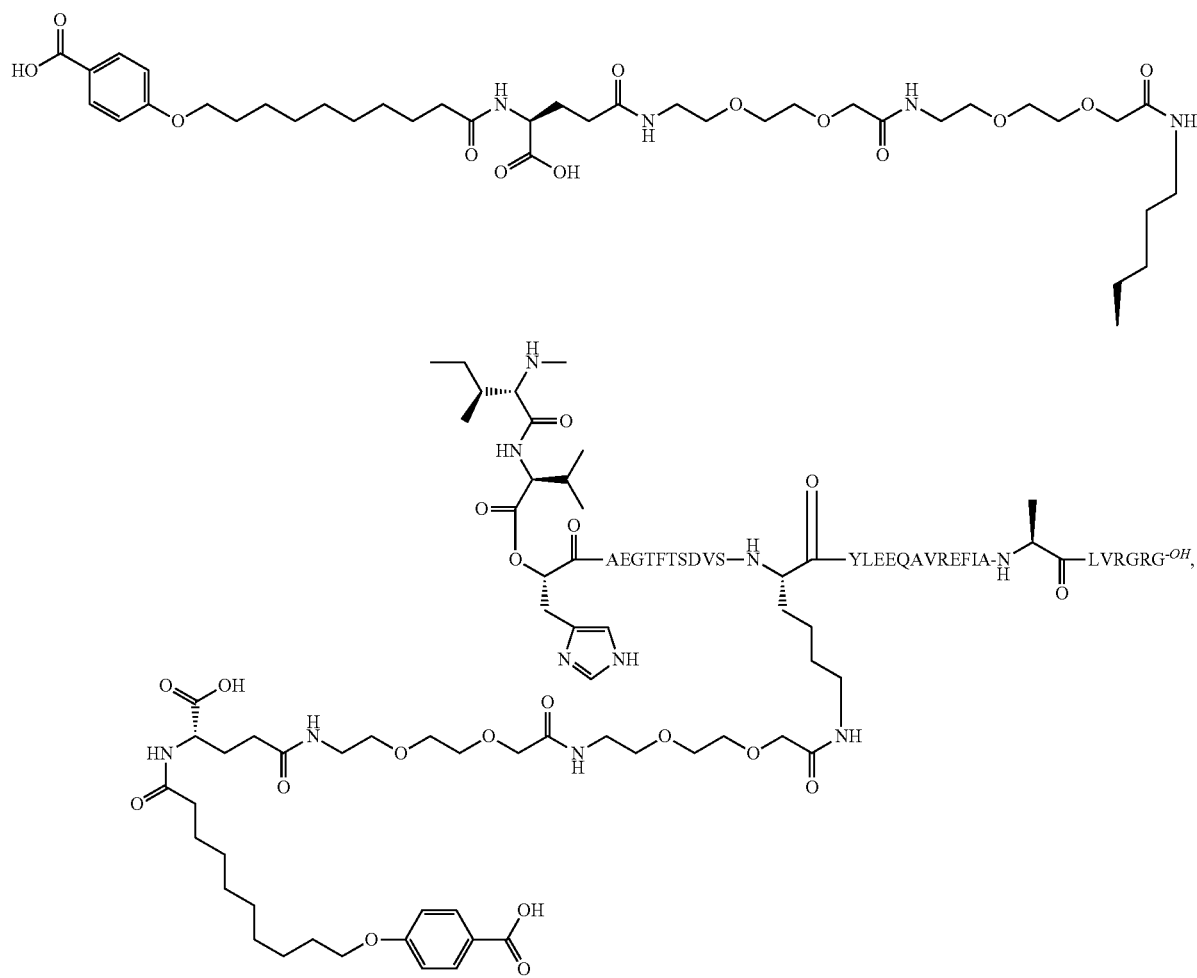
Chem. 53

Chem. 54
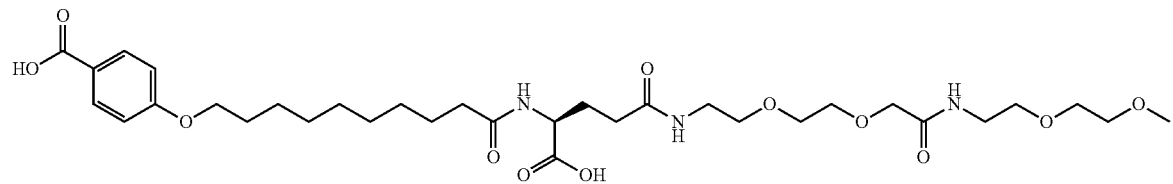
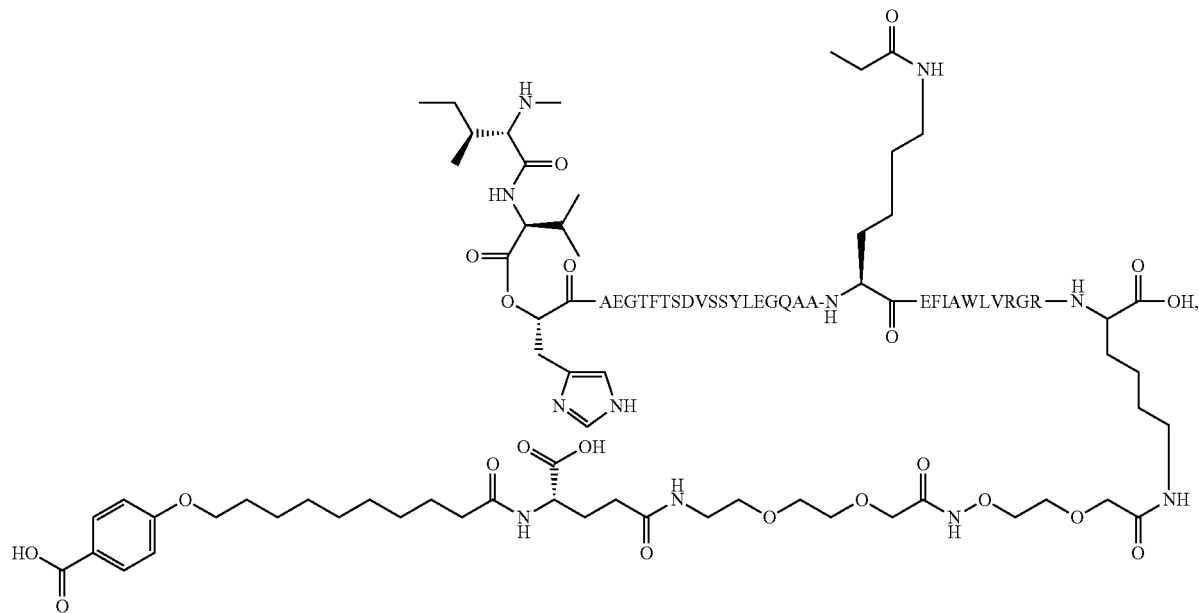
Chem. 55
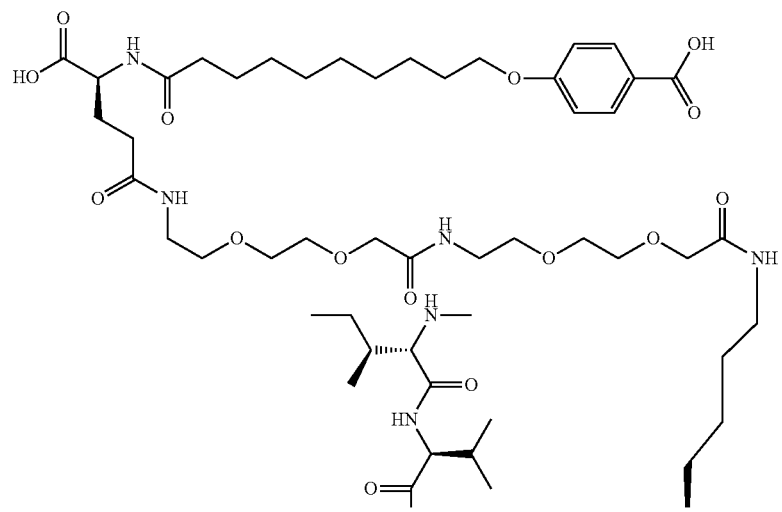

-continued

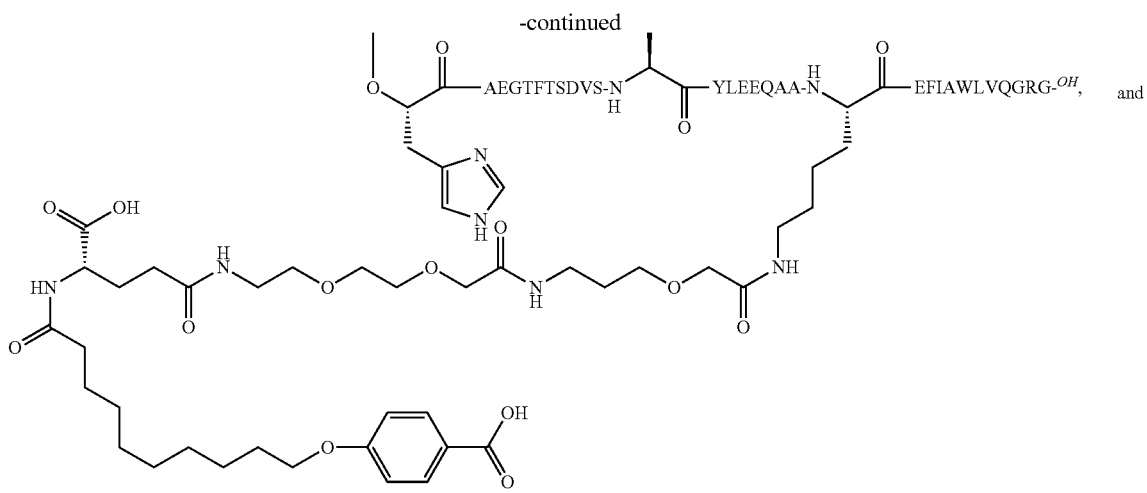

, and

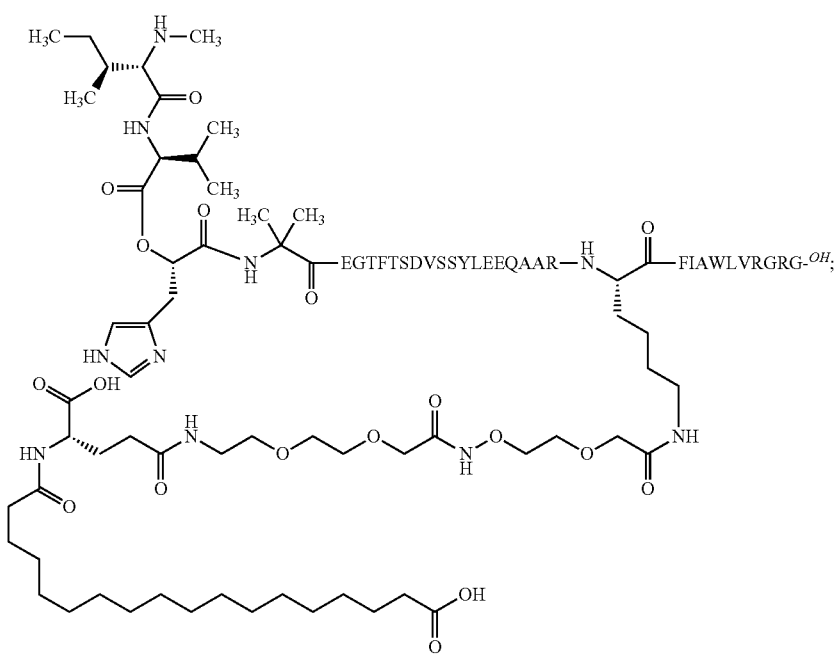

;

or a pharmaceutically acceptable salt, amide or ester thereof.

9. A method of achieving release in vivo of an active and stabilised parent drug GLP-1 compound of the general formula II: (HOHis)-(GLP-1 peptide), or a pharmaceutically acceptable, salt, amide, or ester thereof, by administering a compound as defined in claim 1.

10. A pharmaceutical composition comprising a compound according to claim 1 and a pharmaceutically acceptable excipient.

11. A method for treating diabetes in a subject in need of such treatment, said method comprising administering to said subject a therapeutically effective amount of the pharmaceutical composition of claim 10.

* * * * *